United States Patent [19]
Smith et al.

[11] Patent Number: 5,515,853
[45] Date of Patent: May 14, 1996

[54] THREE-DIMENSIONAL DIGITAL ULTRASOUND TRACKING SYSTEM

[75] Inventors: Wayne L. Smith, London, Canada; Ivan Vesely, Cleveland Heights, Ohio; Andrew W. Gubbels, Mt. Brydges, Canada

[73] Assignee: Sonometrics Corporation, London, Canada

[21] Appl. No.: 411,959

[22] Filed: Mar. 28, 1995

[51] Int. Cl.⁶ ........................................... A61B 8/00
[52] U.S. Cl. ...................... 128/661.01; 128/916
[58] Field of Search .............. 128/660.06, 660.07, 128/660.08, 660.09, 661.01, 916; 73/624, 625, 626, 602

[56] References Cited

U.S. PATENT DOCUMENTS

| | | | |
|---|---|---|---|
| 4,100,916 | 7/1978 | King | 128/660.07 |
| 4,785,817 | 11/1988 | Stouffer | 73/602 |
| 5,443,489 | 8/1995 | Ben-Haim . | |

OTHER PUBLICATIONS

Annual International Conference of the IEEE Engineering In Medicine and Biology Society, vol. 13, No. 4, 1994, "Three Dimensional Ultrasonic Micrometer For Use In Cardiovascular Research" by W. Smith, I. Vesely.

"Sonomicrometer Enhancement Implementing 16-Bit Counters into EPLDs" by Andrew Gubbels— E. S. 400— Project Report.

*Primary Examiner*—George Mamuel
*Attorney, Agent, or Firm*—Fay, Sharpe, Beall, Fagan, Minnich & McKee

[57] ABSTRACT

A method and apparatus for simultaneous measurement of multiple distances by means of networked piezoelectric transducers. Through the use of high frequency digital counters, the propagation delay between the activation of an ultrasonic transducer and the reception by similar transducers is quickly and accurately defined. By alternating the duty cycle between transmit and receive modes, the system can track and triangulate the three-dimensional positions for each transducer.

16 Claims, 64 Drawing Sheets

Radio-opaque ultrasonic transducers on a chest harnass

| FIG.2A. | FIG.2C. |
|---|---|
| FIG.2B. | FIG.2D. |

FIG.2.

| | FIG.3A. | FIG.3B. | FIG.3C. |
|---|---|---|---|
| FIG.3D. | FIG.3E. | FIG.3F. | FIG.3G. |
| FIG.3H. | FIG.3I. | FIG.3J. | FIG.3K. |
| FIG.3L. | FIG.3M. | FIG.3N. | |
| FIG.3O. | FIG.3P. | FIG.3Q. | |

FIG.3.

| FIG.4A. | FIG.4B. | FIG.4C. | FIG.4D. |
|---|---|---|---|
| FIG.4E. | FIG.4F. | FIG.4G. | FIG.4H. |
| FIG.4I. | FIG.4J. | FIG.4K. | FIG.4L. |
| FIG.4M. | FIG.4N. | FIG.4O. | FIG.4P. |

FIG.4.

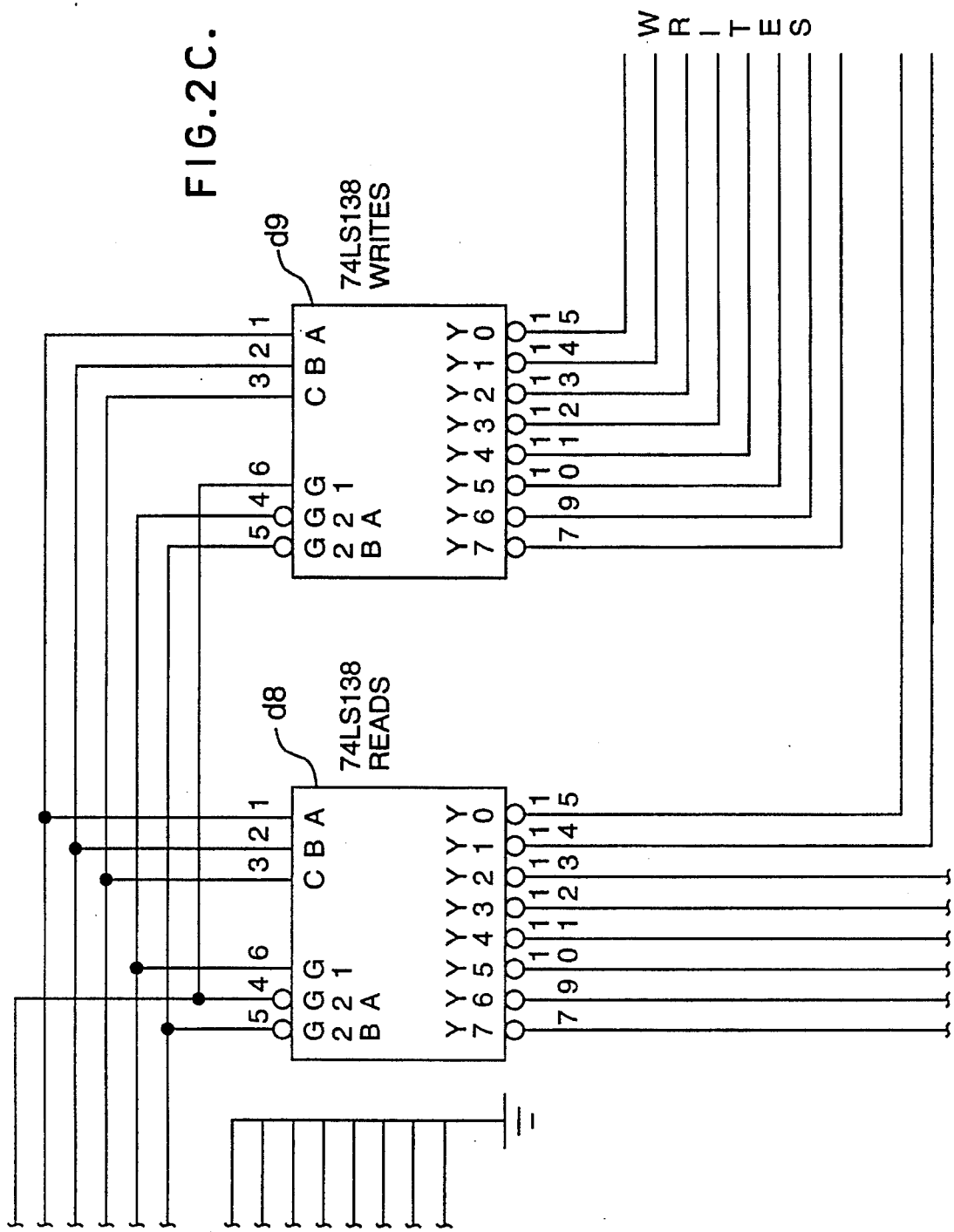

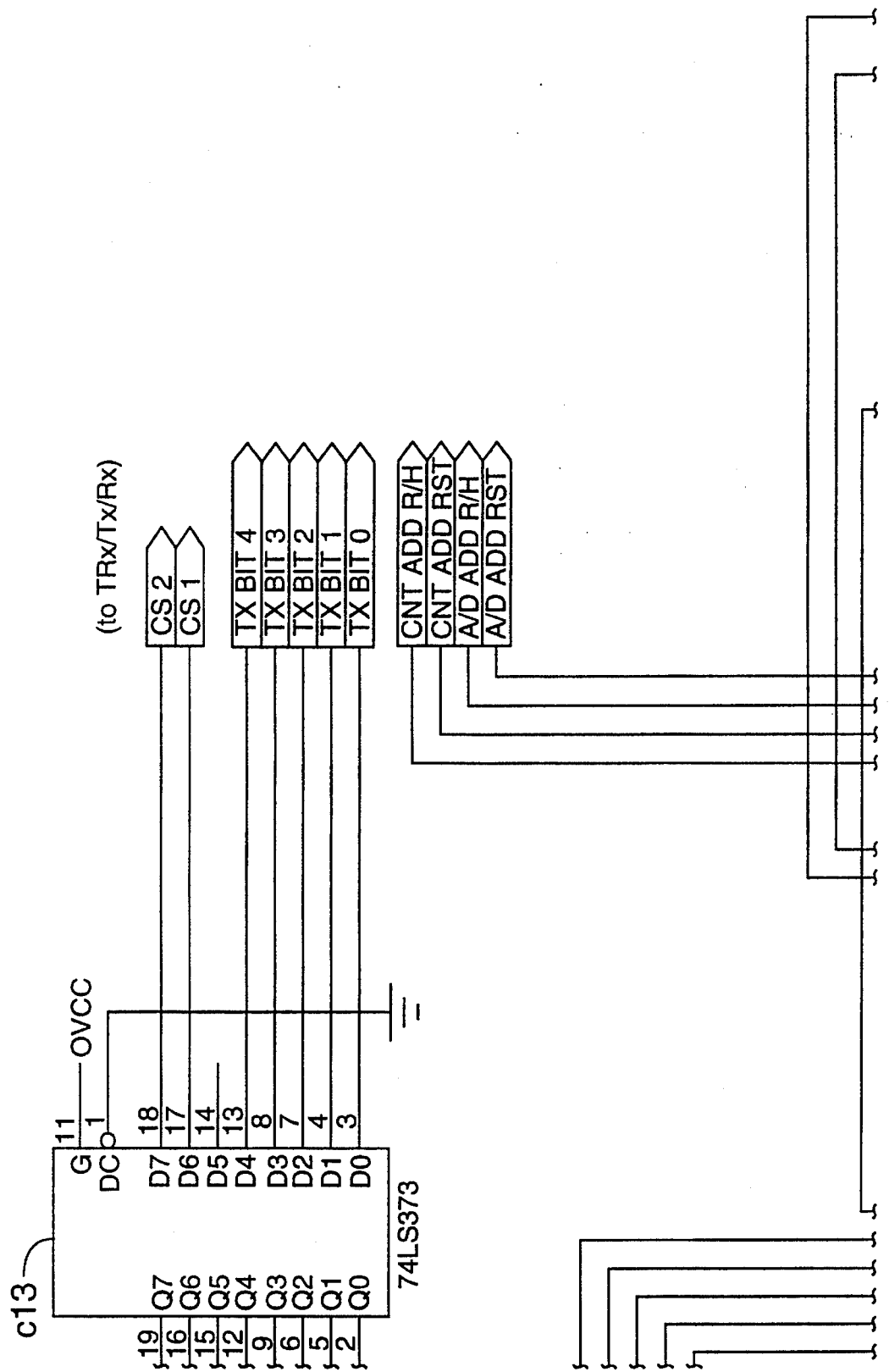

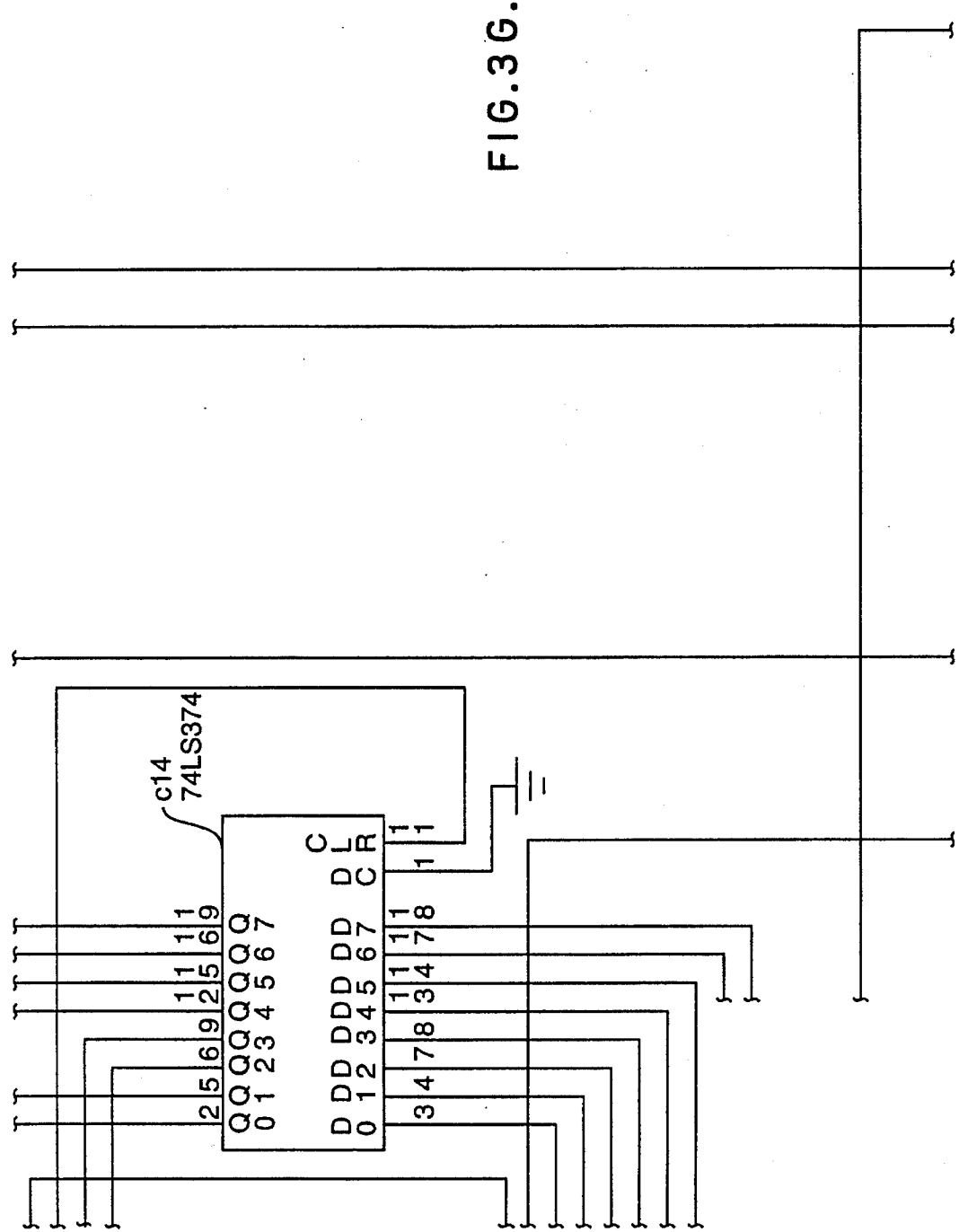

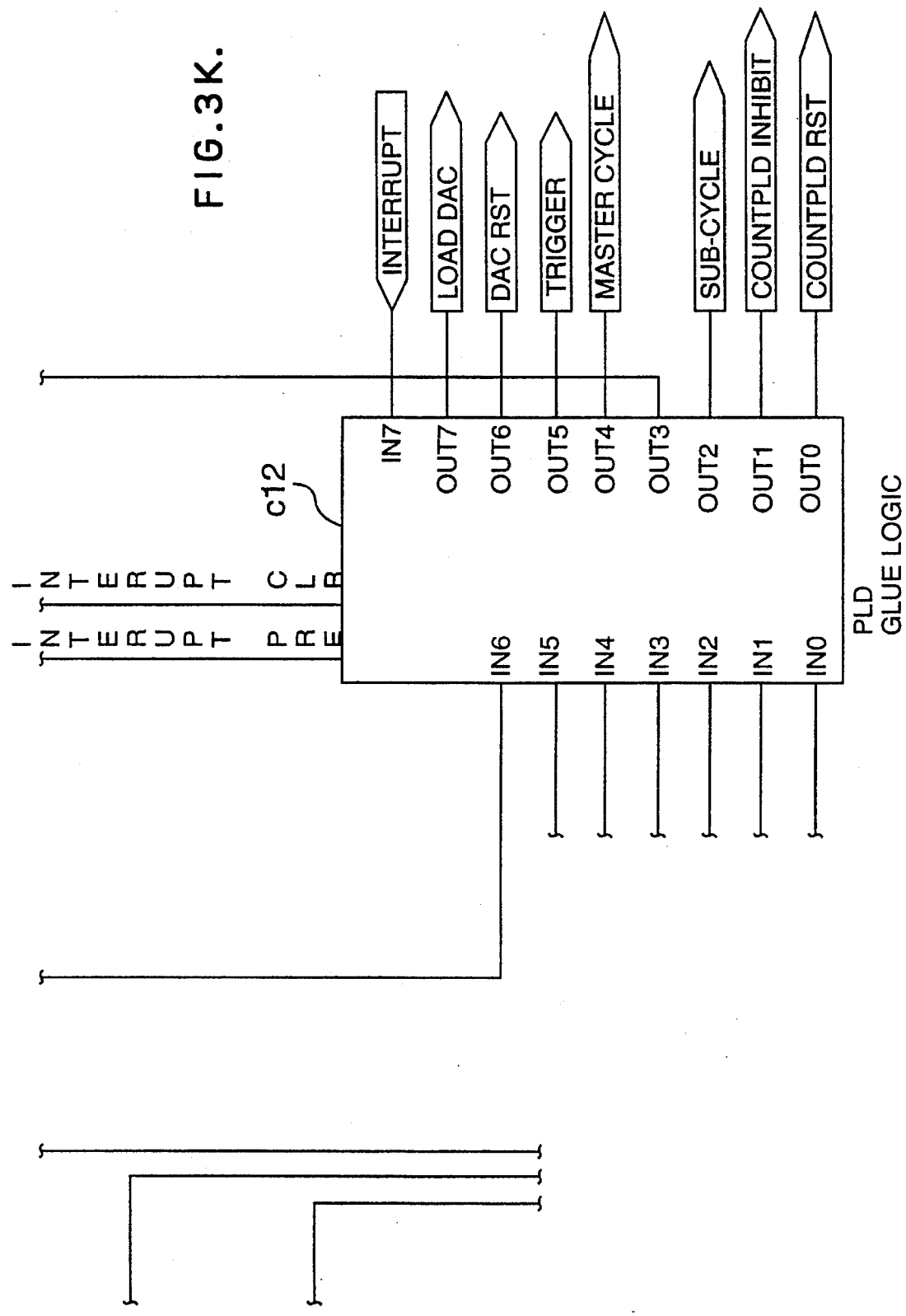

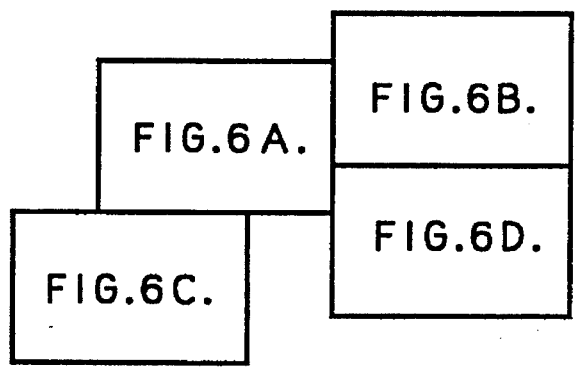
FIG.5.
FIG.6.
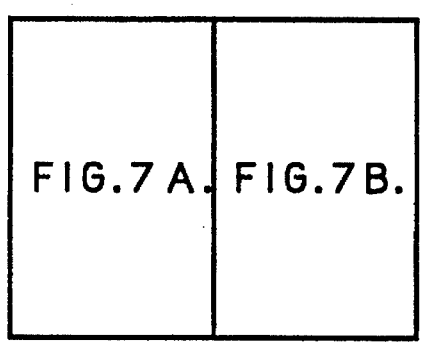
FIG.7.
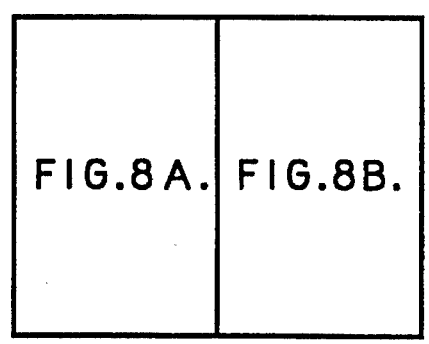
FIG.8.

THREE-DIMENSIONAL DIGITAL ULTRASOUND TRACKING SYSTEM

FIELD OF THE INVENTION

This invention relates in general to distance measuring devices, and more particularly to a software controlled digital sonomicrometer for measuring distances in two or three dimensions using multiple piezoelectric transducers.

BACKGROUND OF THE INVENTION

Using the time-of-flight principle of high frequency sound waves, it is possible to accurately measure distances within an aqueous medium. High frequency sound, or ultrasound, is defined as vibrational energy that ranges in frequency from 100 kHz to 10 MHz. The device used to obtain three dimensional measurements is known as a sonomicrometer. Typically, a sonomicrometer consists of a pair of piezoelectric transducers, (a transmitter and a receiver), that are implanted into tissue, and connected to electronic circuitry. To measure the distance between the transducers, the transmitter is electrically energized to produce ultrasound. The resulting sound wave then propagates through the medium until it is detected by the receiver.

The transmitter is energized by a high voltage spike, or impulse function lasting under a microsecond. This causes the piezoelectric crystal to oscillate at its own characteristic resonant frequency. The envelope of the transmitter signal decays rapidly with time, usually producing a train of six or more cycles that propagate away from the transmitter through the aqueous medium. The sound energy also attenuates with every interface that it encounters.

The receiver is usually a piezoelectric crystal with similar characteristics to the transmitter crystal, that detects the sound energy and begins to vibrate. This vibration produces an electronic signal in the order of millivolts, that can be amplified by appropriate receiver circuitry.

The propagation velocity of ultrasound in aqueous media is well documented. The distance travelled by a pulse of ultrasound can therefore be measured simply by recording the time delay between the instant the sound is transmitted and when it is received.

Prior art sonomicrometers suffer from a number of shortcomings which limit their utility.

Firstly, conventional sonomicrometers use analog circuitry between transmit and receive signals (e.g. phase capacitative charging circuits). The voltage representing the measured distance is then output to a strip chart recorder in analog form. This data must then be digitized for computer analysis.

Secondly, conventional systems use analog potentiometers to adjust the inhibit time and the threshold voltage that triggers the receiver circuits. This often requires the use of an oscilloscope. Each time the system is used, these settings must be manually set and adjusted in order to tune the system. This can be time consuming and annoying. As a whole, the function of the system can not be changed. The repetition frequency is fixed, regardless of the number of channels used, and the system is therefore very limited in terms both of the distances that can be measured, and the temporal precision with which the system operates.

Thirdly, conventional ultrasound tracking systems feature pairs of transmitter and receiver crystals that are energized sequentially at fixed repetition rates. As such, prior art systems lack experimental flexibility. For example, before a pair of crystals is implanted, the user must decide each crystal's function; similarly, the user must determine which distances are to be measured by which crystal pair. This can be awkward because surgery often necessitates changes during the procedure. If either of the receiver or transmitter crystals malfunctions, the distance between them cannot be measured. Critical measurements can therefore be lost after a significant amount of effort is put into setting up the surgery.

Fourthly, conventional sonomicrometer systems measure only a straight line distance between any isolated pair of crystals. Three dimensional information is therefore impossible to acquire.

Even if multiple combinations of distances could somehow be linked together, the inherently analog nature of the data would necessitate the use of additional, very complex hardware.

Finally, conventional systems use discrete elements, such as threshold capacitors and potentiometers requiring large plug-in units to increase the number of channels. The systems are very large, usually two feet wide by 18" deep, and up to 12" high. Additional hardware such as strip chart recorders must be used for visualization and subsequent processing. This can be very awkward given the space constraints at busy research institutes and hospitals.

SUMMARY OF THE INVENTION

According to the present invention, a software controlled digital sonomicrometer is provided which overcomes the problems of prior art conventional sonomicrometers and provides enhanced functionality for diverse clinical and medical research applications.

Firstly, the ultrasound tracking system of the present invention uses modern day digital electronics in conjunction with an integrated personal computer. External A/D converters are not required, as the data is acquired digitally, directly from the sensors. Due to the speed of the controlling computer, the tracking system of this invention is capable of detecting distance increments as small as 45 µm. The acquired data can be displayed on the computer screen as it is being obtained, and can be saved to the computer's storage media with a simple key stroke. After an experiment or surgical procedure, the saved data can be examined and manipulated according to the user's specifications.

Secondly, according to the system of the present invention, virtually every function is digitally controlled, and therefore very flexible. To begin, a set-up menu is generated which allows the user to select which crystals are active as well as the function of each channel. Next, a data display program permits the parameters of the transducer to be customized for specific applications. For example, if very few channels are being used, the repetition frequency can be increased so that data can be acquired at several KHz. On the other hand, if the system is being used in vitro, where persistent echoes from a container vessel may present a problem, the repetition frequency can be reduced to allow the echoes to attenuate between successive measurements.

The duration of the power delivered to the crystals can be reduced for precision work or increased if greater distances are required to be measured. The duration of the delay required to overcome electromagnetic interference between crystal leads is adjustable by means of a variable inhibit feature. Additionally, the number of samples displayed and stored in any given data save is variable according to the length of time that a user's protocol demands. Finally, the resolution of the displayed information is variable in conjunction with the degree of motion of the measured specimen. All of these functions are controlled digitally by means of custom designed digital cards or modules discussed in greater detail below, which, in turn, are software controlled.

Additional customized software is included in the system of the present invention for post processing and visualizing the acquired data. In these routines, stray data points can be easily removed, three point filters can be applied for smoothing, level shifts can remove areas of discontinuity, channels can be derived, beat analyses can be performed, and automatic minimum/maximum level sensing can be applied. Finally, routines can be provided that allow animated data points in a Cartesian coordinate system while providing volumetric and position information.

The ultrasound tracking system of the present invention overcomes the limitation of prior art crystal pairs. The present system can work with as many as 32 individual transducers that can be energized sequentially at very high repetition rates, thereby giving the impression that several distances are being measured instantaneously. In reality, the distances are measured in sequence, but since the delay time between successive measurements is never greater than five milliseconds, the measurements occur virtually simultaneously for most biological applications.

Additionally, the system of the present invention provides the option of combining the transmitter and receiver circuitry into one transceiver. This provides a researcher with the freedom to affix an array of crystals to a test object (e.g. catheter, needle, probe, etc,) and then decide which crystals are to function as transmitters and which are to function as receivers. Moreover, this type of configuration does not need to be limited strictly to transmitter-receiver pairs. By using dedicated transceivers, the duty cycle between implanted crystals can automatically alternate between transmit and receive modes, so that every possible combination of distances between a group of crystals can be determined. This type of application is particularly useful for studies which require redundancy of measurement, as well as for establishing in vivo reference frames from which to base three dimensional tracking.

The ultrasonic tracking system of the present invention is configurable into a true 3-D mode. In this configuration four or more transceivers are implanted within an object (i.e. specimen) in which distances are to be measured, thereby serving as a mobile reference frame. Multiple transmitters are then attached to the specimen at various locations. Since any three transceivers can send and receive signals, they essentially create an x,y plane. The fourth transceiver is then used to determine the z coordinate of the surrounding crystals by determining if the active transmitter lies above or below the reference plane.

Finally, because the system of the present invention uses modern day integrated circuitry and custom programmed logic chips, it is physically much smaller than prior art units. A large part of the system of the present invention is implemented within the user P.C. (personal computer). The entire unit is composed of three digital computer cards that plug directly into a standard AT computer mother board. A single cable connection connects the controlling computer and the discrete peripheral transmitter/receiver/transceiver unit. This convenient set-up drastically reduces the amount of experimental space required over prior art conventional units

BRIEF DESCRIPTION OF THE DRAWINGS

A detailed description of the preferred embodiment is provided herein below with reference to the following drawings, in which:

FIG. 2, comprising FIGS. 2A, 2B, 2C and 2D, is a schematic diagram of a computer interface architecture used on all digital cards or modules of the preferred embodiment;

FIG. 3, comprising FIGS. 3A, 3B, 3C, 3D, 3E, 3F, 3G, 3H, 3I, 3J, 3K, 3L, 3M, 3N, 3O, 3P and 3Q is a schematic diagram of a controller card architecture according to the preferred embodiment;

FIG. 4, comprising FIGS. 4A, 4B, 4C, 4D, 4E, 4F, 4G, 4H, 4I, 4J, 4K, 4L, 4M, 4N, 4O and 4P is a schematic diagram of a counter card architecture according to the preferred embodiment;

FIG. 5, comprising

FIG. 6, comprising

FIG. 7, comprising

FIG. 8, comprising

DETAILED DESCRIPTION OF THE PREFERRED EMBODIMENT

Figure 1:
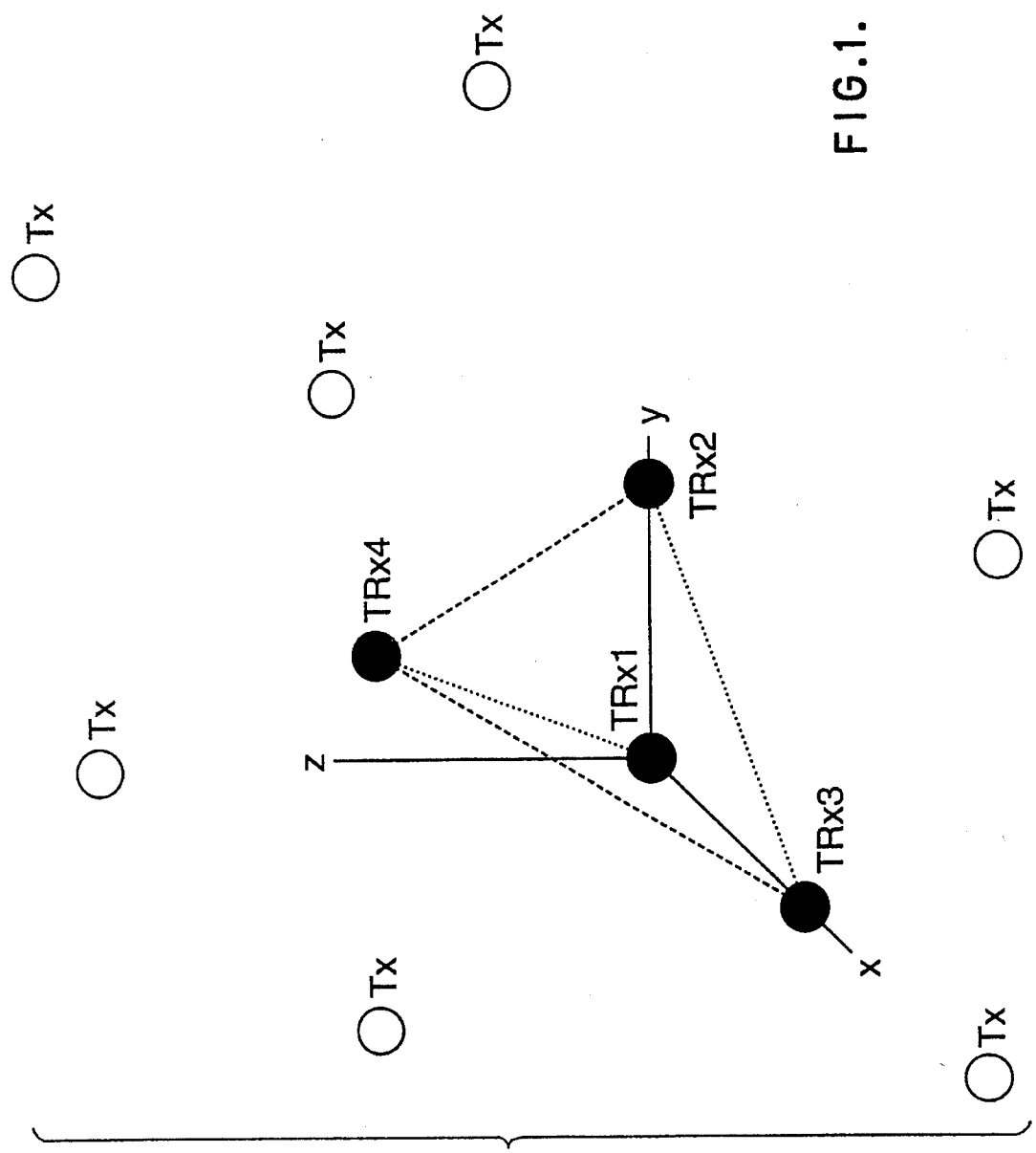
FIG. 1 is a schematic representation of four transducers in three dimensional space, for tracking and triangulating the three dimensional positions of each transducer, in accordance with the present invention.

As discussed above, the ultrasonic tracking system of the present invention utilizes a plurality of transceivers, each of which can be programmed to operate as a transmitter or a receiver. By utilizing four or more transceivers, full three dimensional measurement capability is provided, as shown in FIG. 1. Any three transceivers (TRx1, TRx2 and TRx3) lay in a plane (i.e. the x,y plane). The fourth transceiver (TRx4) may then be used to determine the z coordinates of the surrounding crystals (i.e. multiple crystals Tx) by determining if an active one of the transmitter crystals lies above or below the reference plane established by transceivers TRx1, TRx2 and TRx3. Each of the many transmitters (Tx) attached to the specimens are sequentially fired, while all reference transceivers record the received signals. Since the distance from each transmitter to the reference plane created by the transceivers is known, the relative x,y,z, coordinates of the transmitters can be determined. This is done in real time on a personal computer (P.C.) with the use of triangulation. This method of networking the crystals is unique to the system of the present invention, and permits the user to trace the three-dimensional motion of an object under investigation. Obviously, the greater the number of transmitters, the better is the reconstruction.

Specific applications of the digital ultrasound tracking system which utilize three dimensional tracking and triangulation, are discussed in greater detail below.

As indicated above, the ultrasonic tracking system according to the present invention is preferably fully integrated into the standard AT-style computer motherboard found in modern PCs.

The three digital cards which comprise the majority of the hardware for the present invention, perform specific, modular functions in the overall operation of the unit. As such, each card is provided with a proper system interface structure in order to be compatible with the ISA architecture of the controlling processor.

Figure 2A:
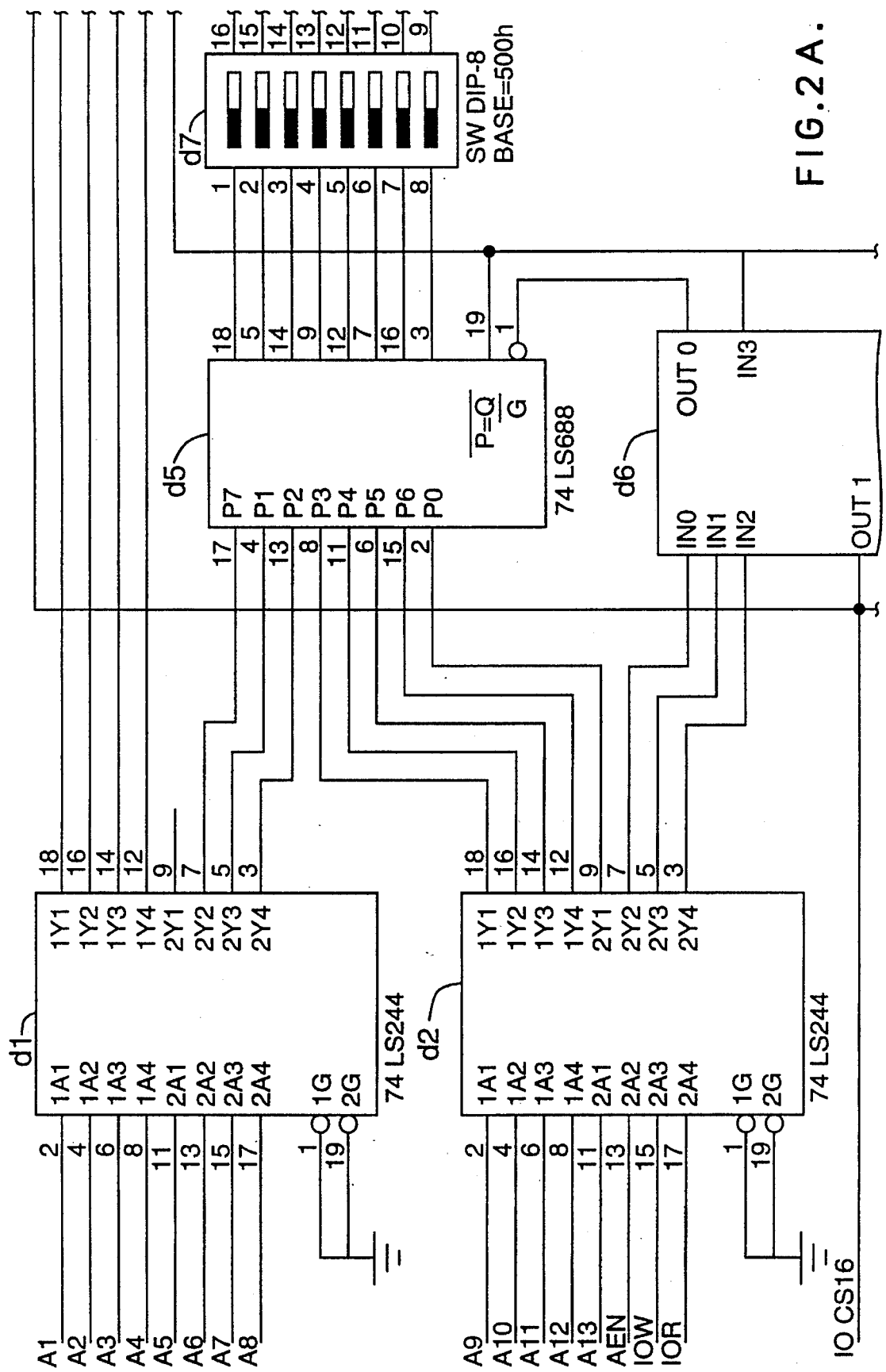
Figure 2B:
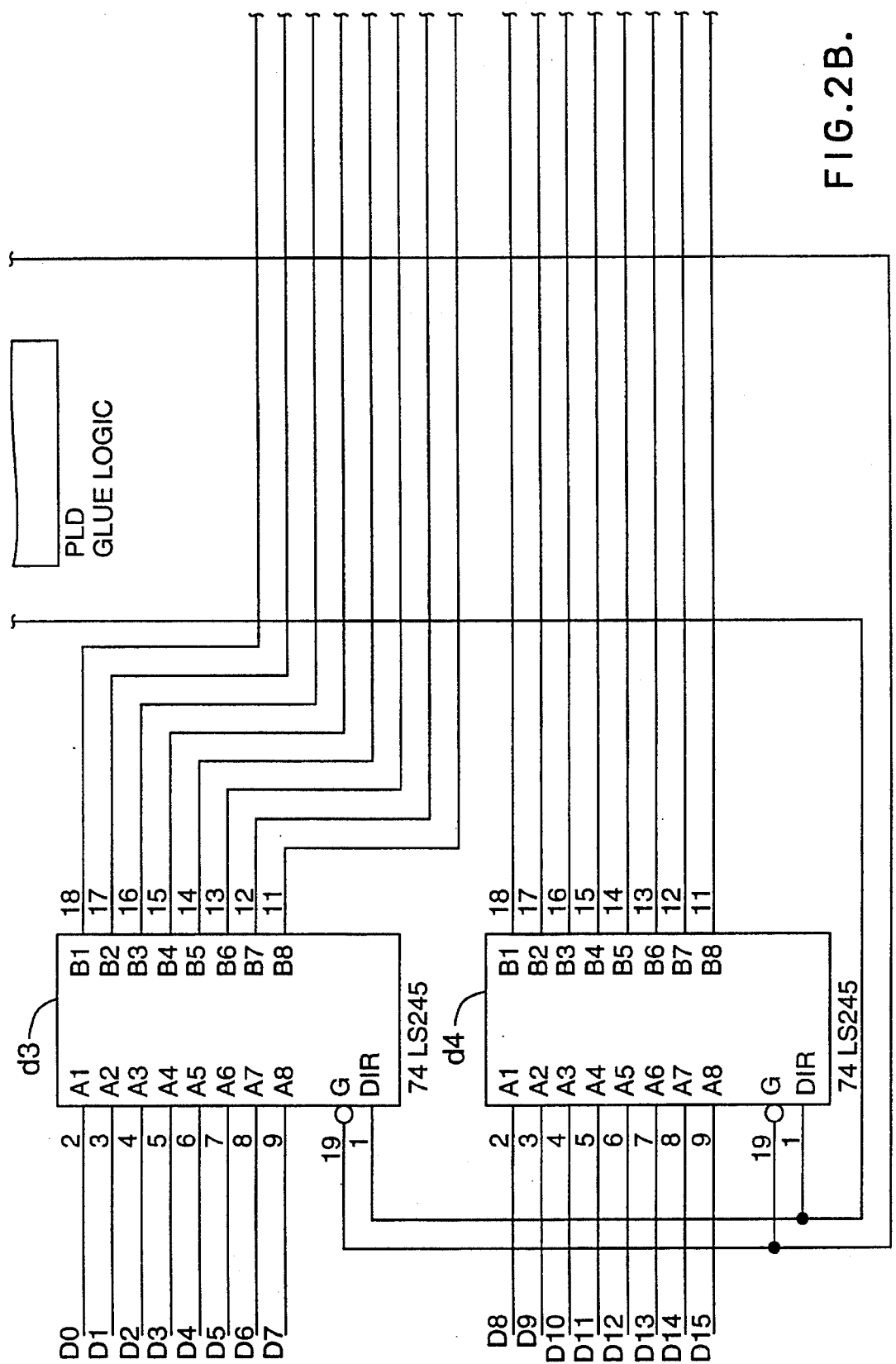
Figure 2D:
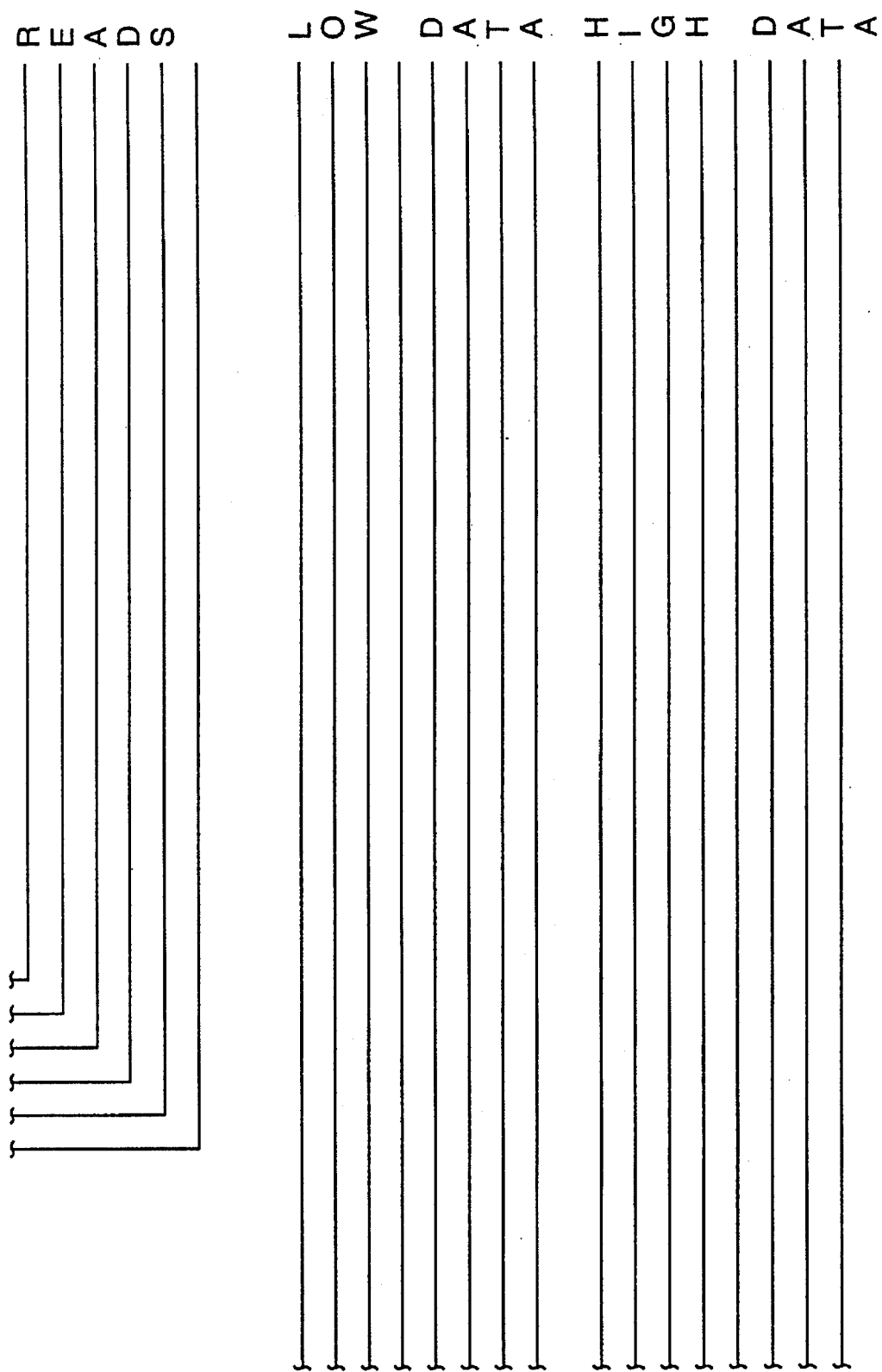
Figure 3A:
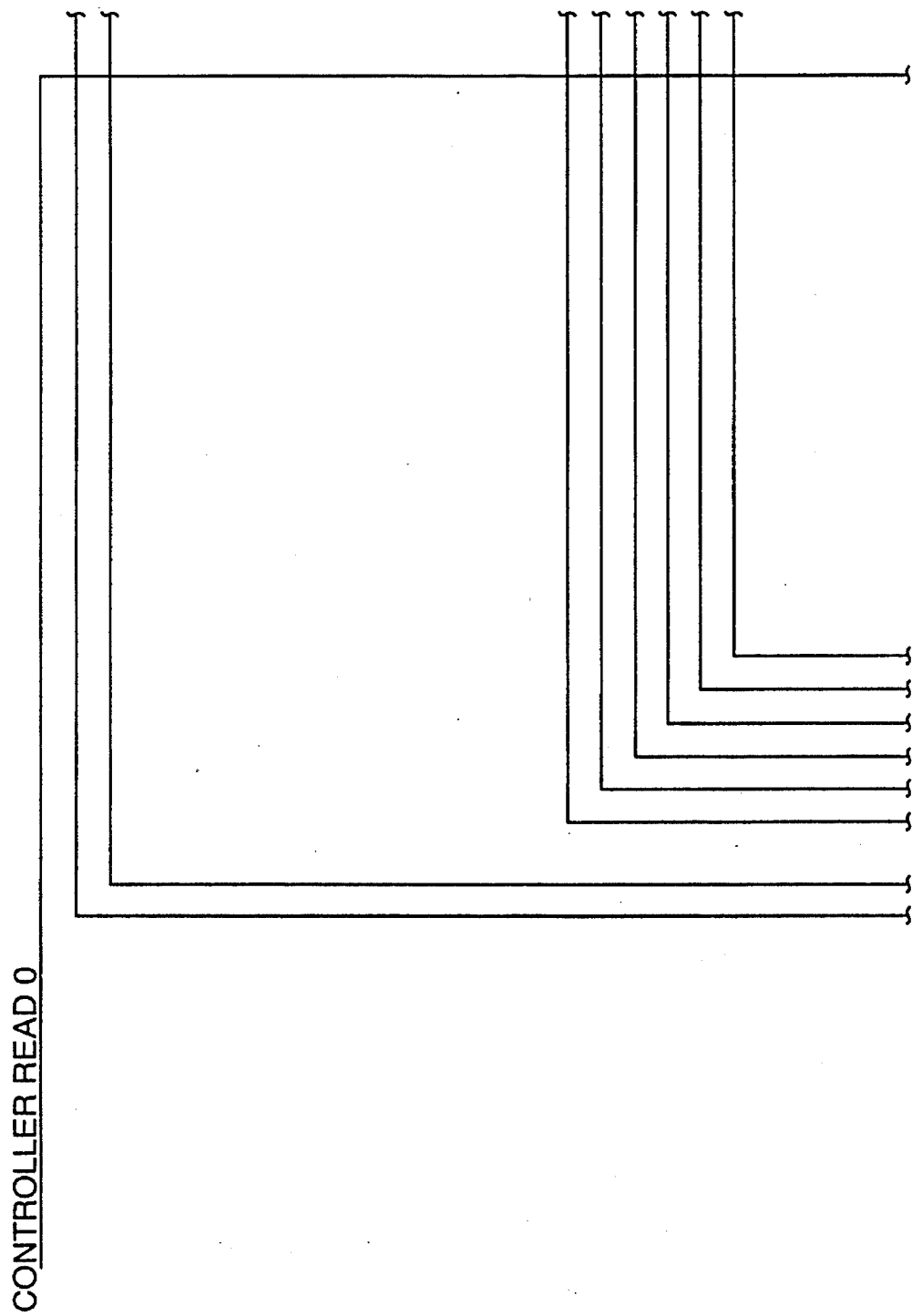
Figure 3B:
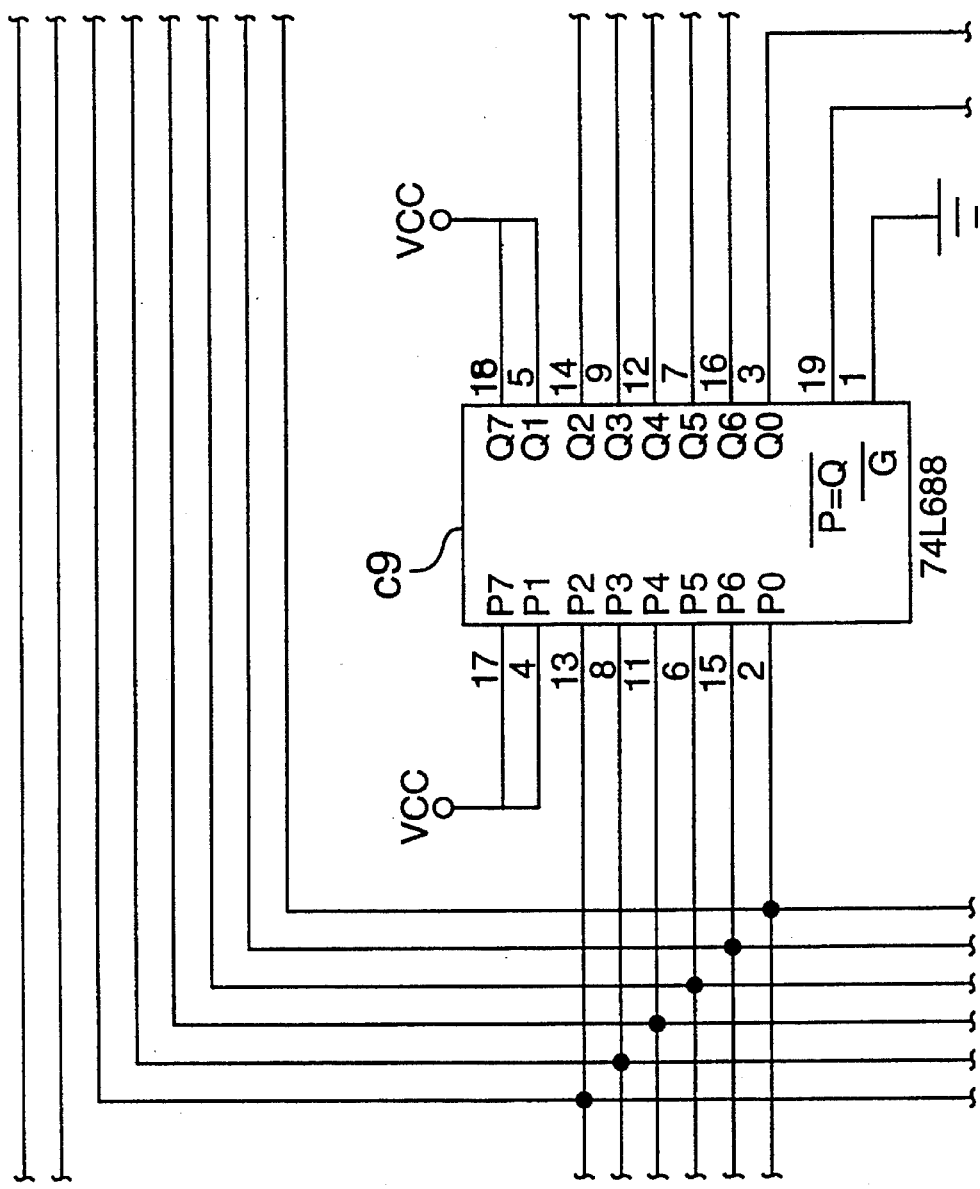
Figure 3D:
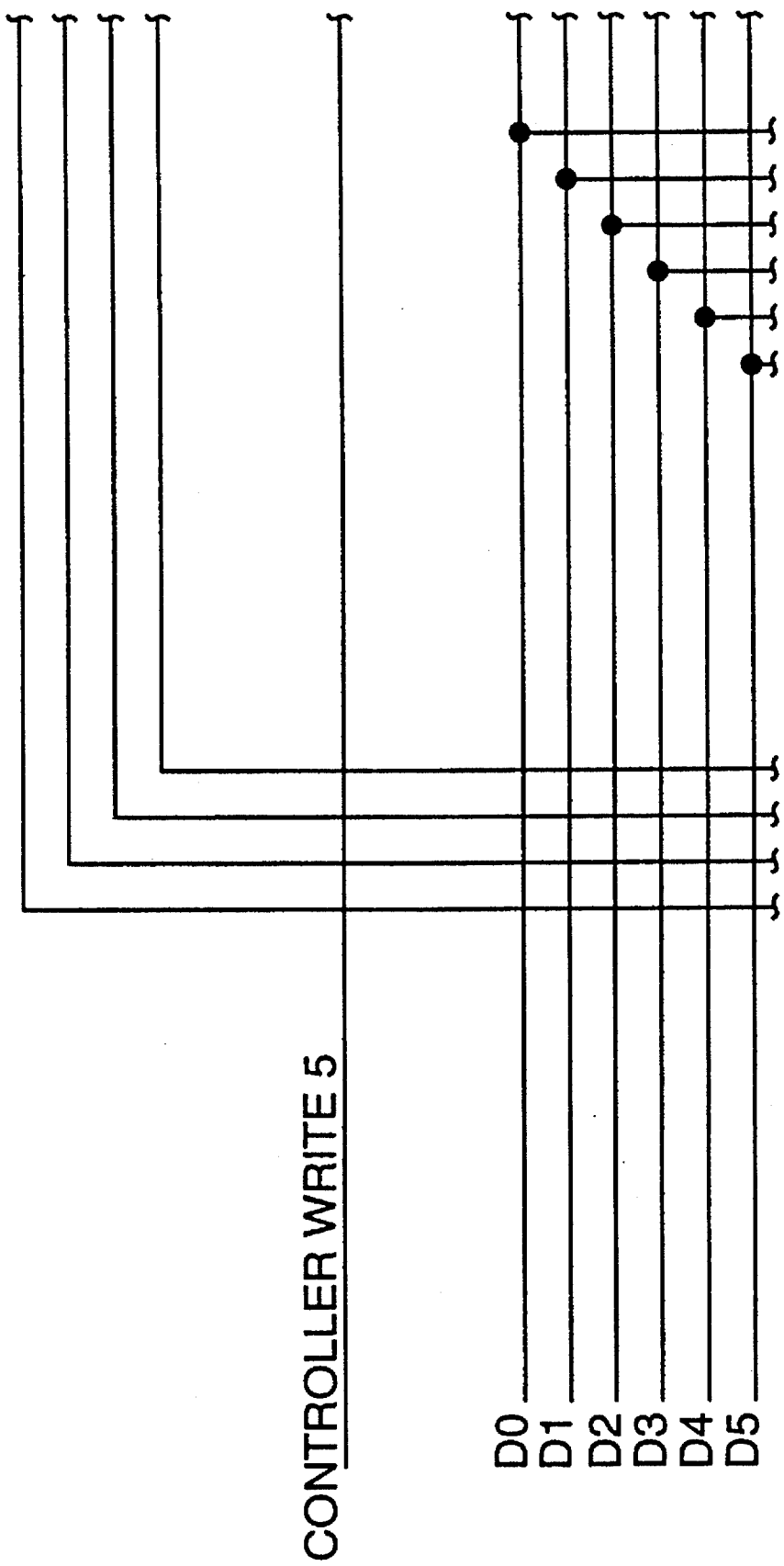
Figure 3E:
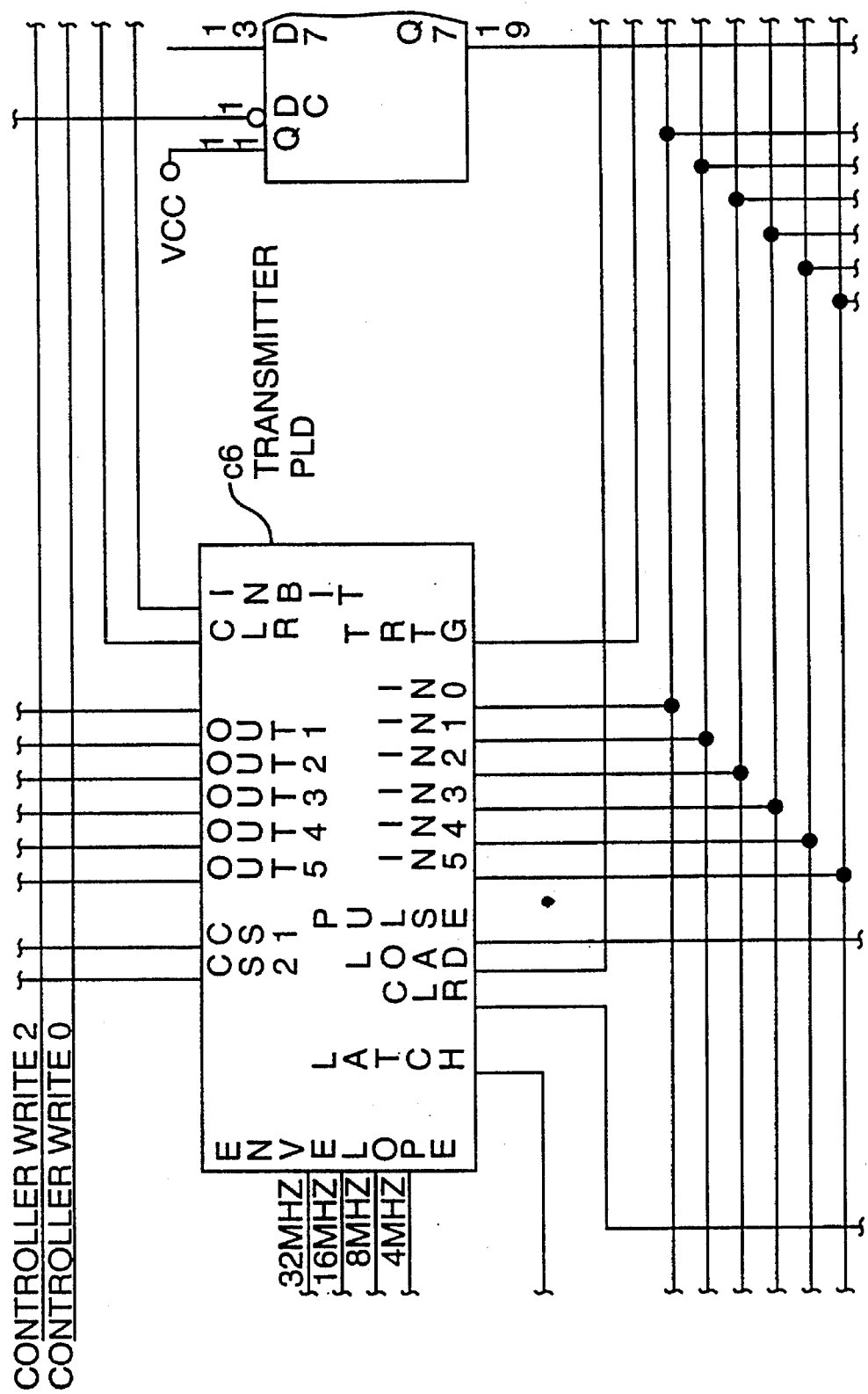
Figure 3F:
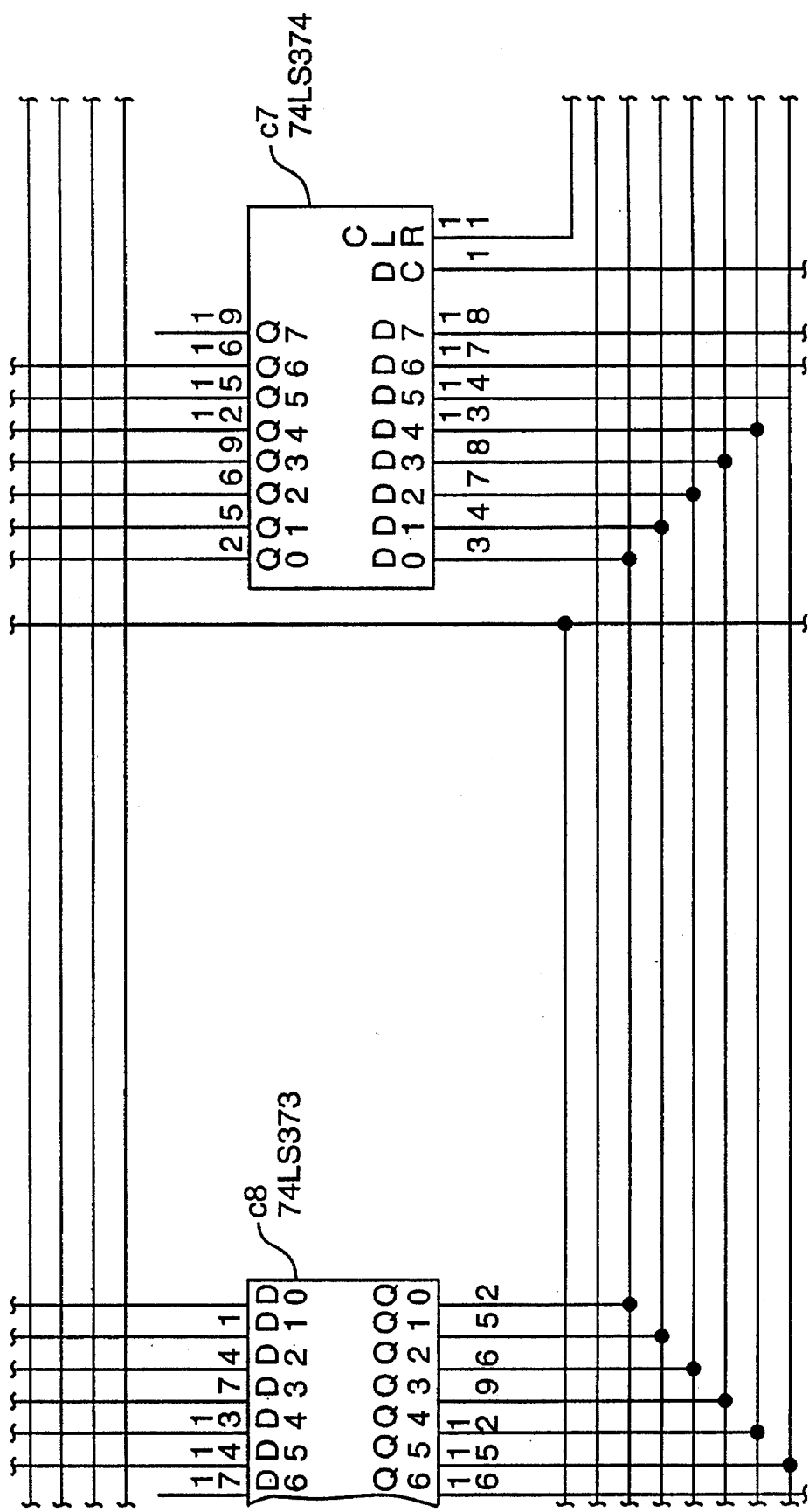
Figure 3H:
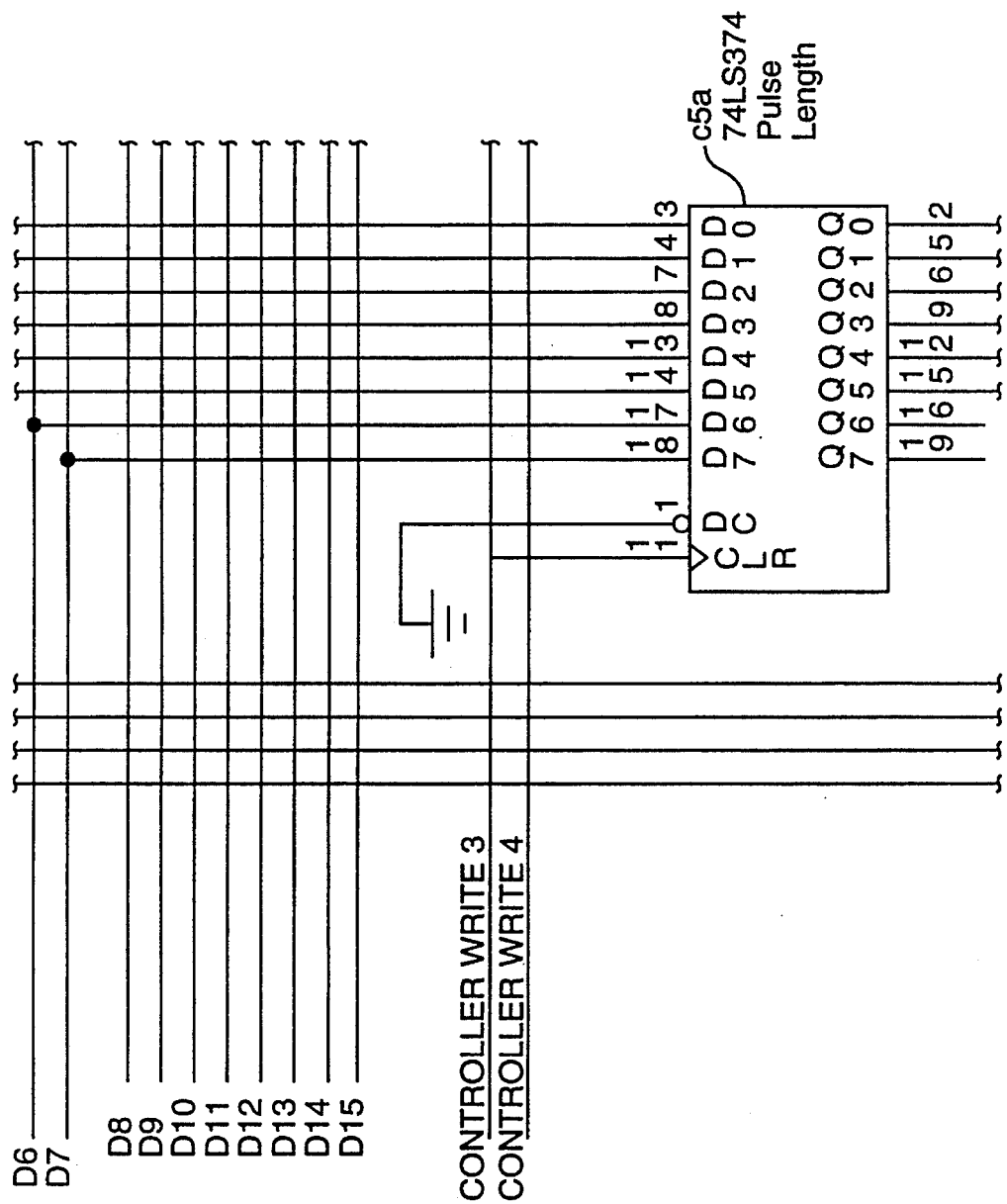
Figure 3I:
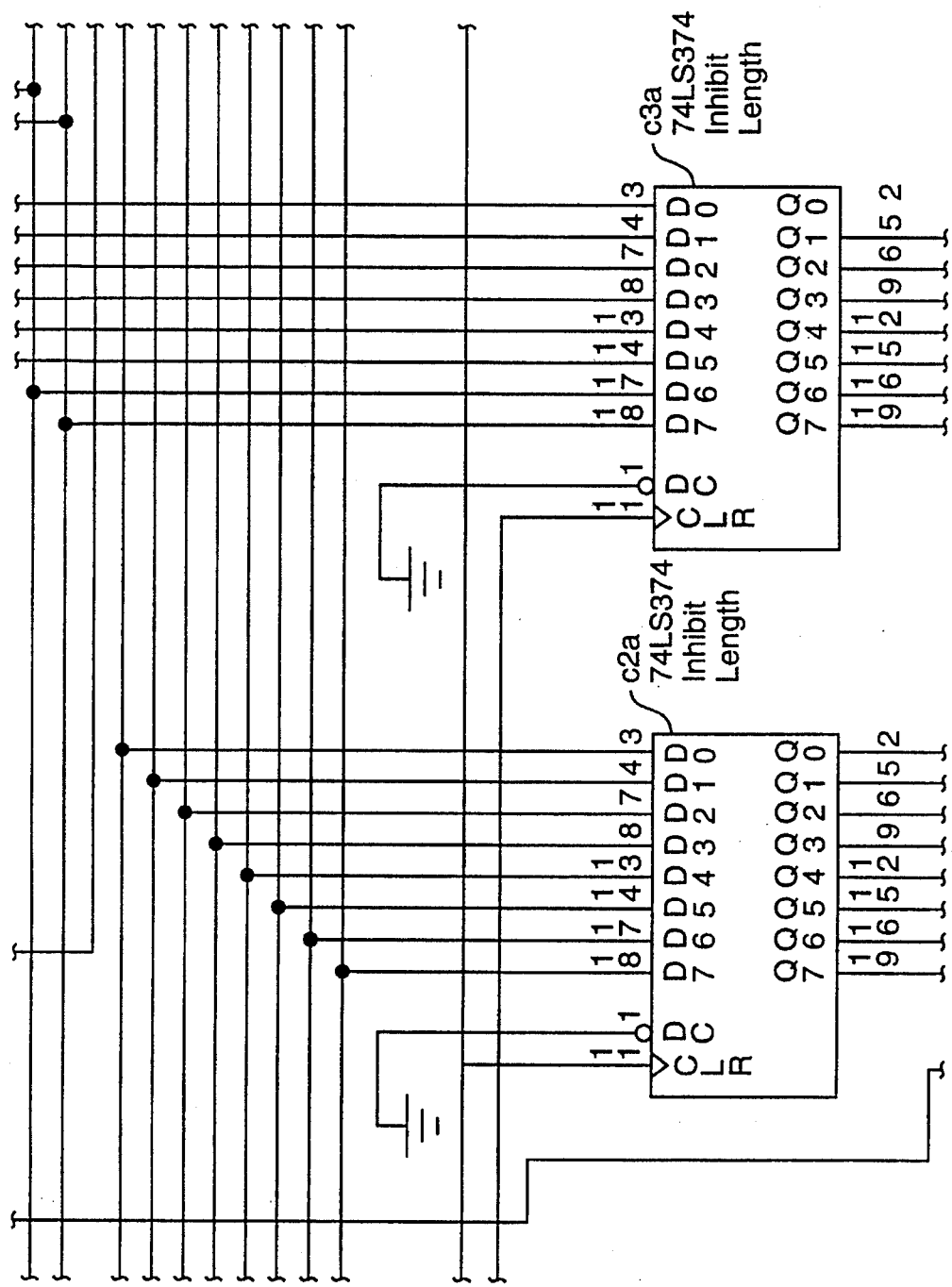
Figure 3J:
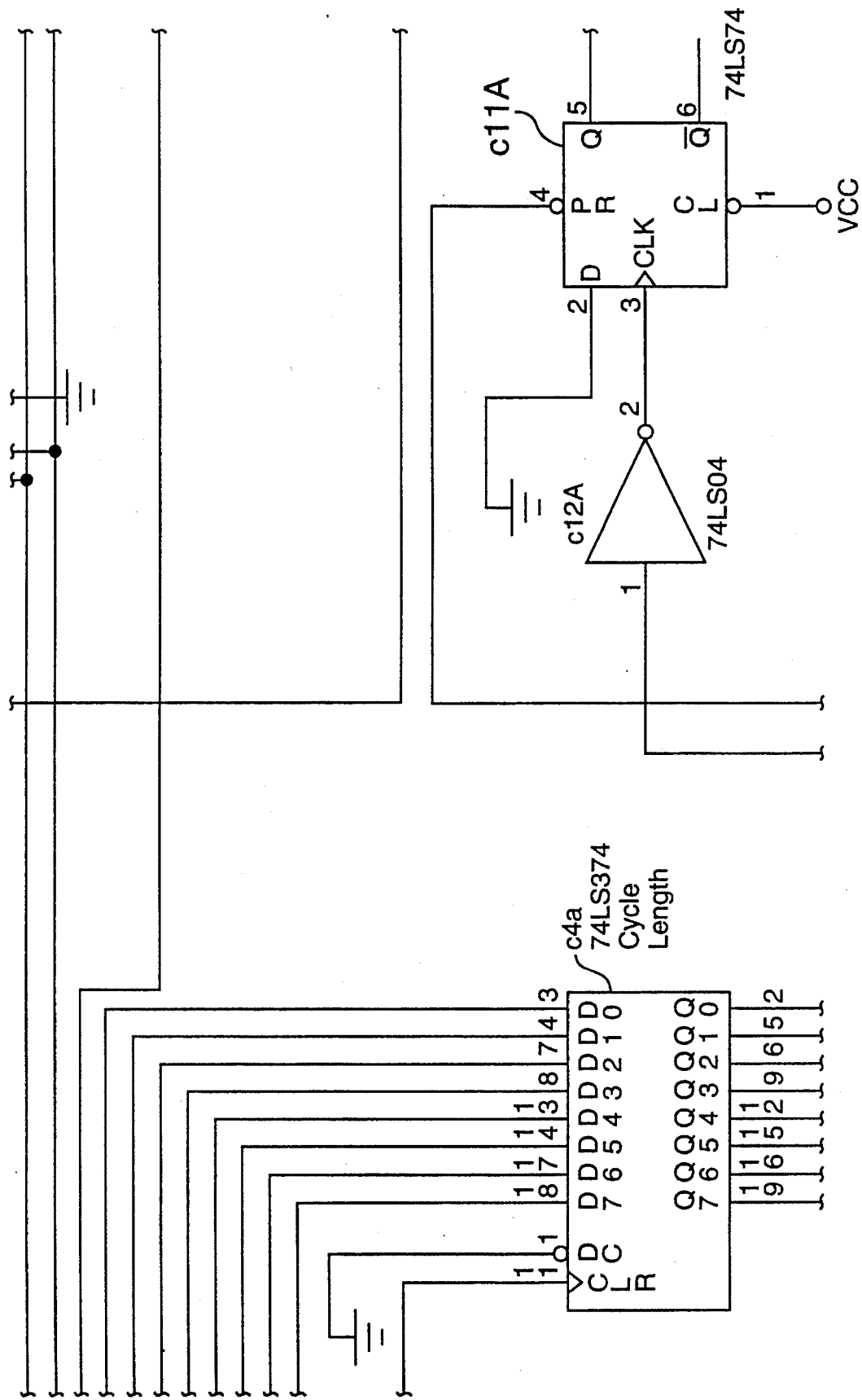
Figure 3L:
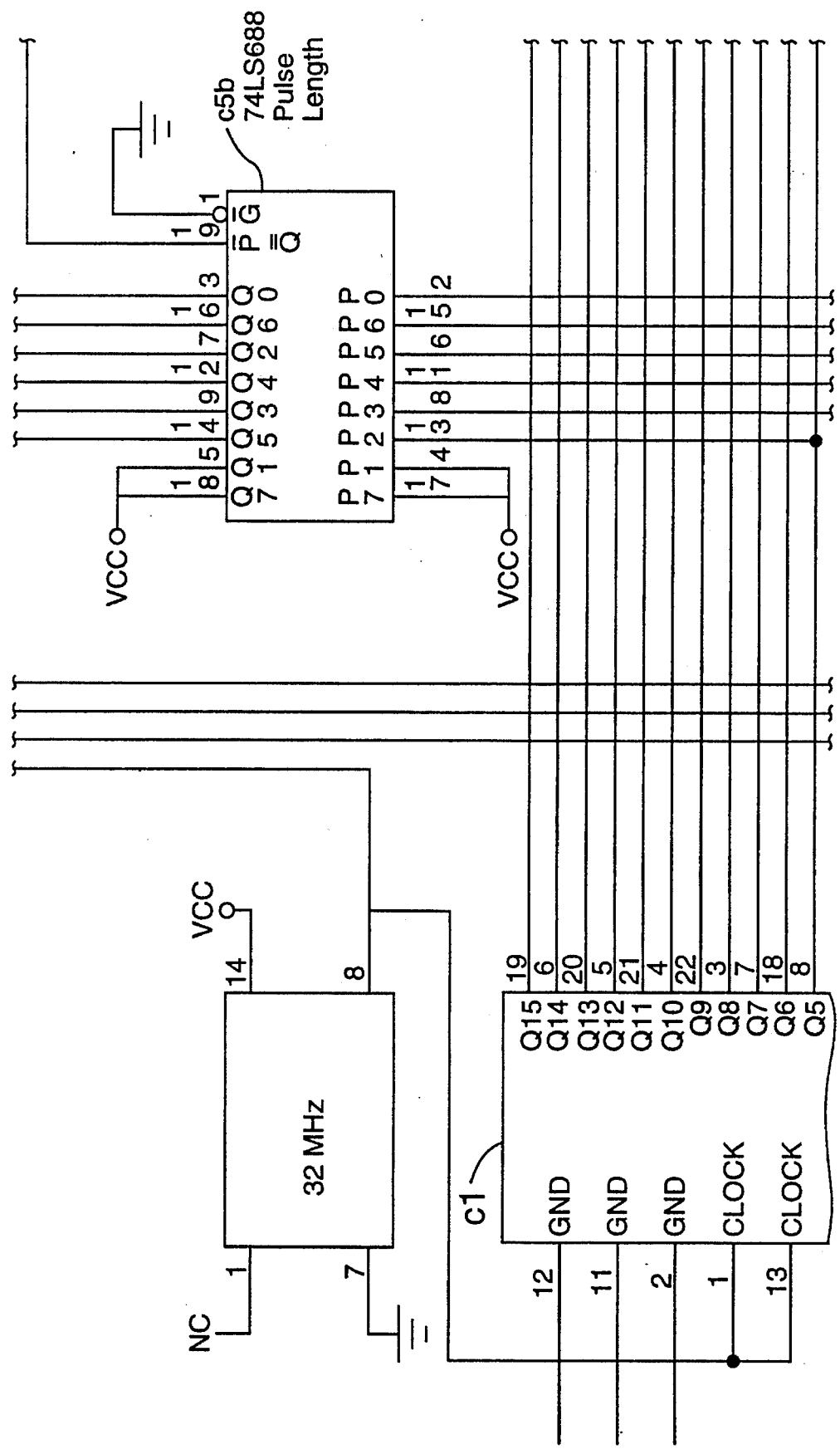
Figure 3M:
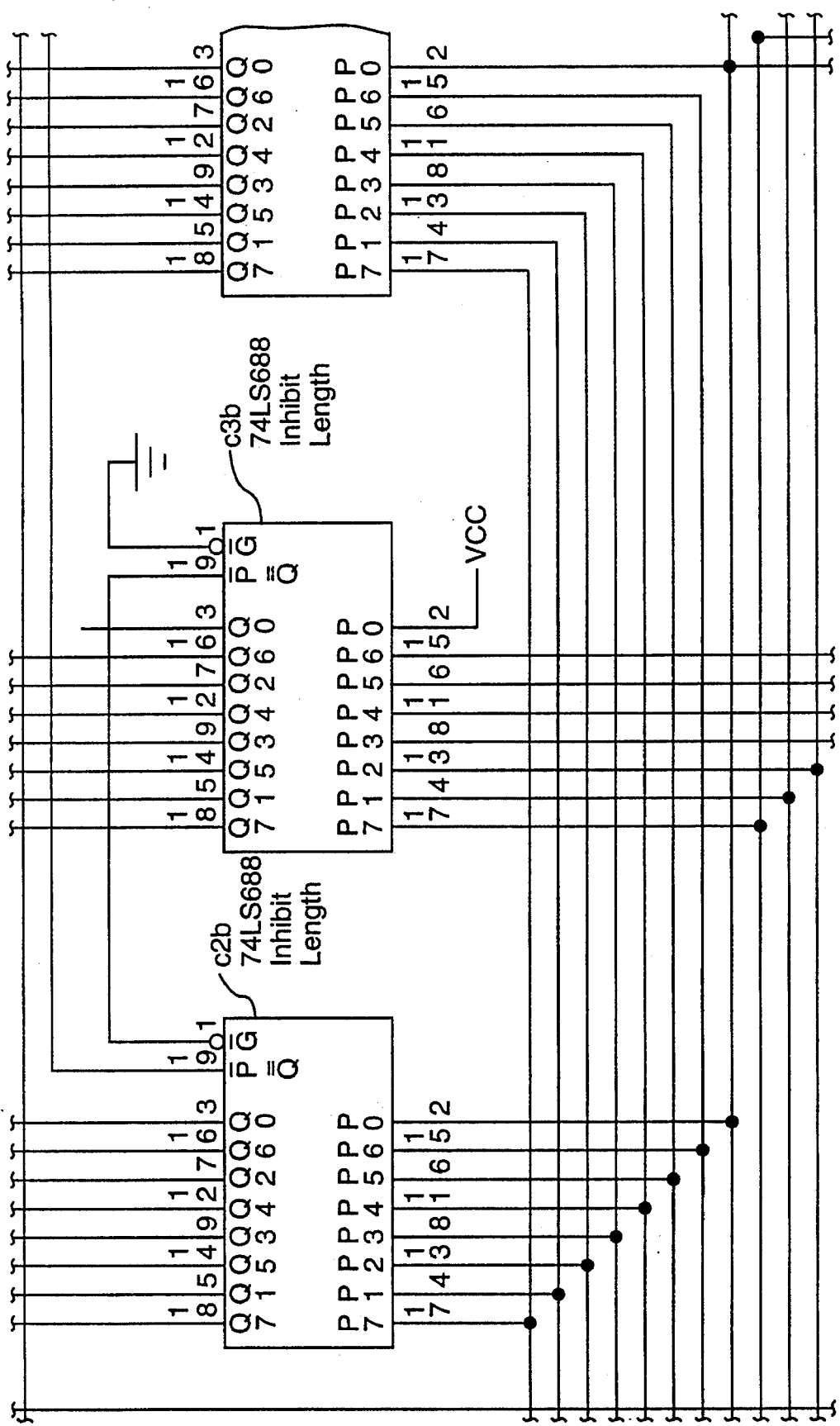
Figure 3N:
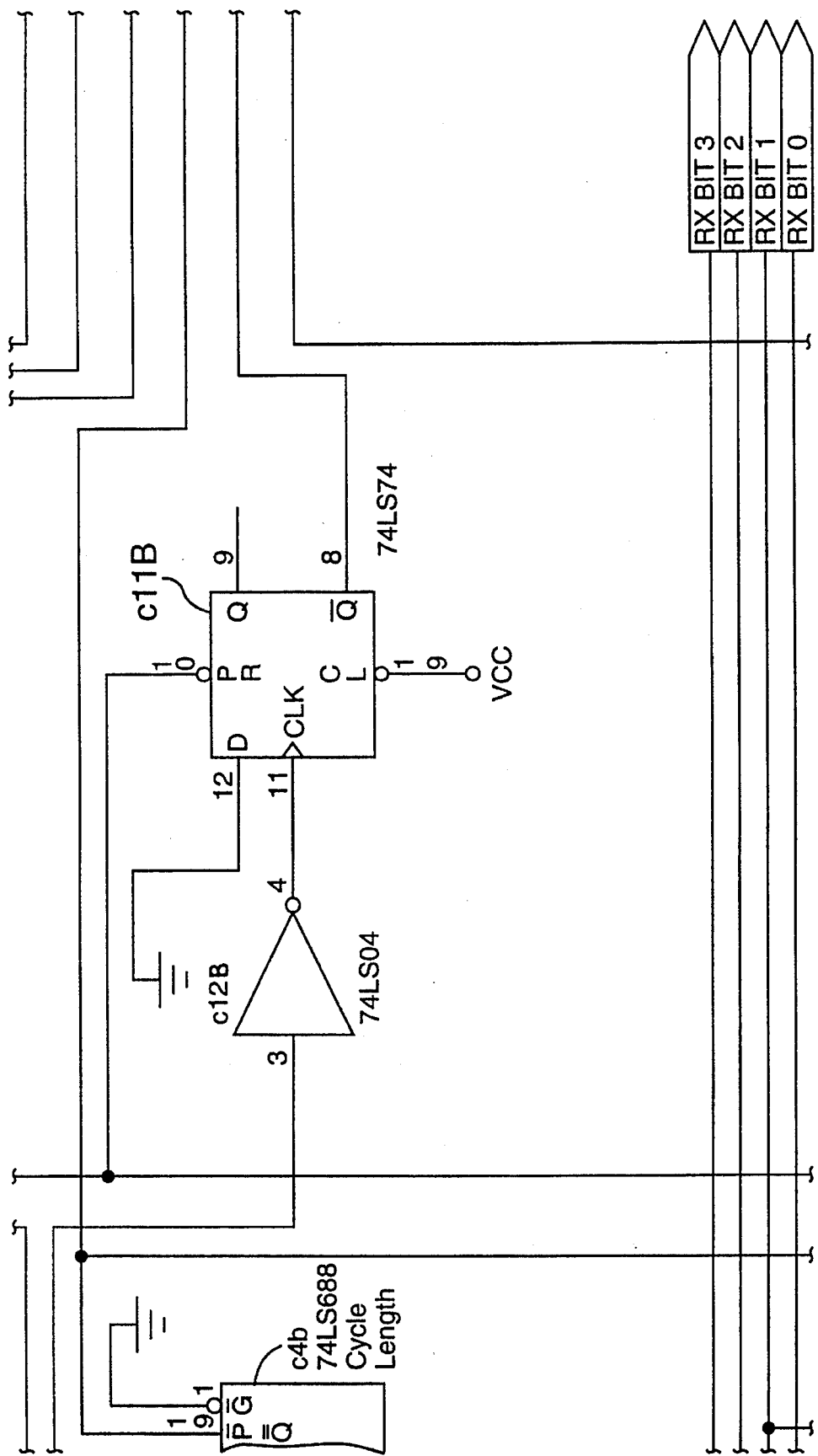
Figure 3O:
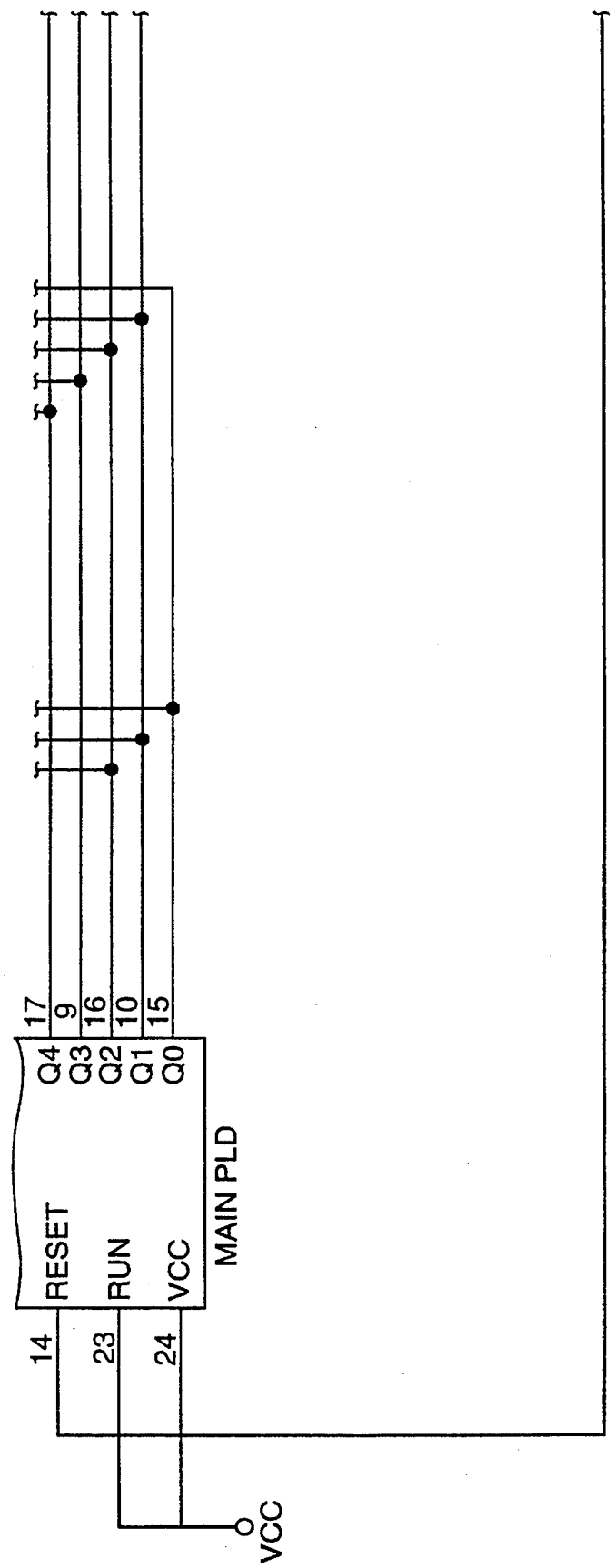
Figure 3P:
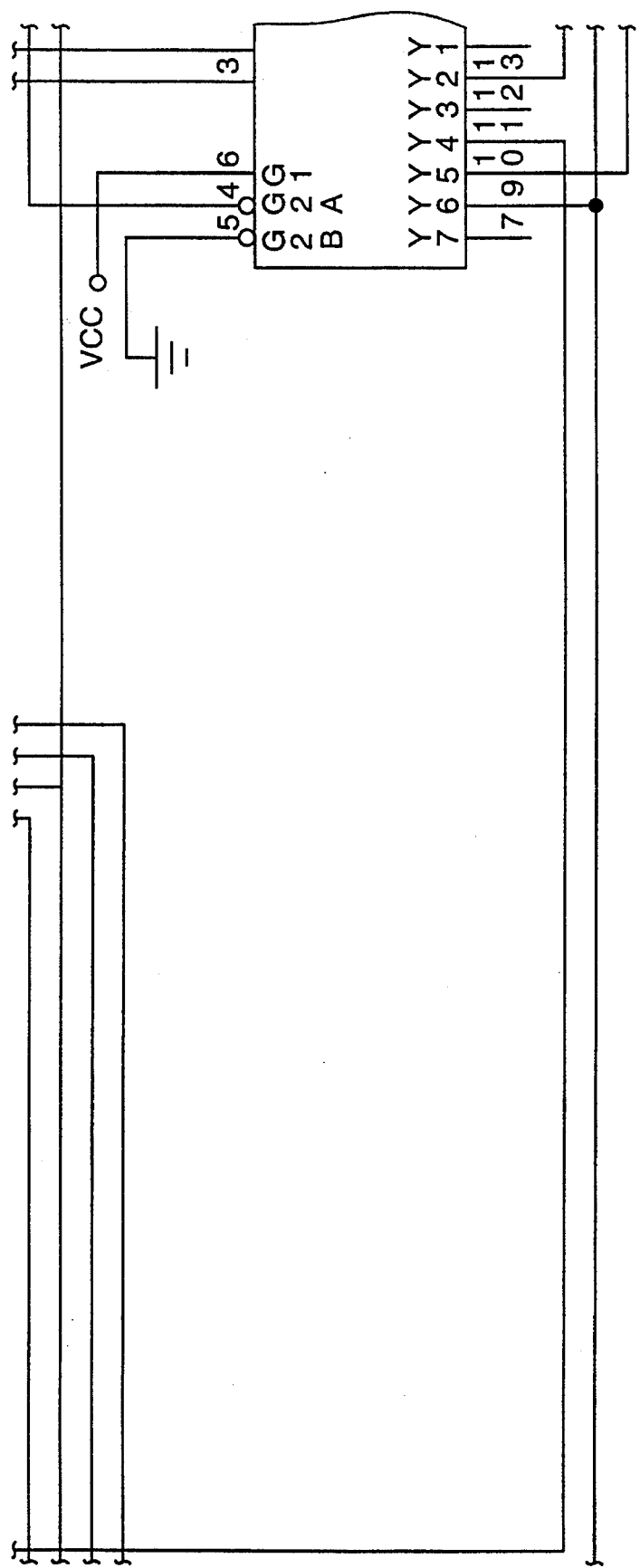
Figure 3Q:
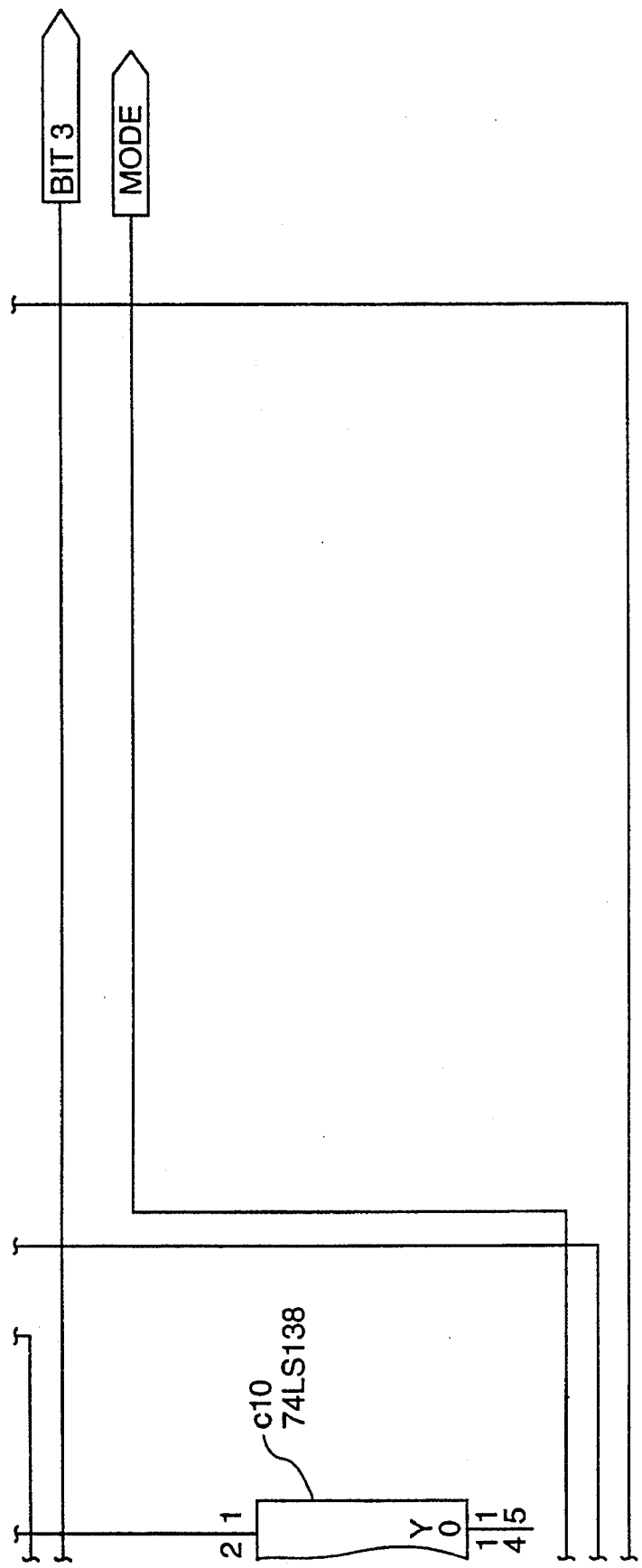
Figure 4A:
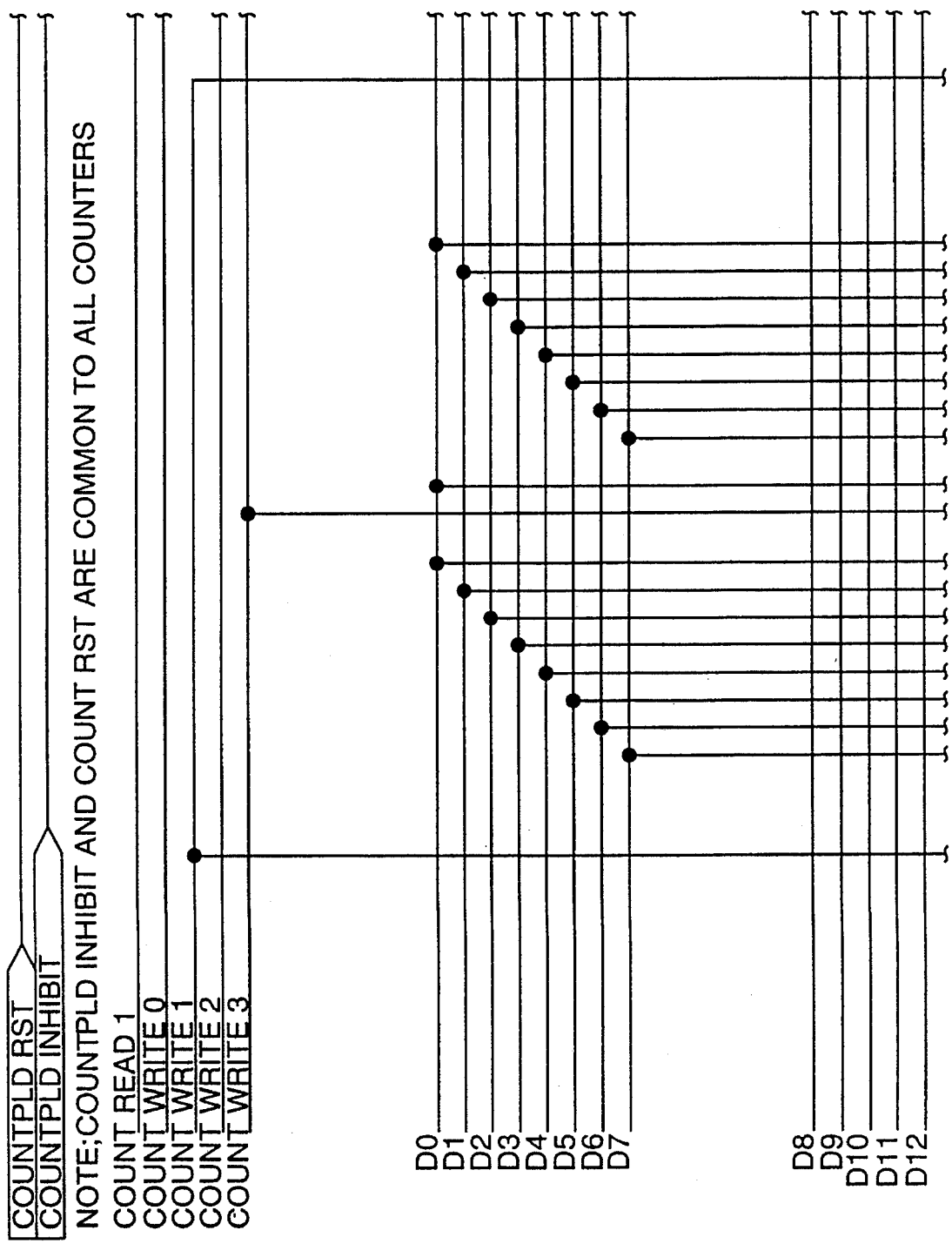
Figure 4B:
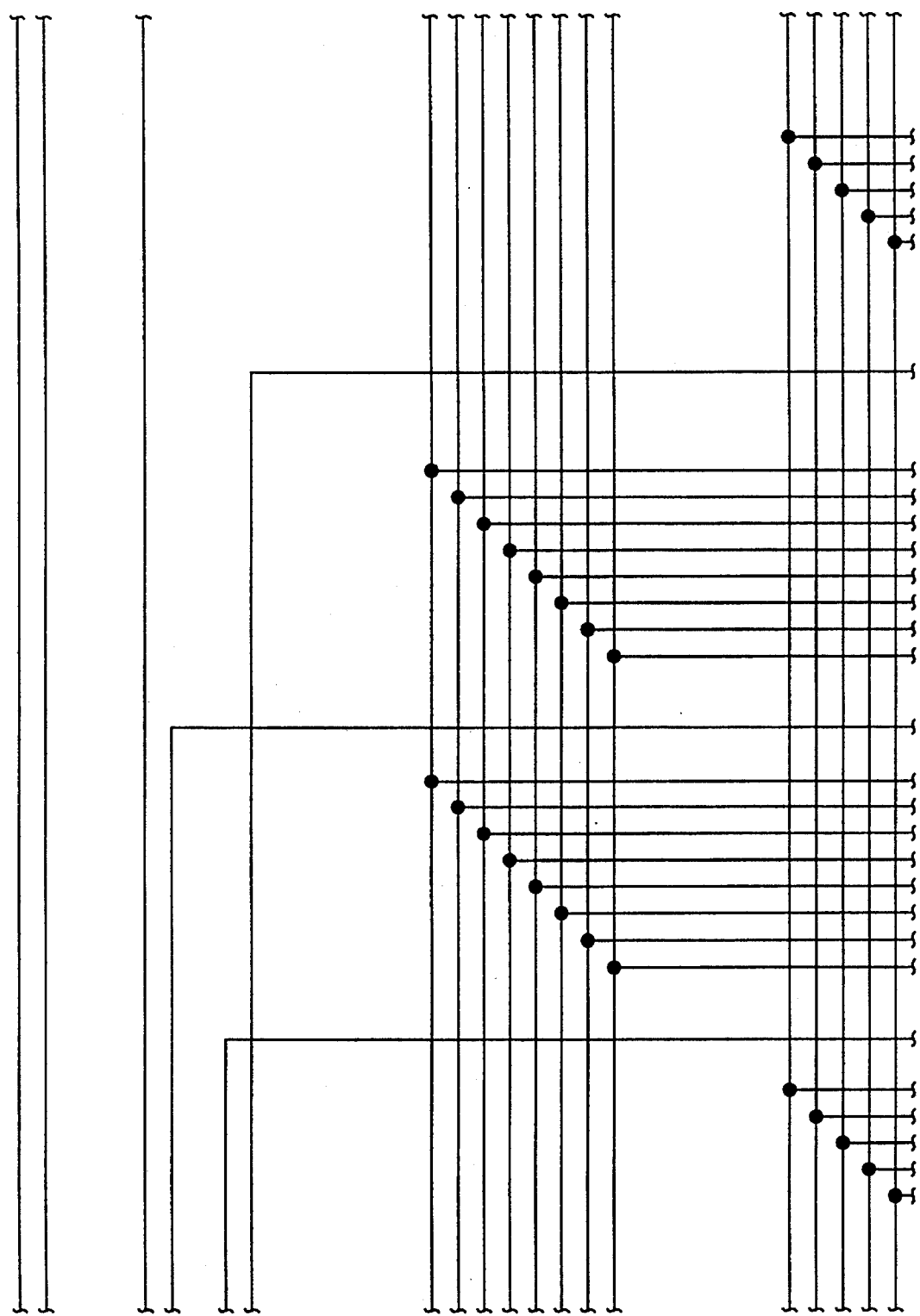
Figure 4C:
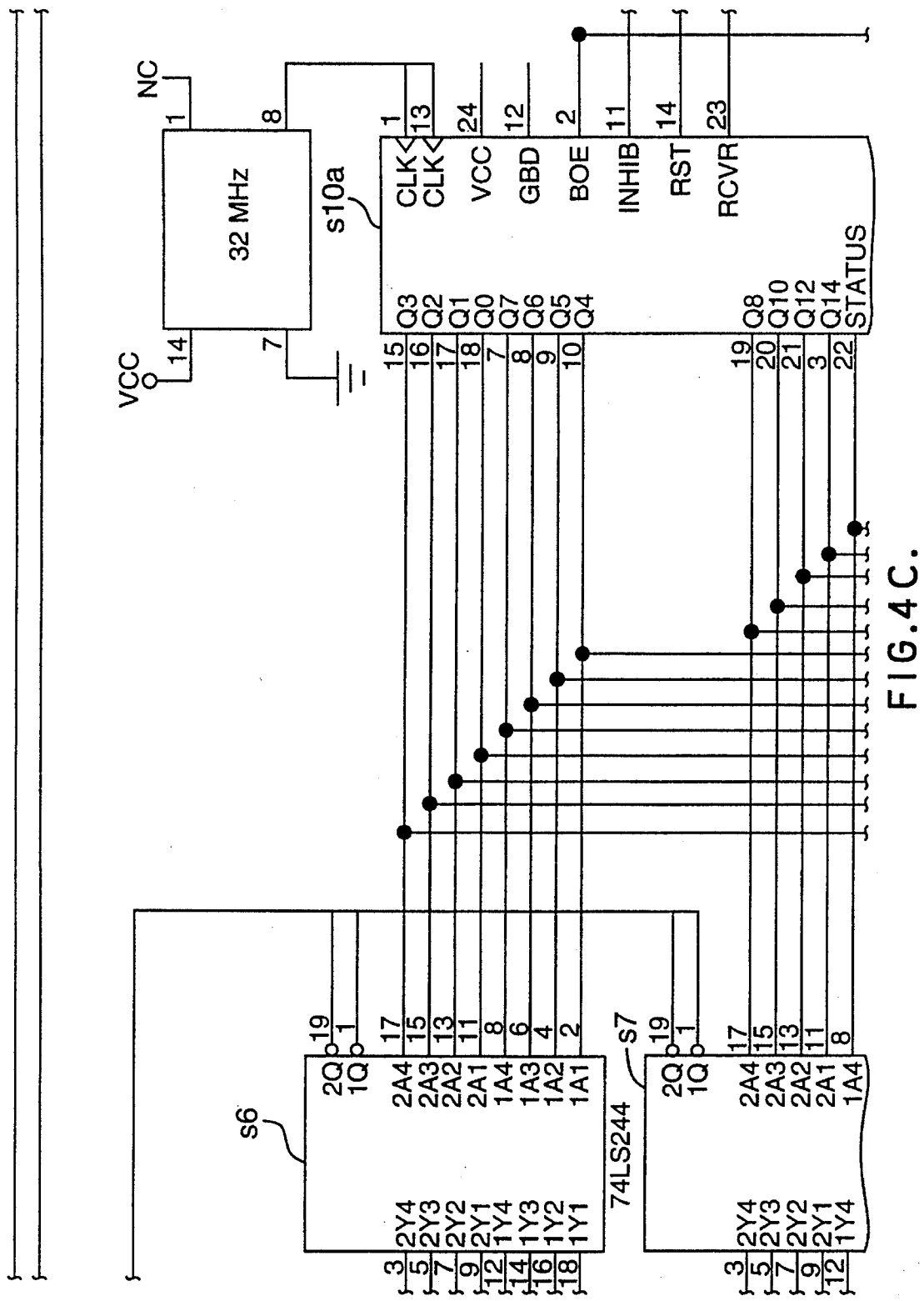
Figure 4D:
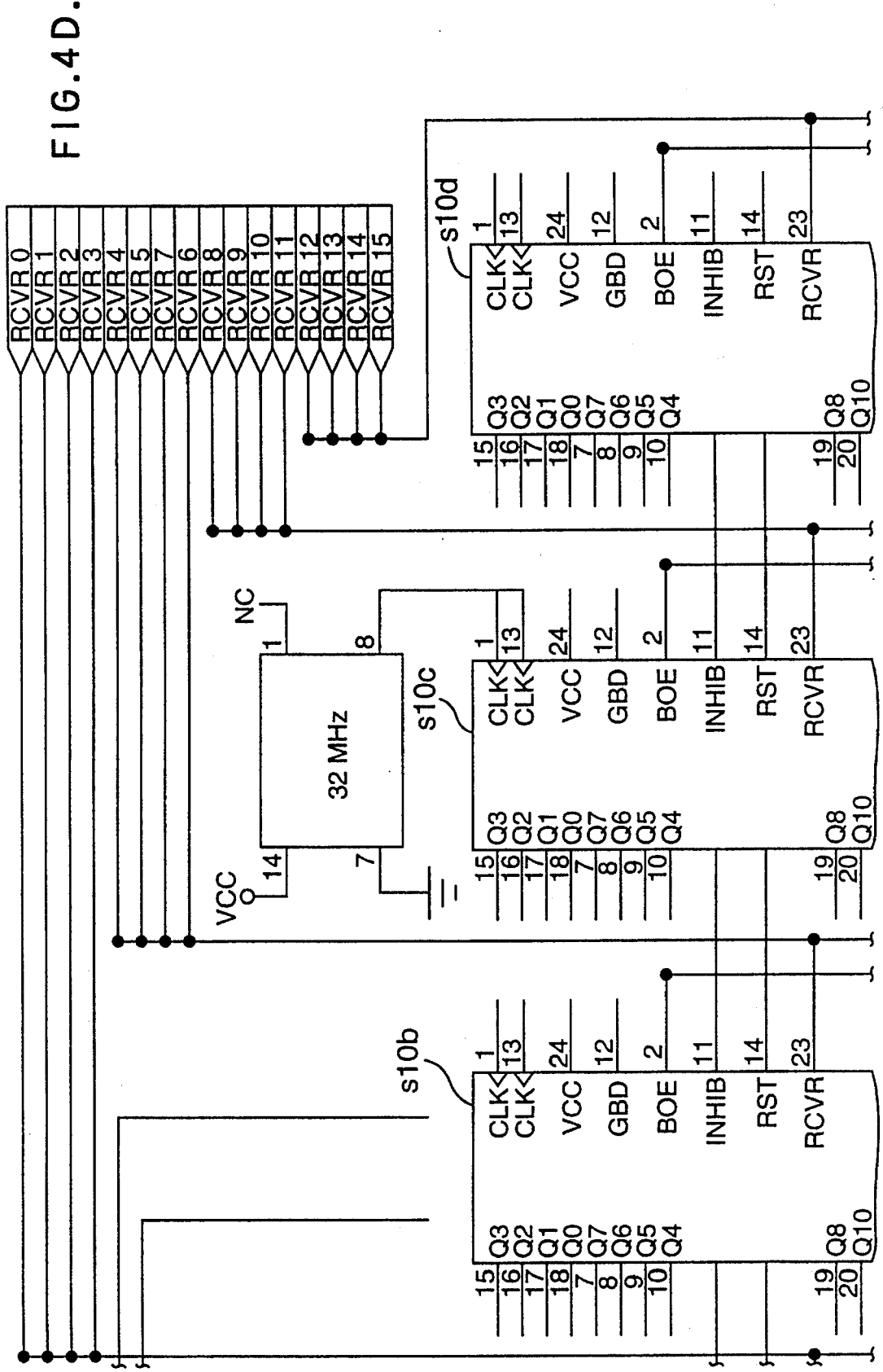
Figure 4E:
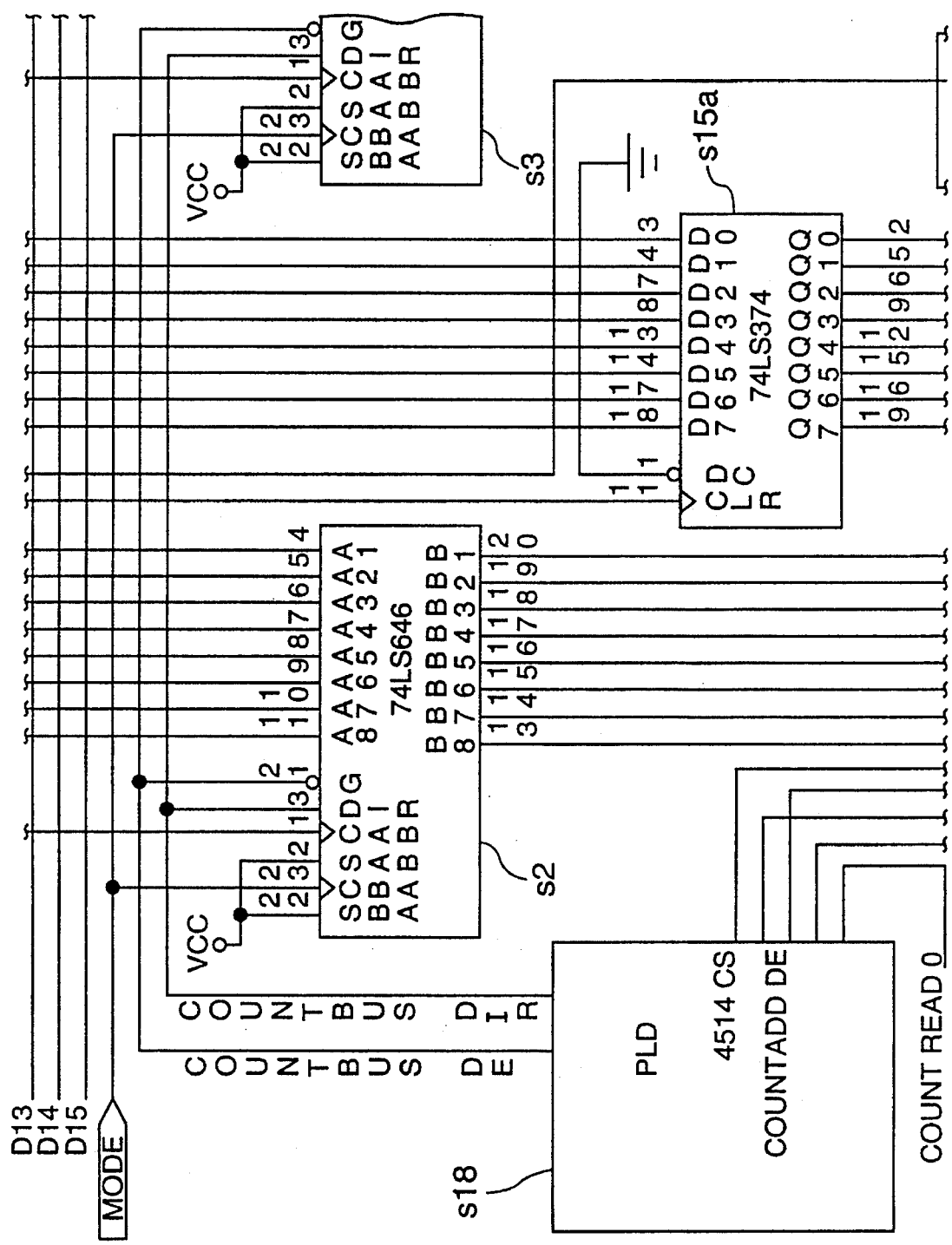
Figure 4F:
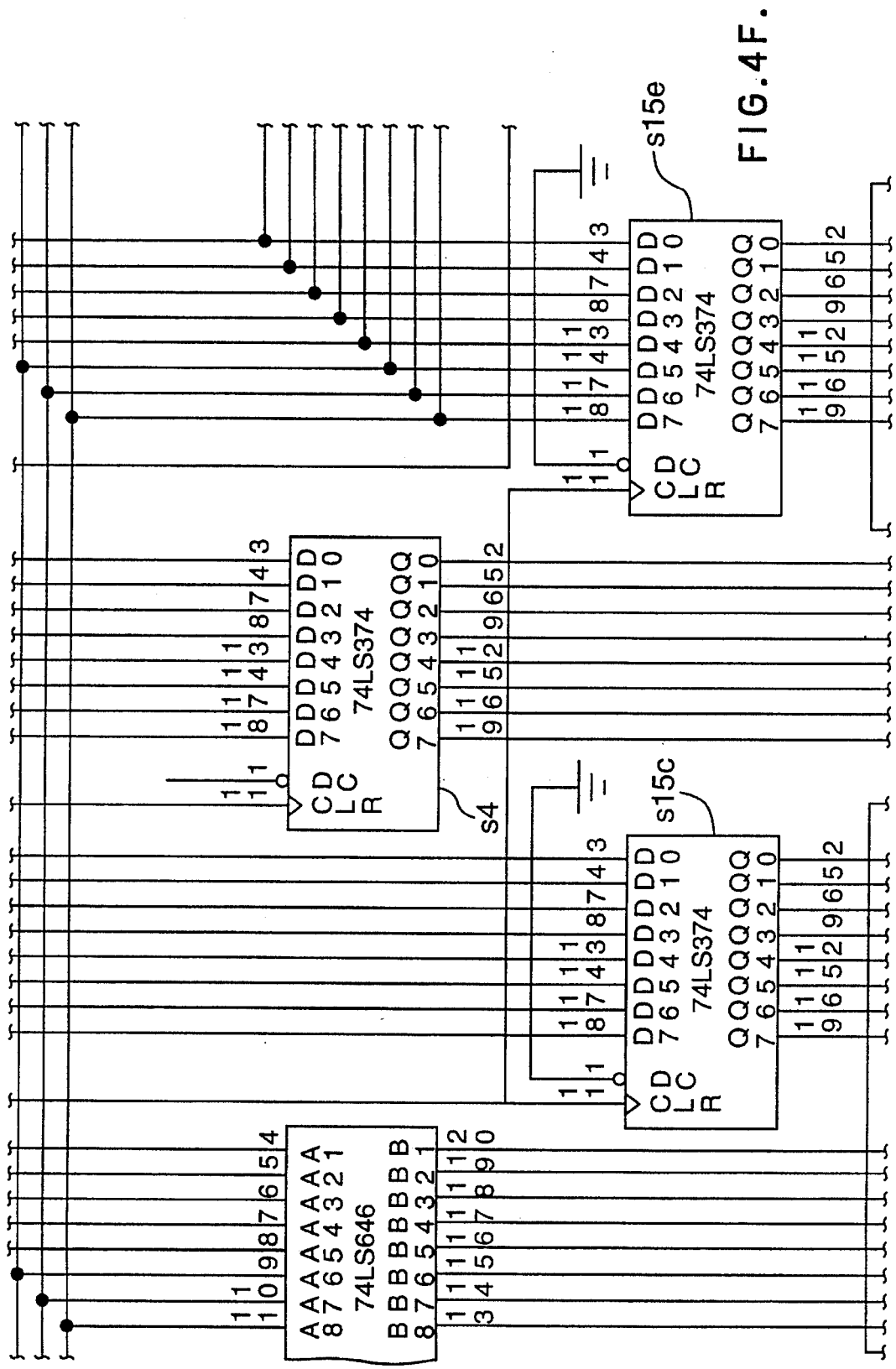
Figure 4G:
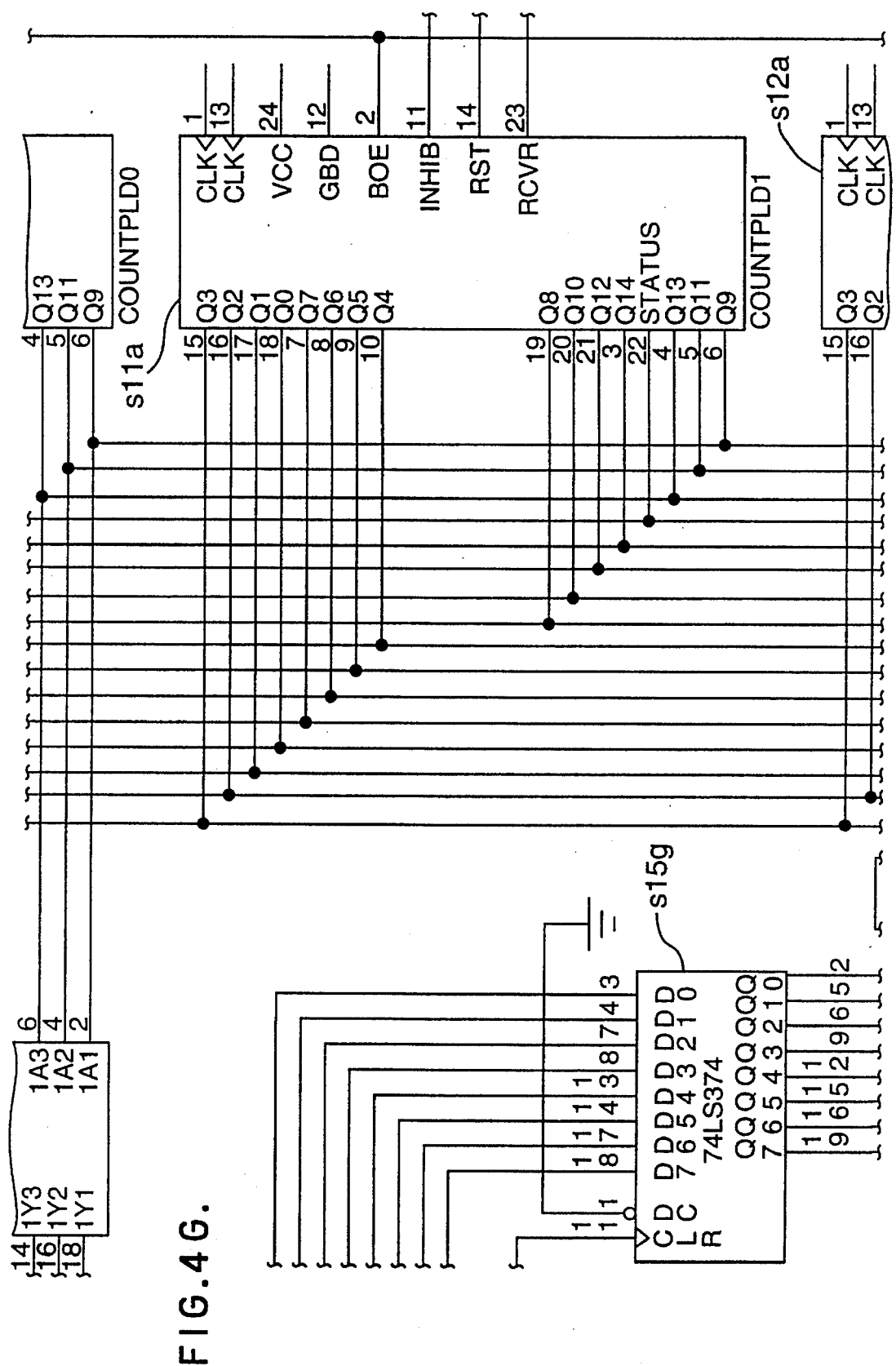
Figure 4H:
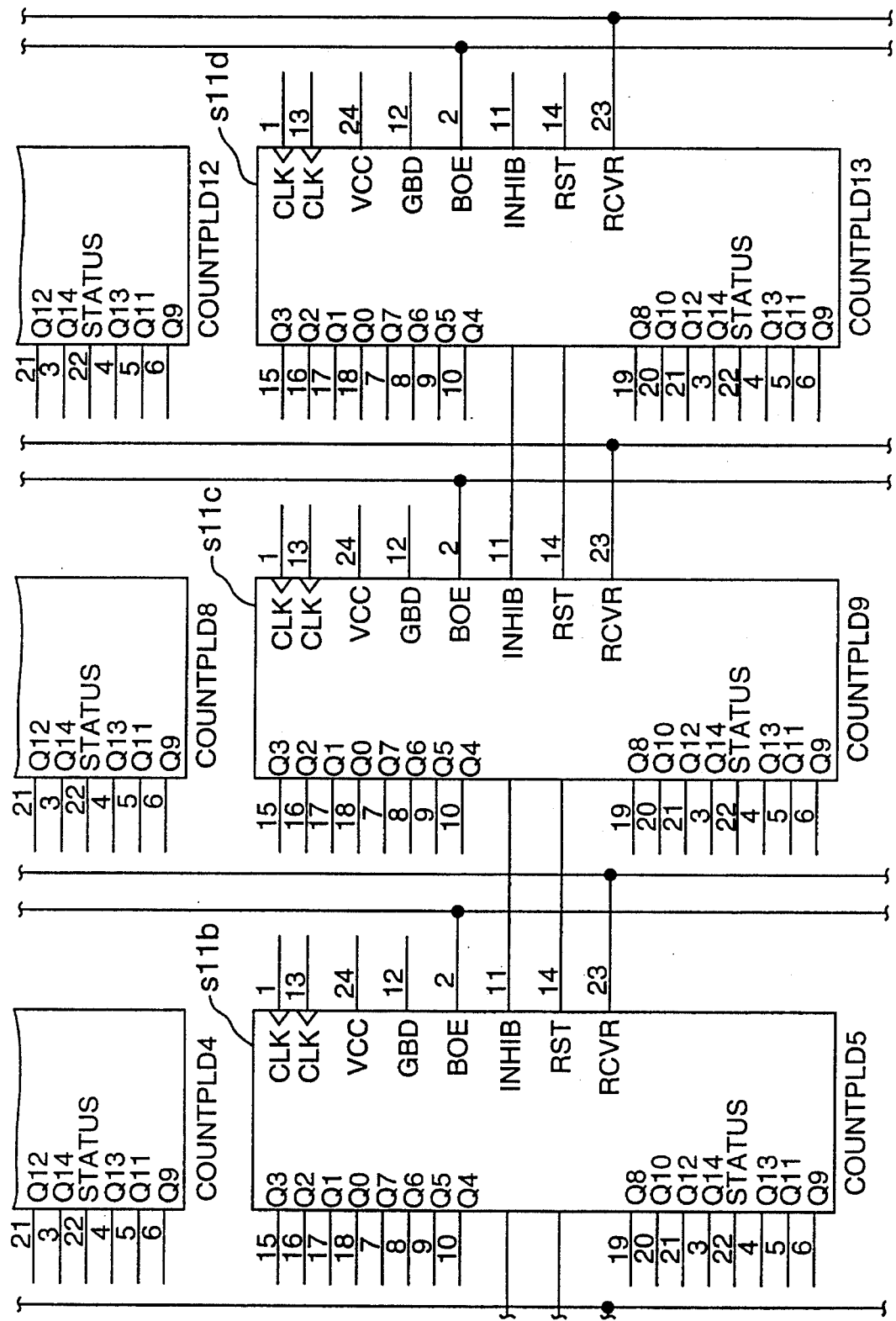
Figure 4I:
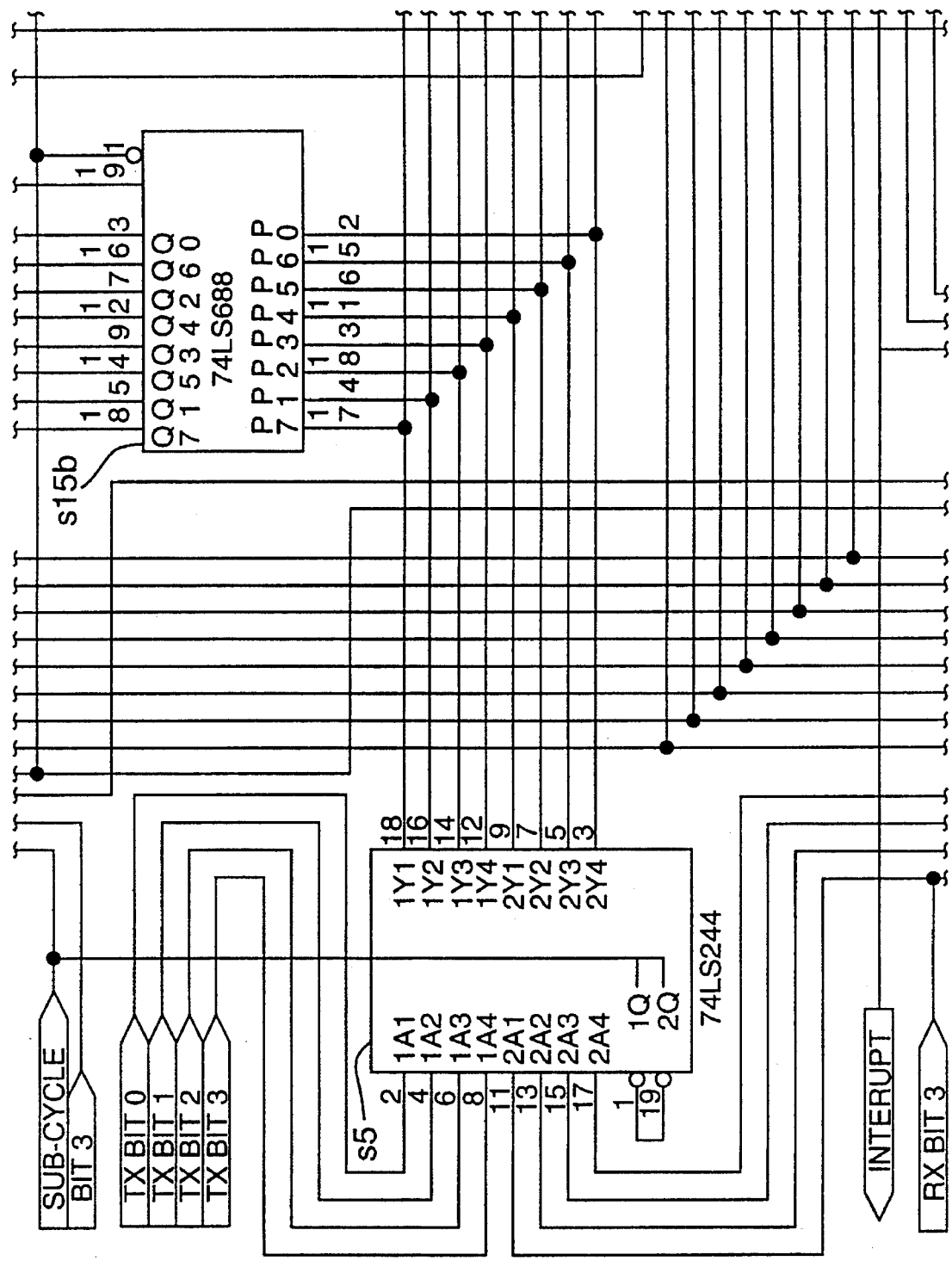
Figure 4J:
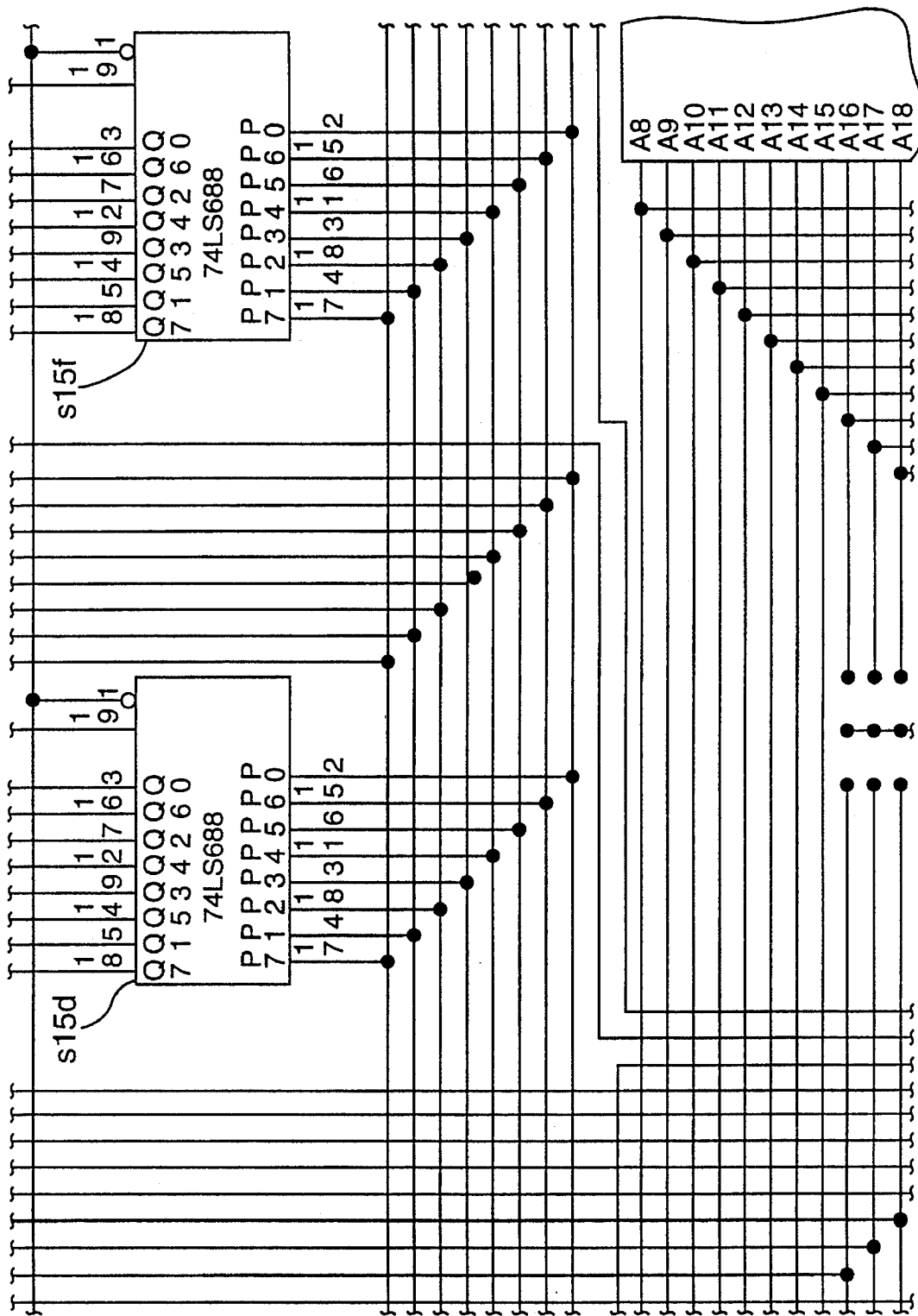
Figure 4K:
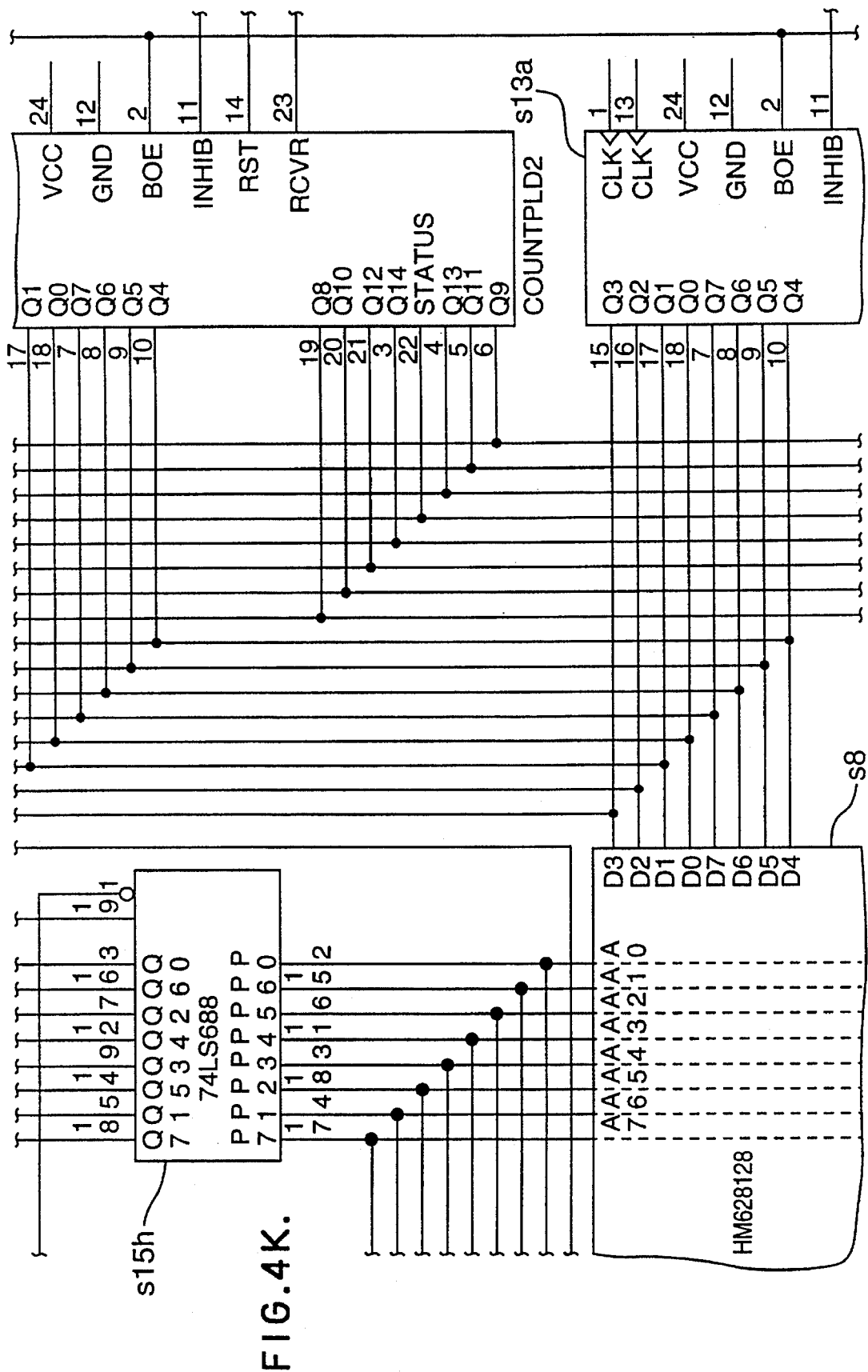
Figure 4L:
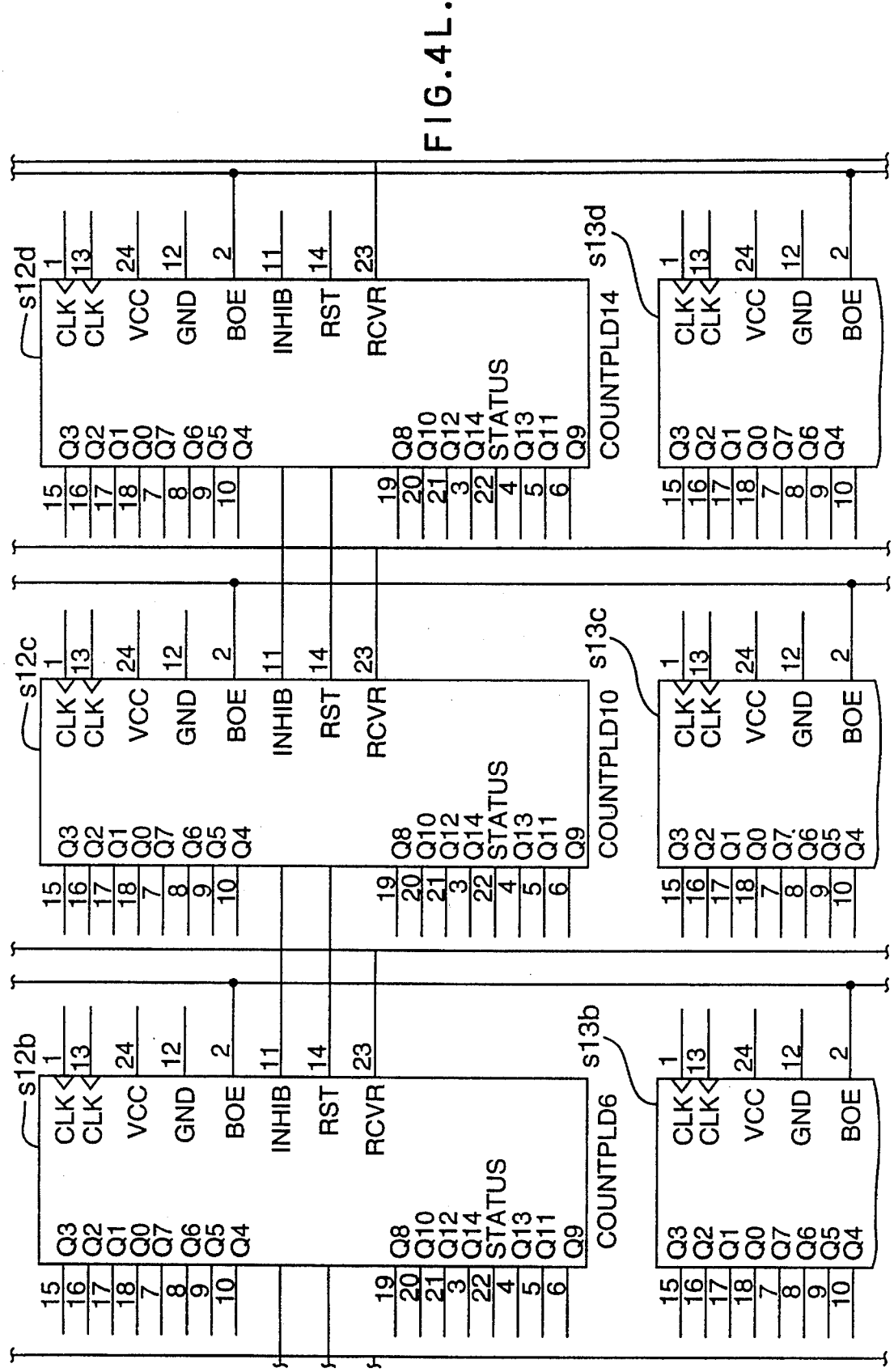
Figure 4M:
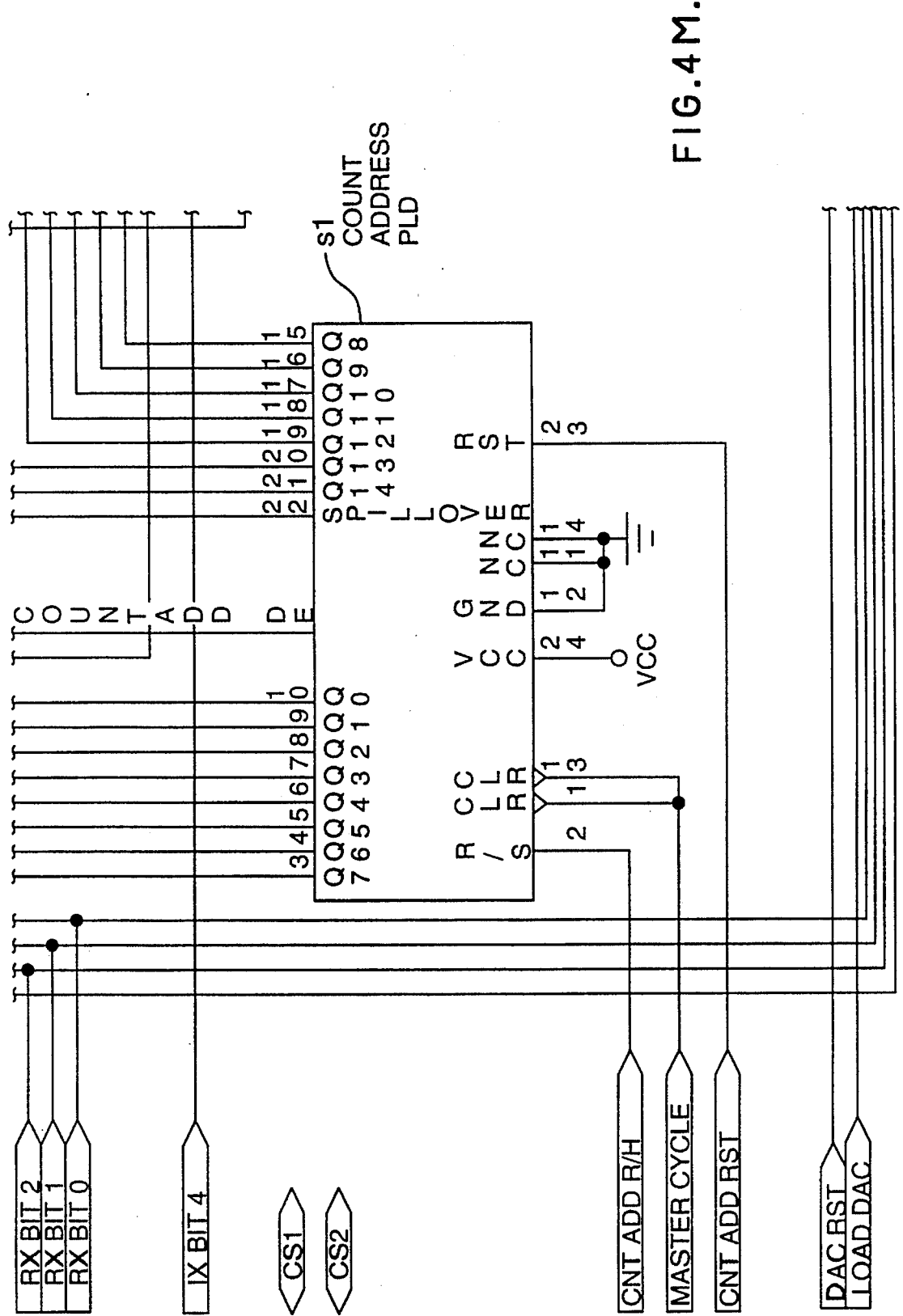
Figure 4N:
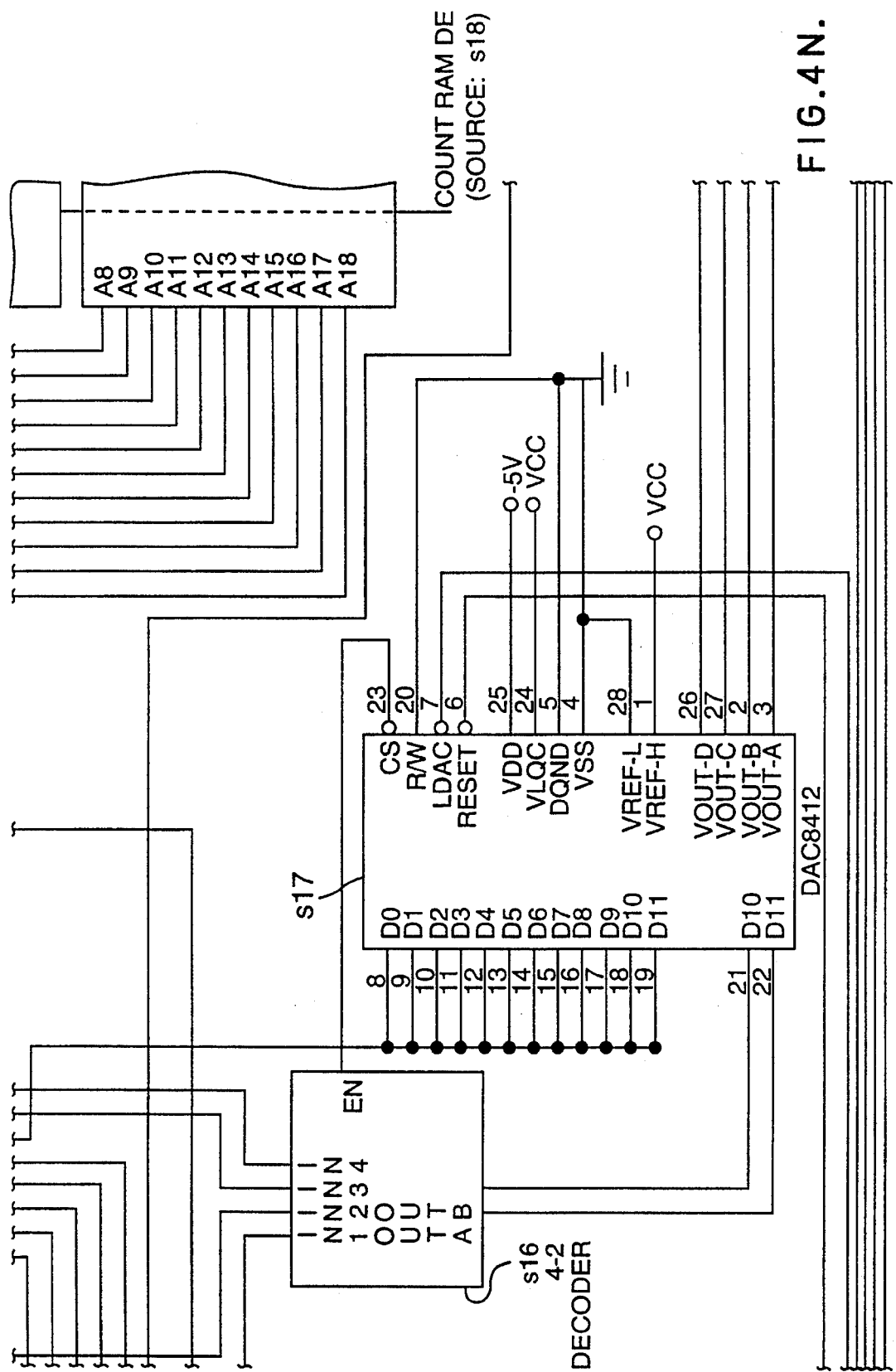
Figure 40:
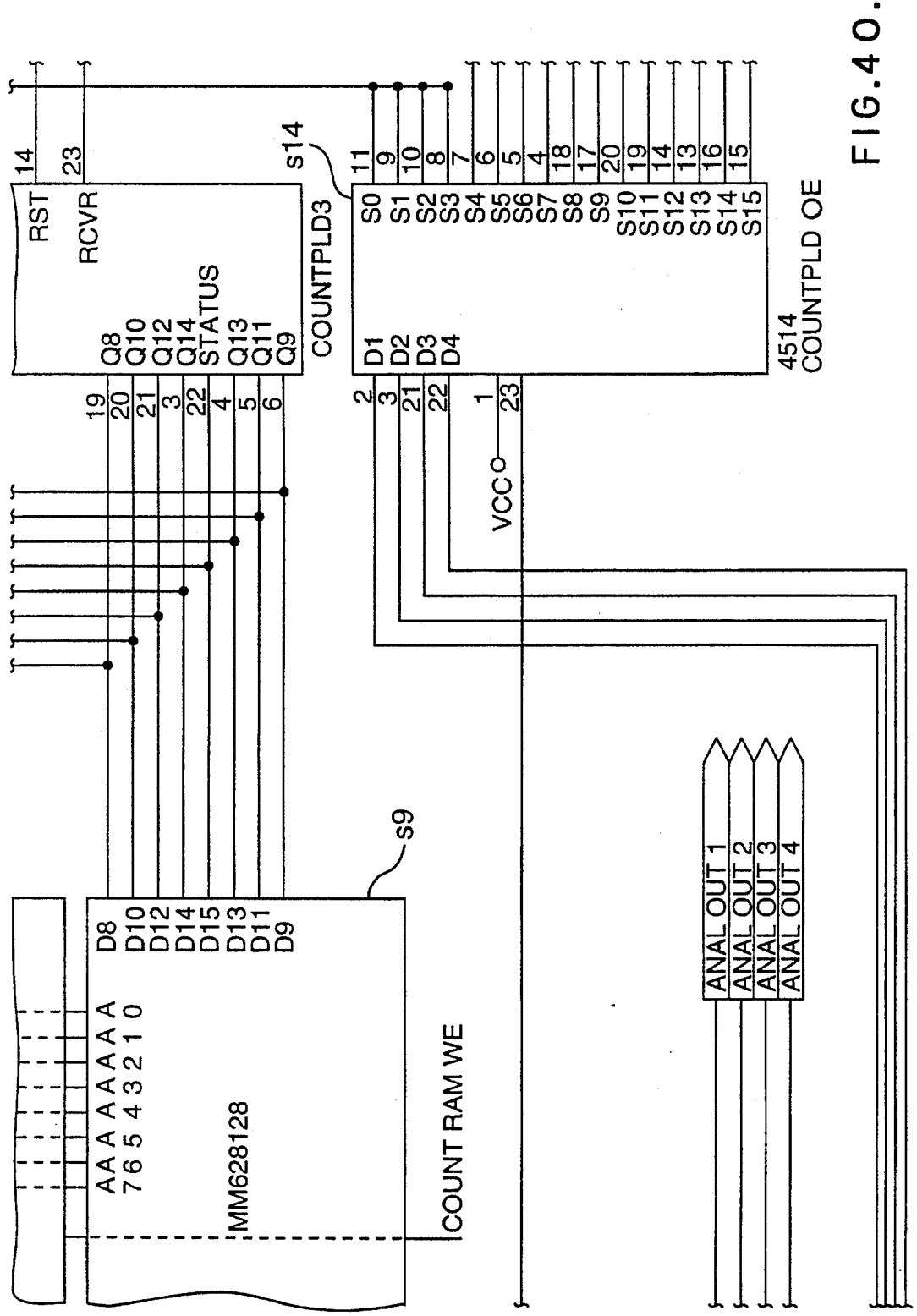
Figure 4P:
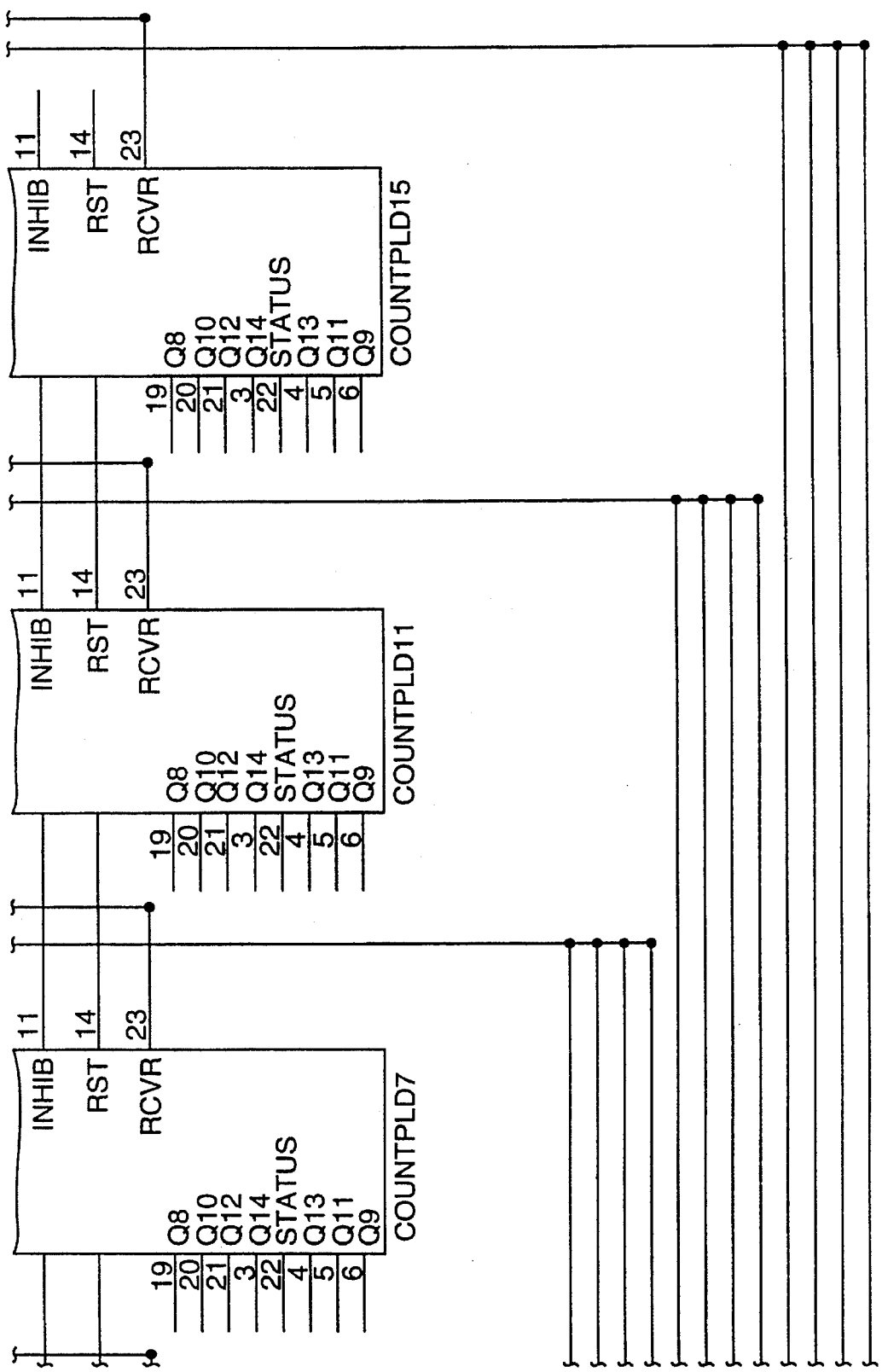
Figure 5A:
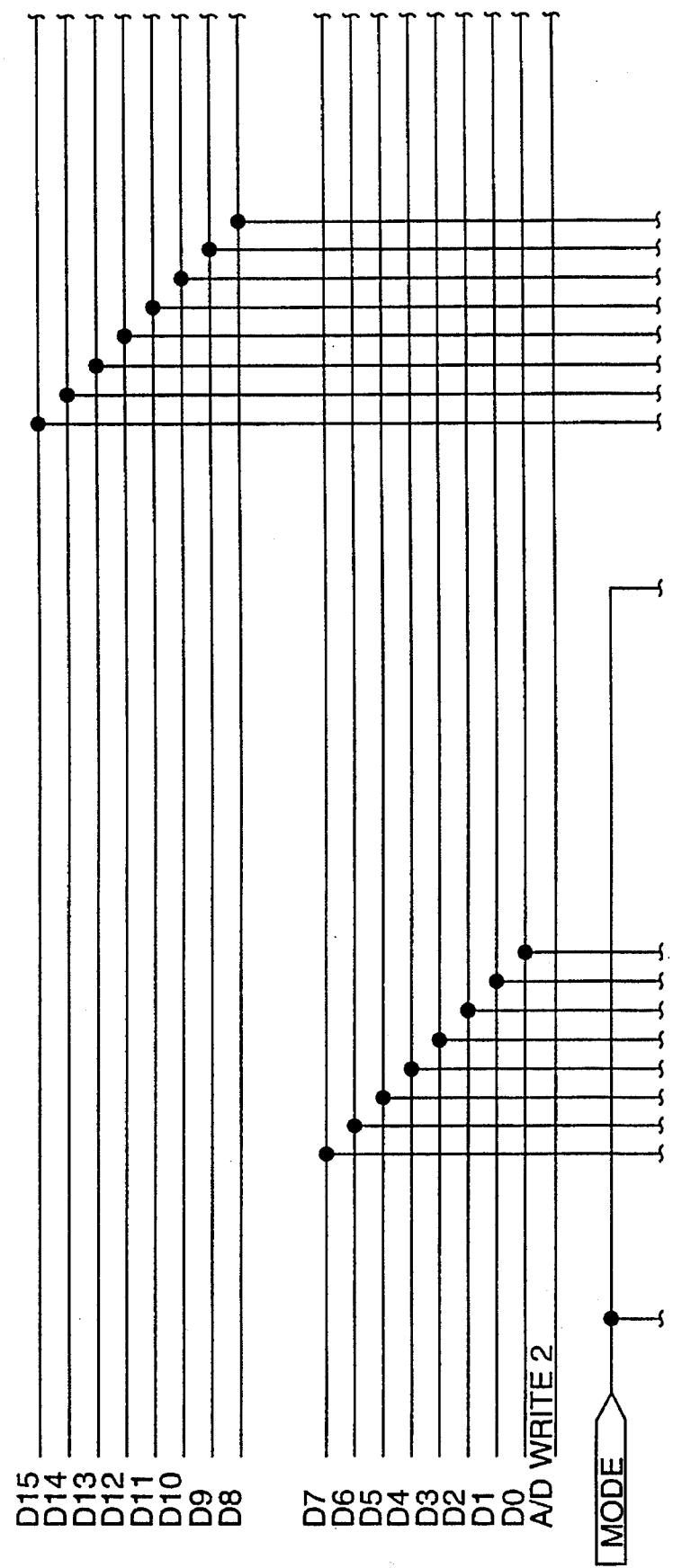
FIGS. 5A, 5B, 5C, 5D, 5E, 5F, 5G, 5H, 5I, 5J, 5K, 5L, 5M and 5N is schematic diagram of an A/D card architecture according to the preferred embodiment.
Figure 5B:
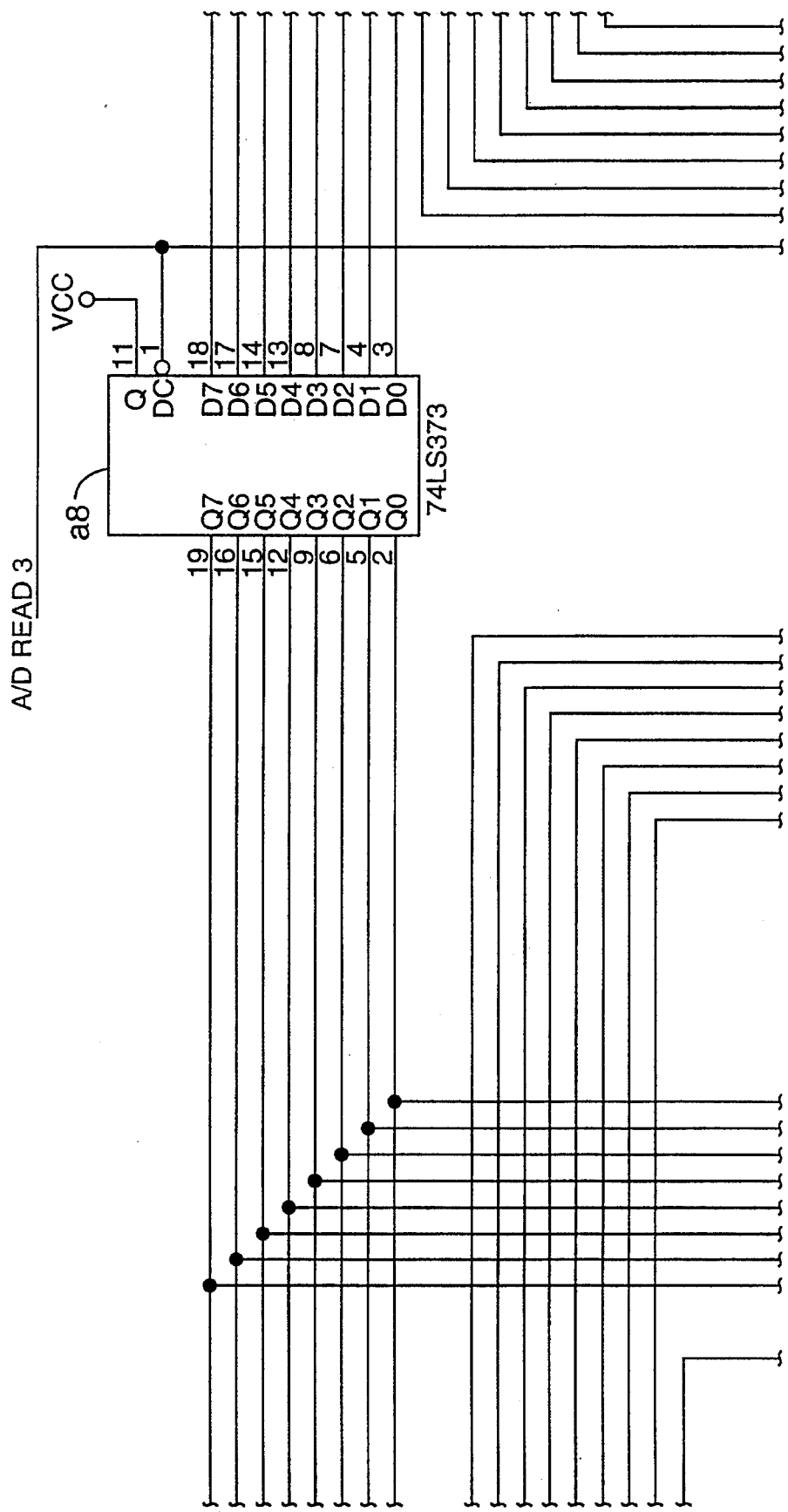
Figure 5C:
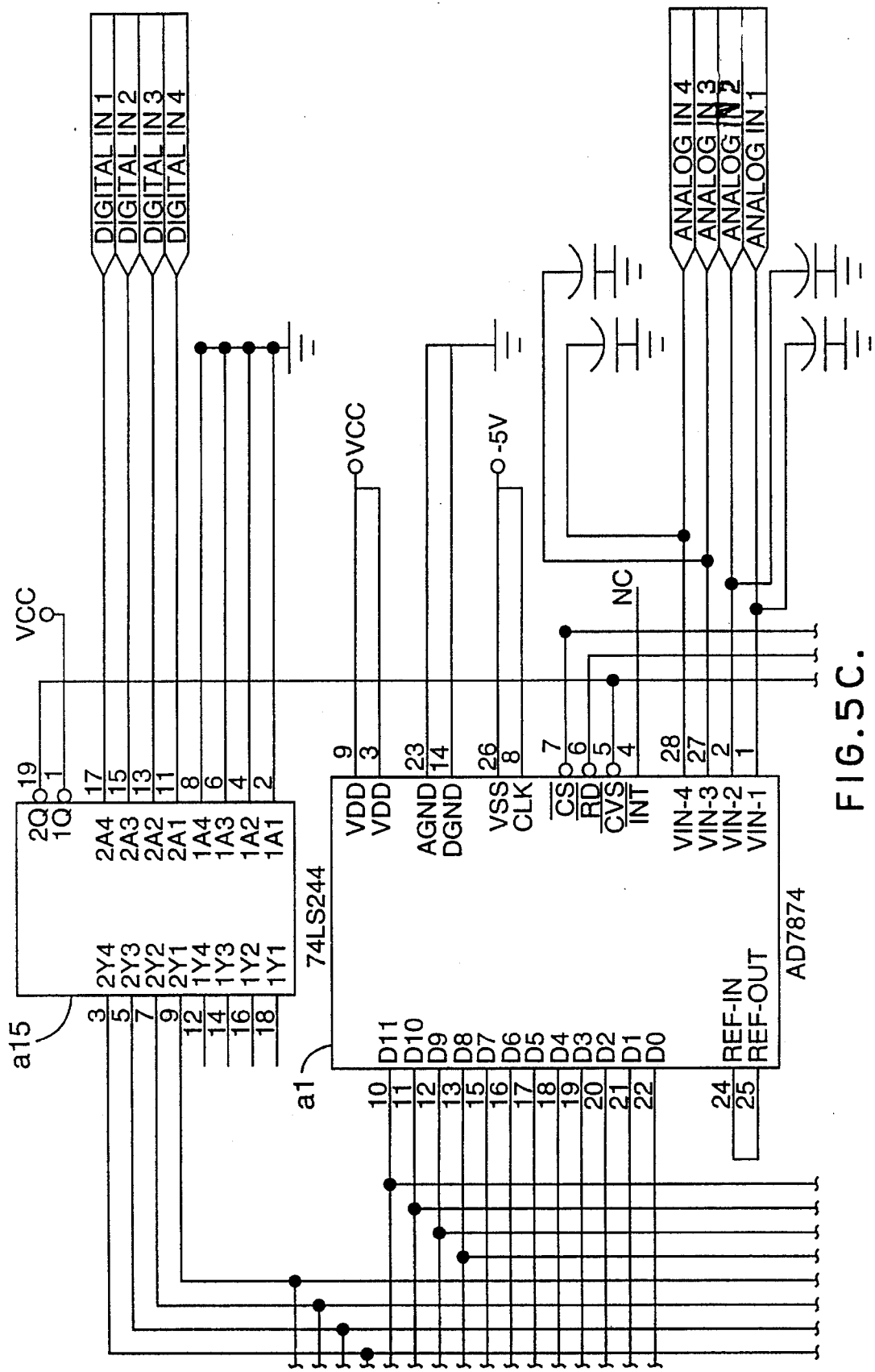
Figure 5D:
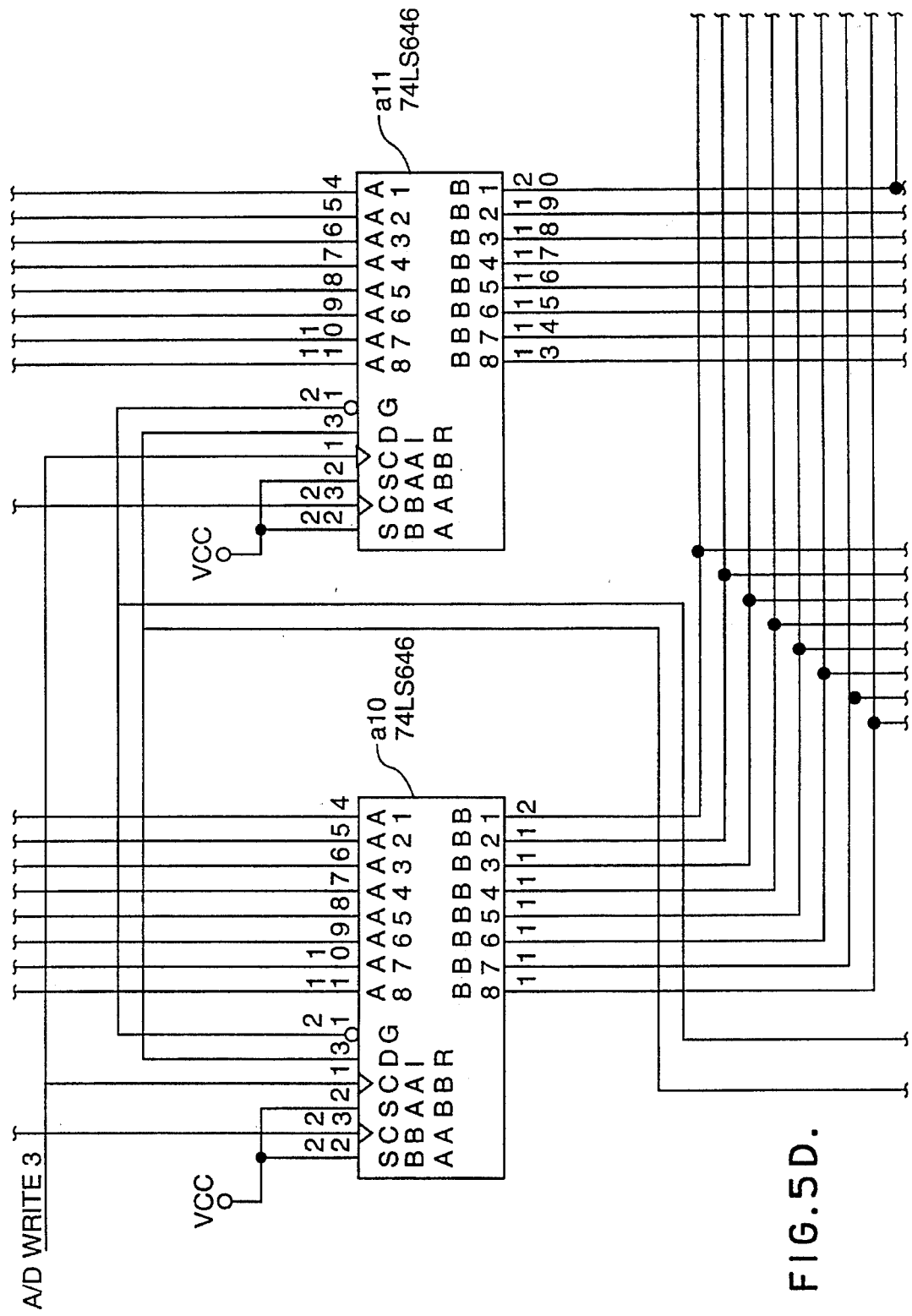
Figure 5E:
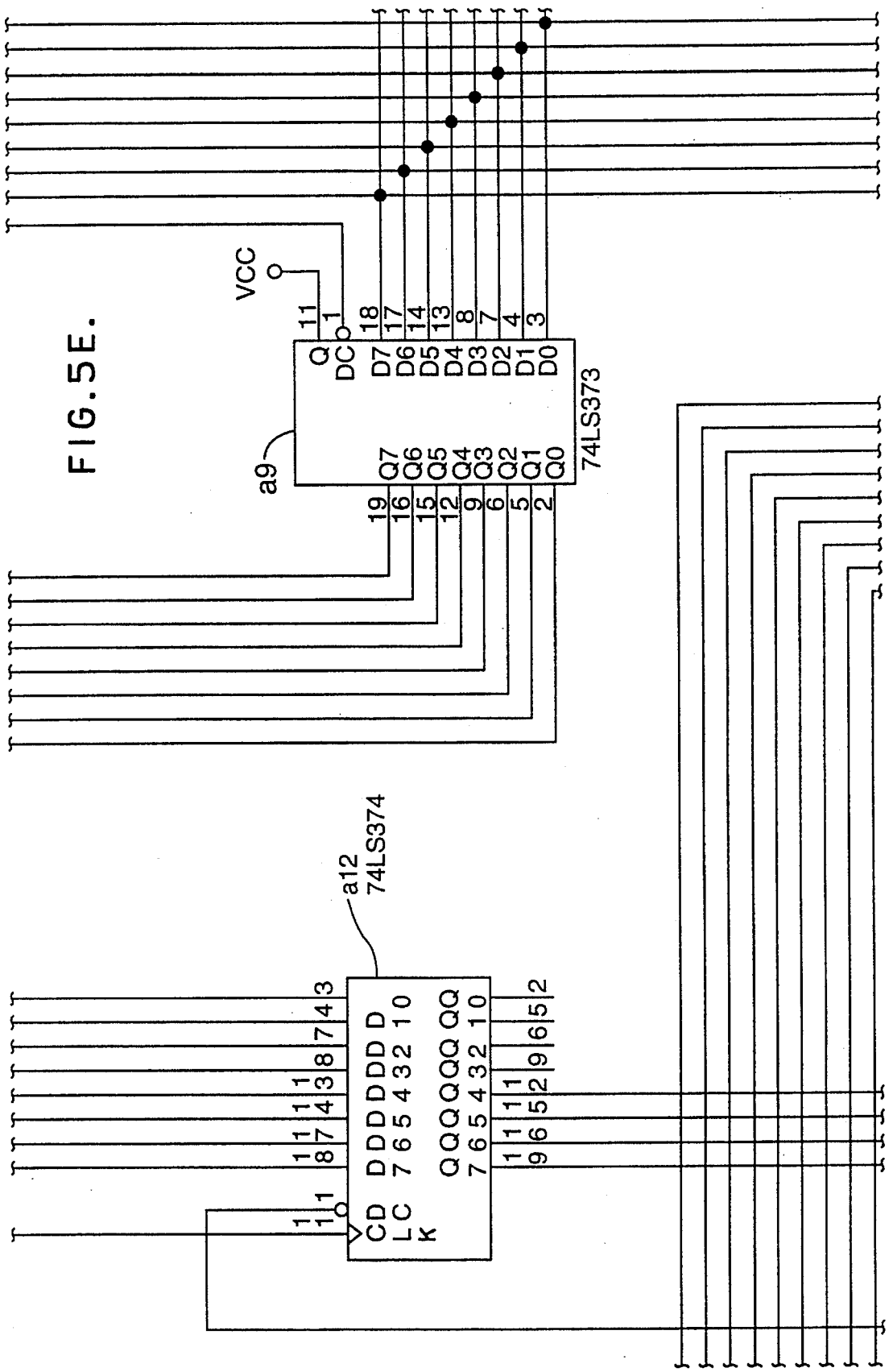
Figure 5F:
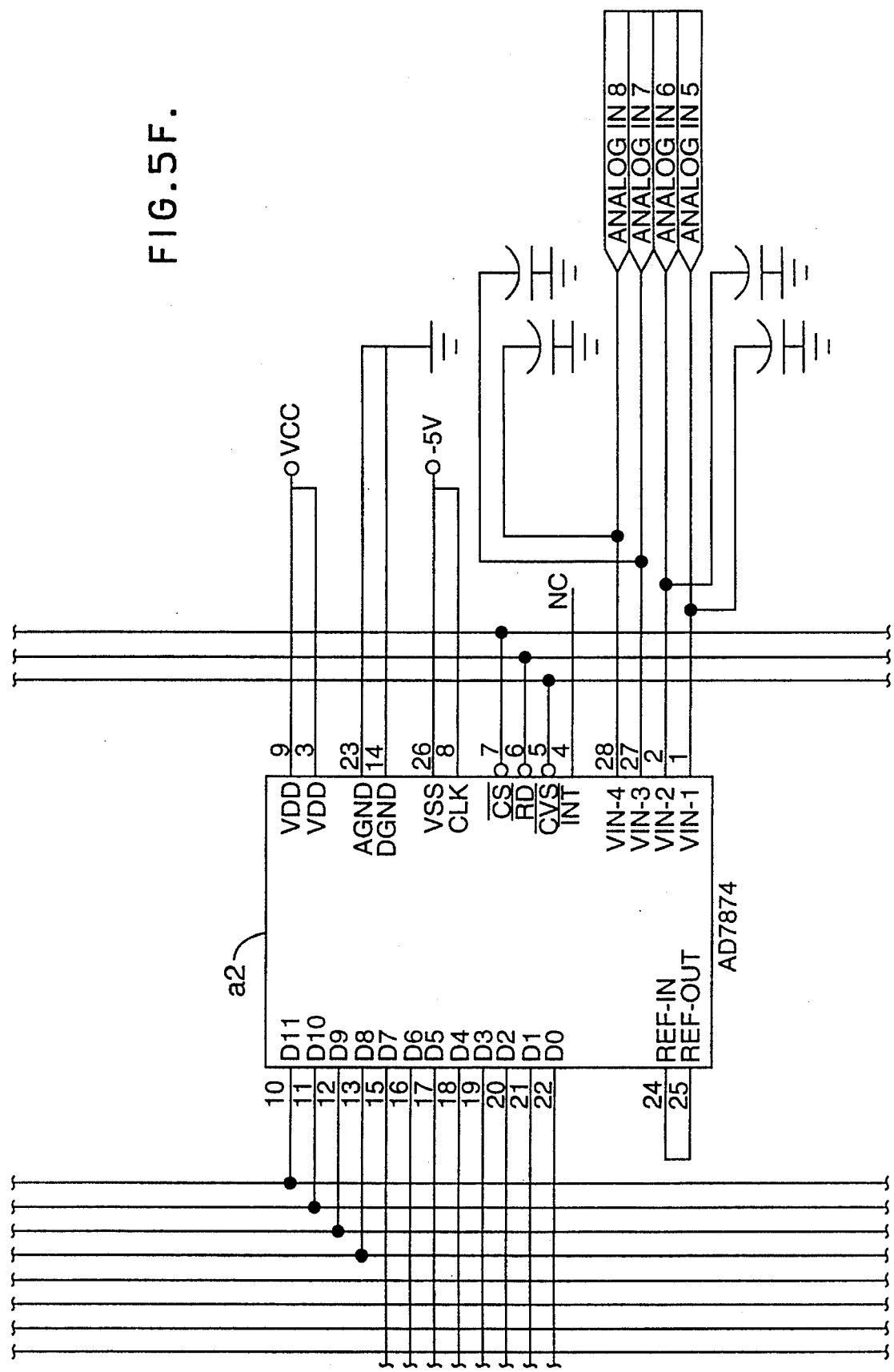
Figure 5G:
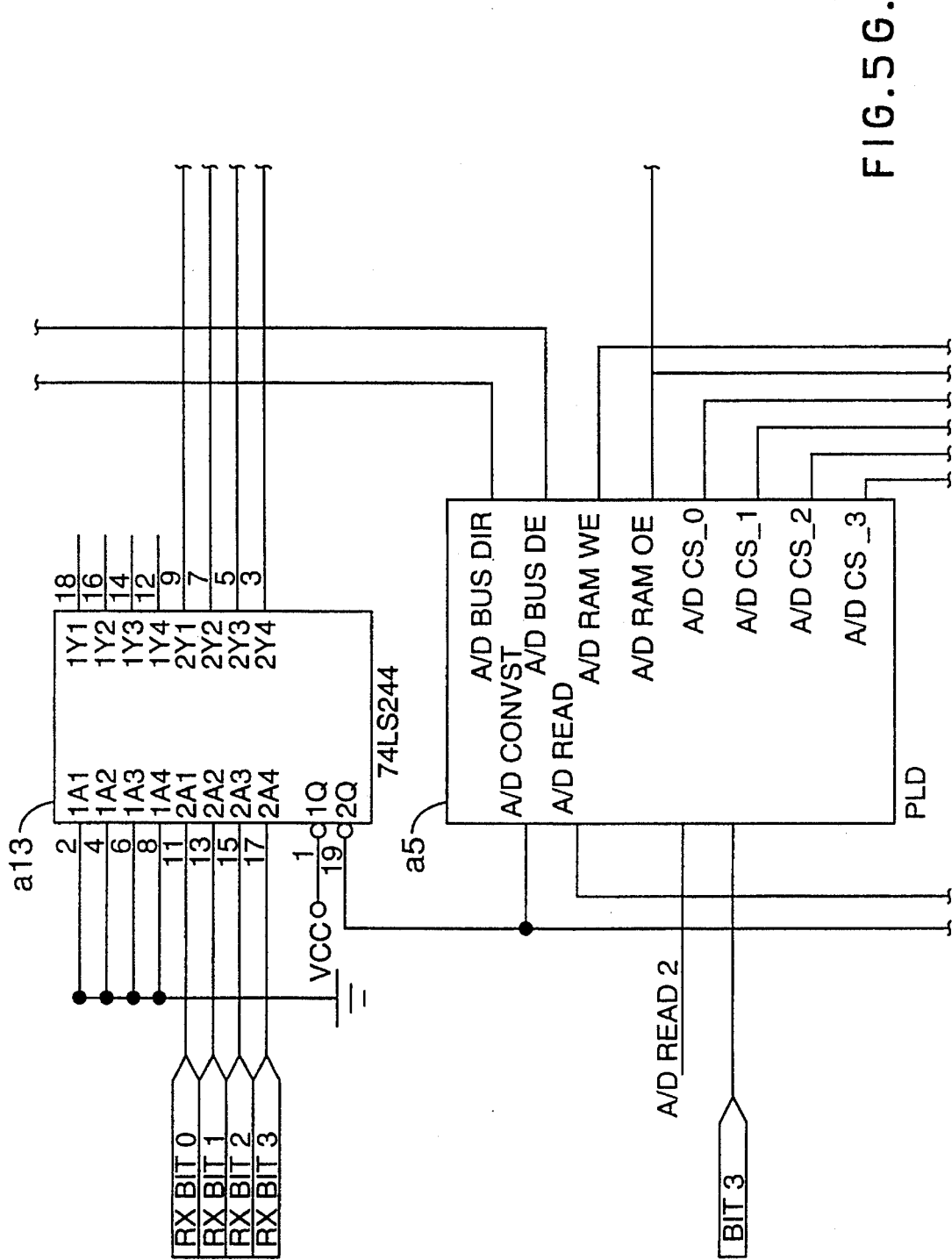
Figure 5H:
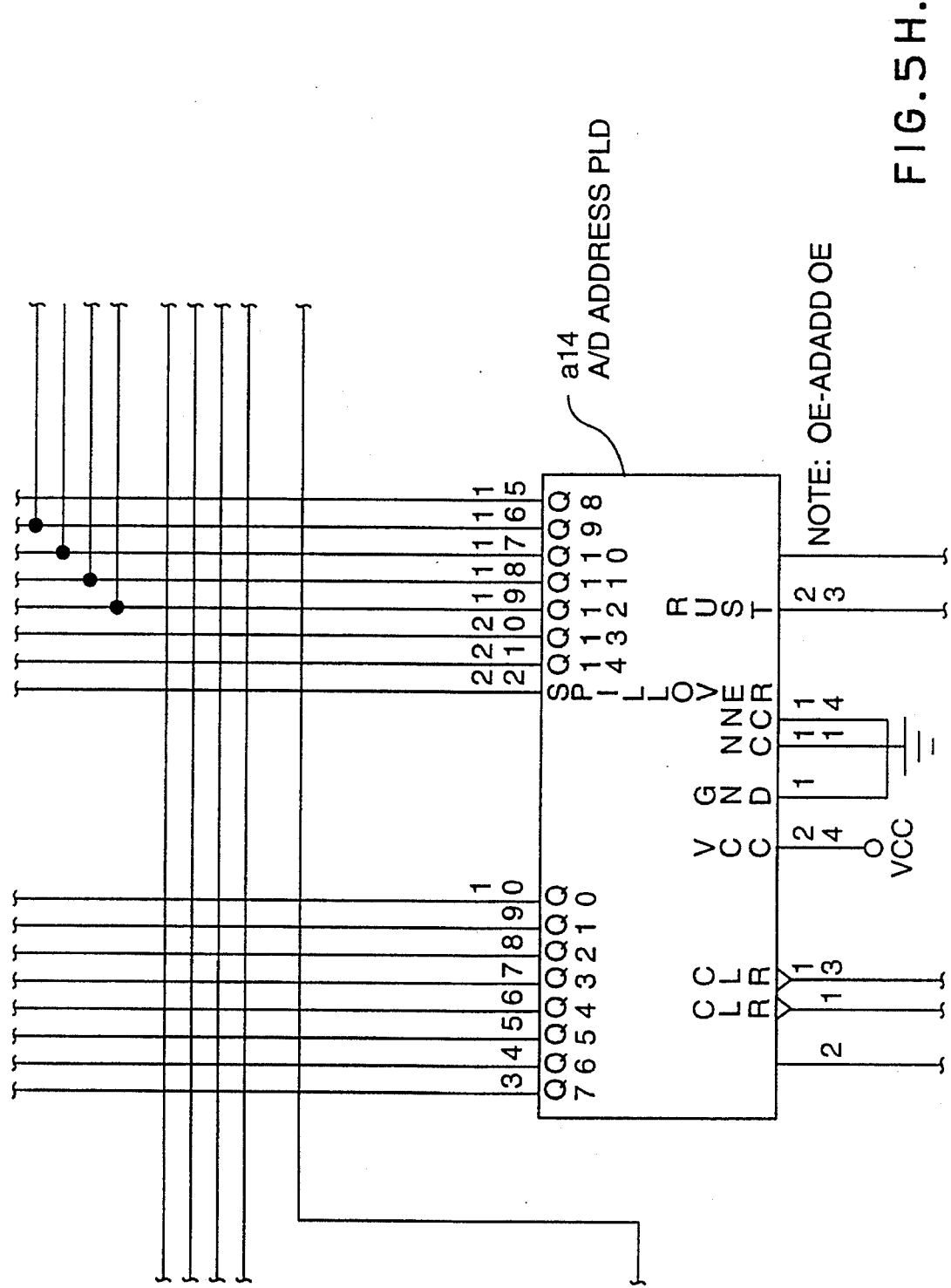
Figure 5I:
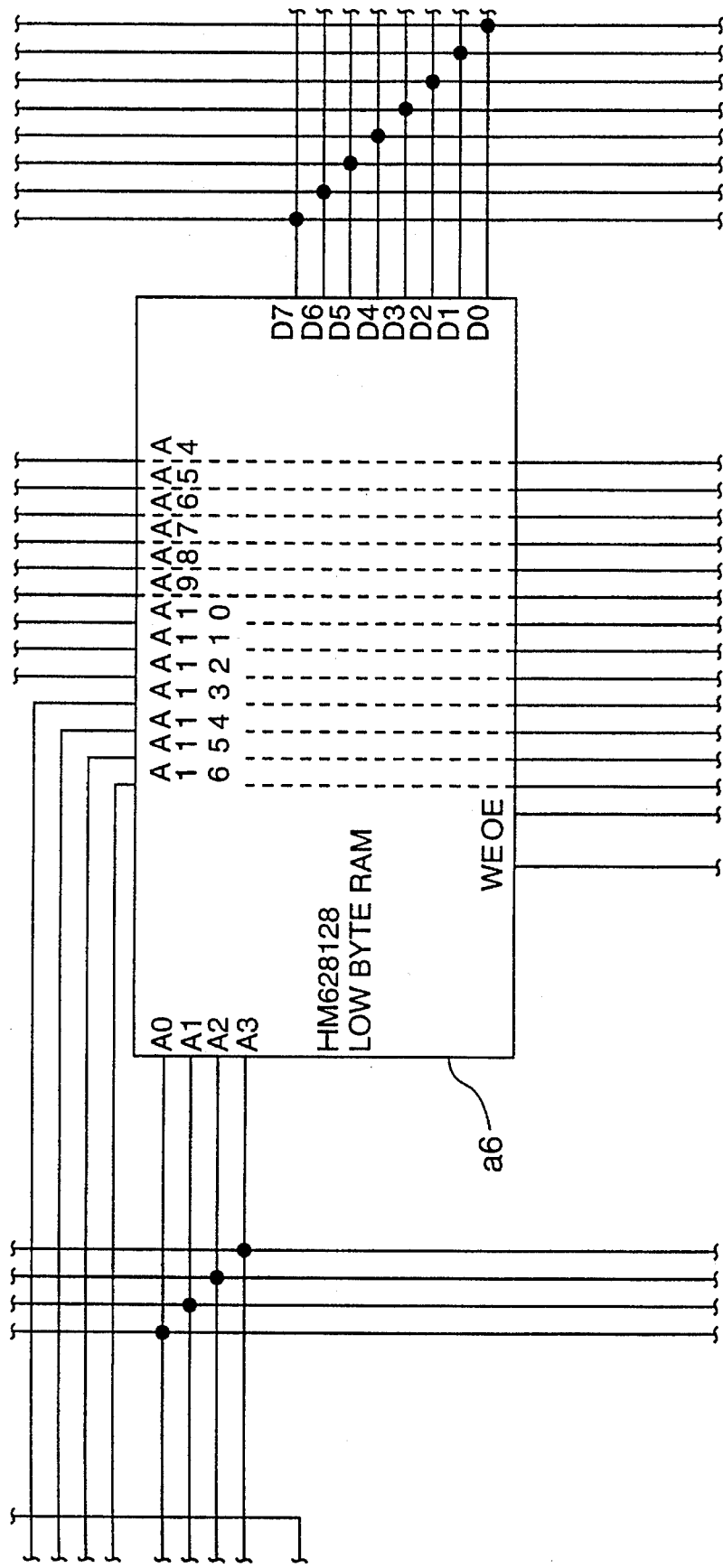
Figure 5J:
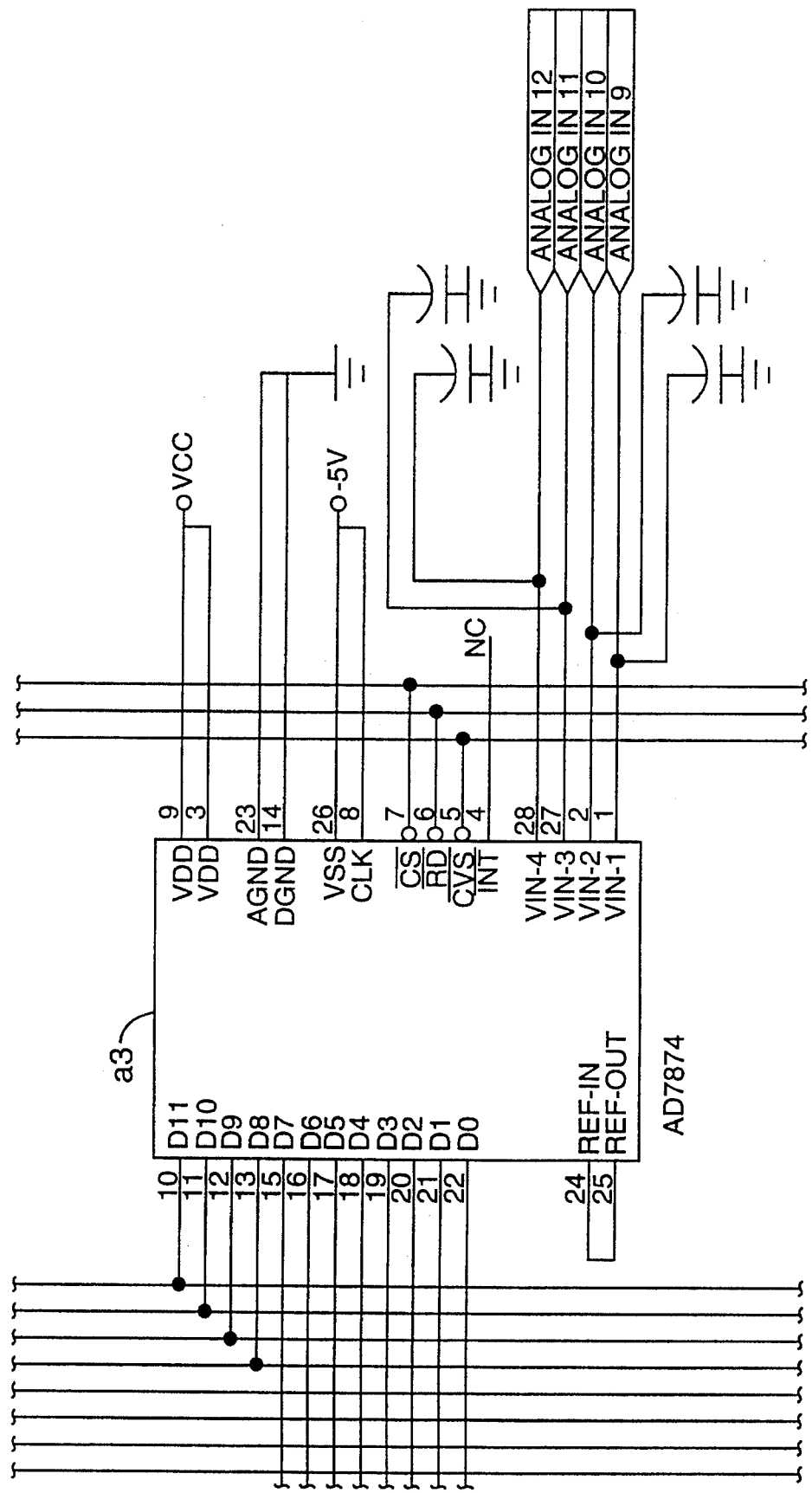
Figure 5K:
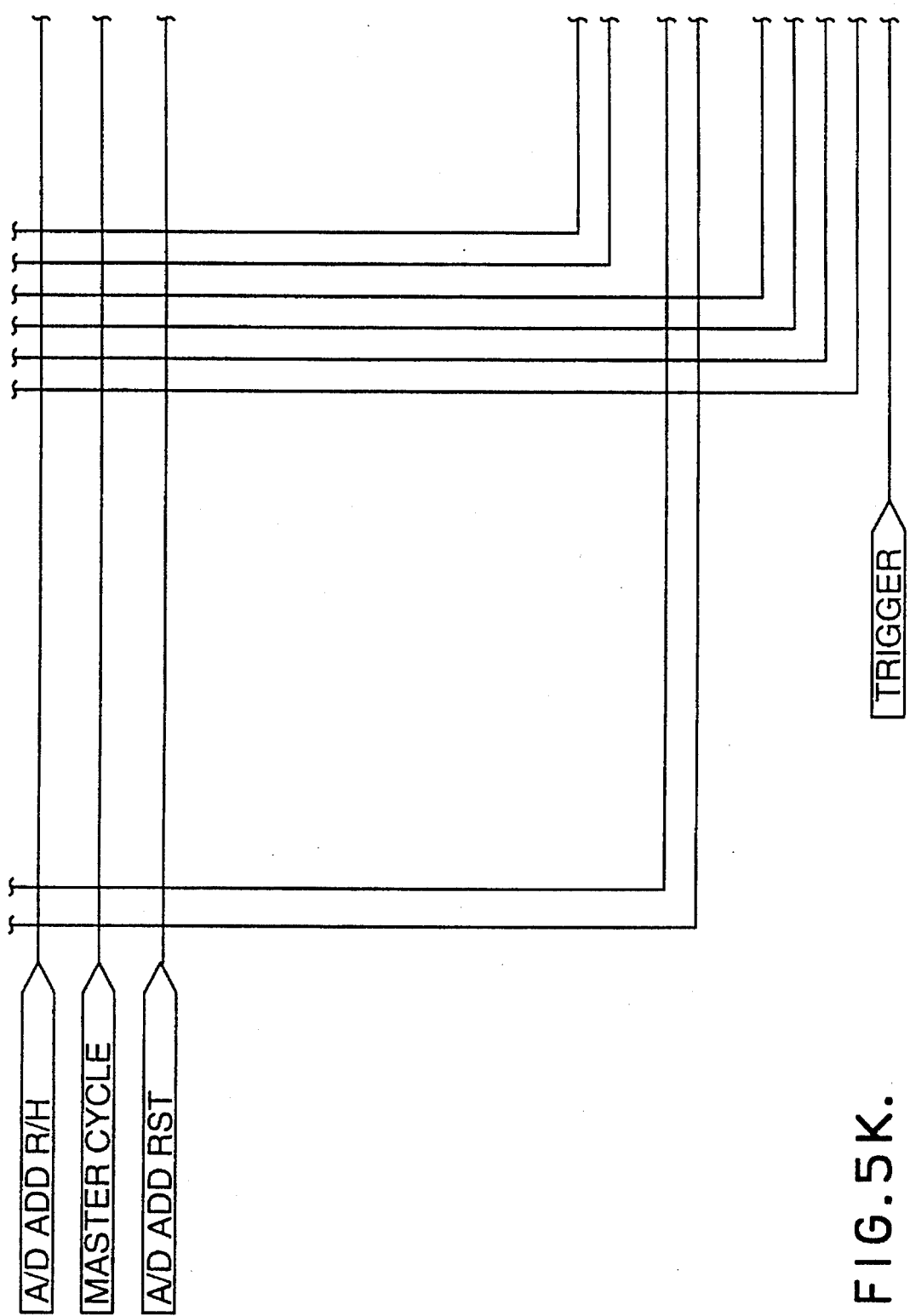
Figure 5L:
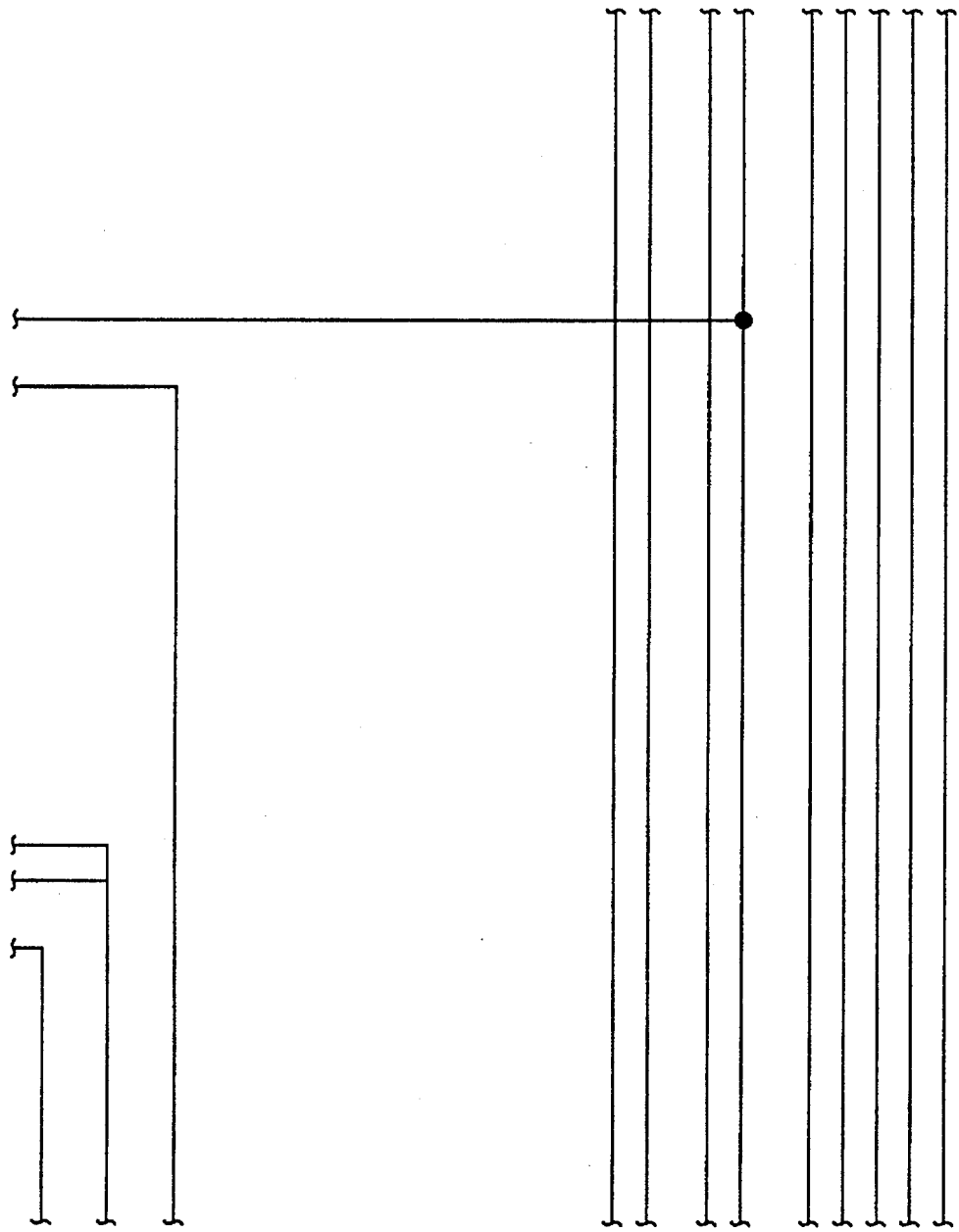
Figure 5M:
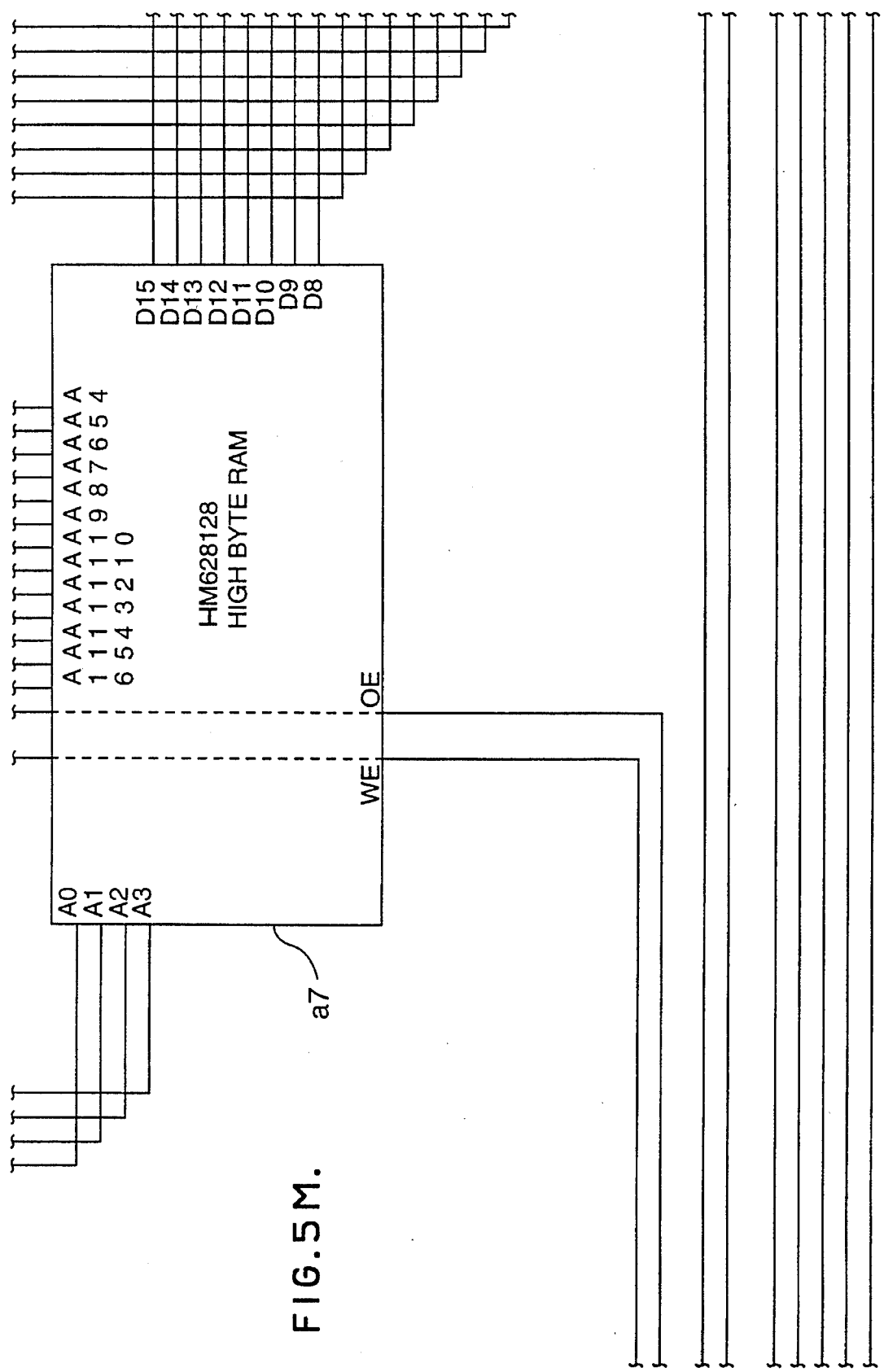
Figure 5N:
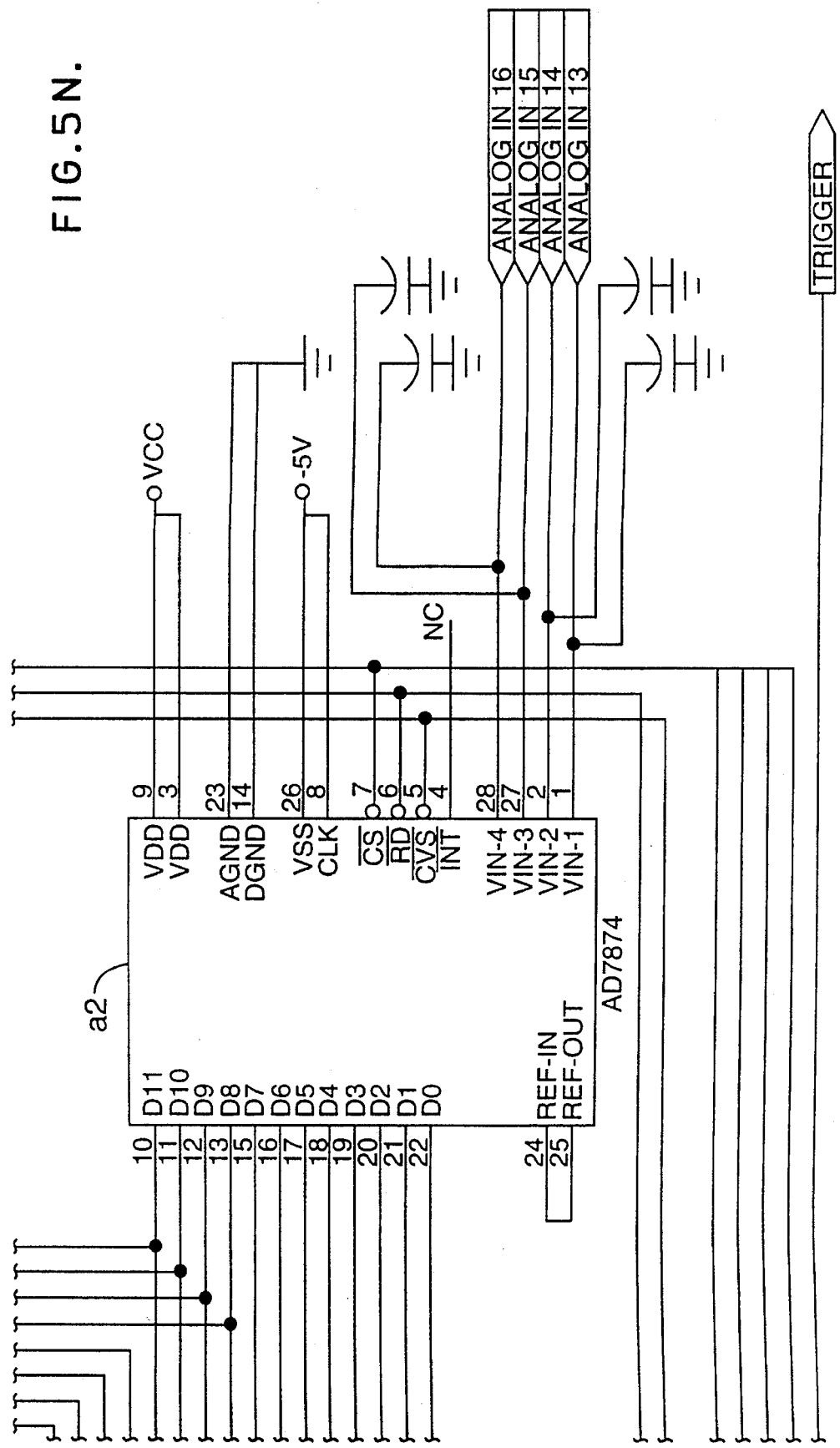
Figure 6A:
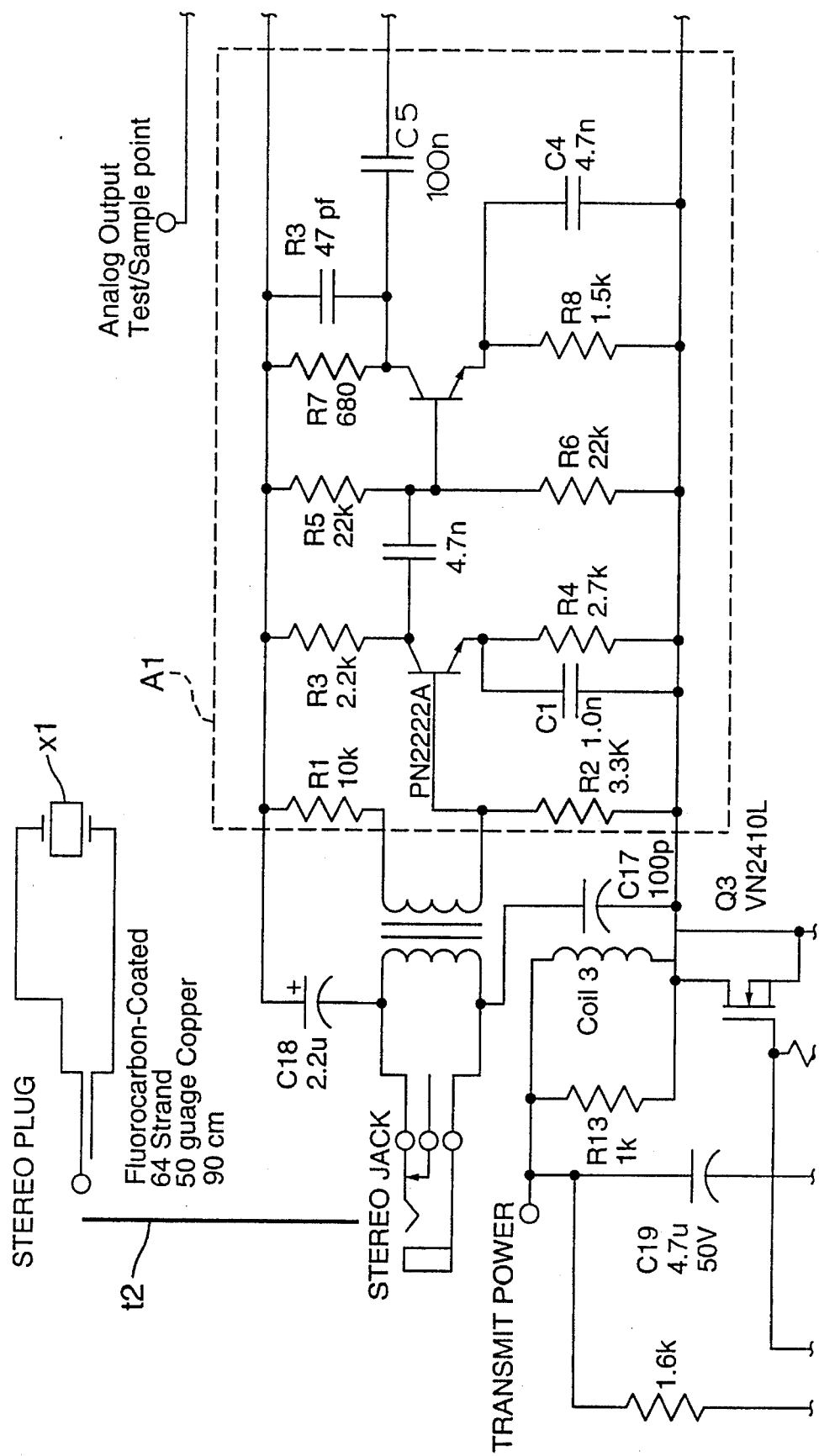
FIGS. 6A, 6B, 6C and 6D, is a schematic diagram of a transmitter/receiver/transceiver architecture according to the preferred embodiment.
Figure 6B:
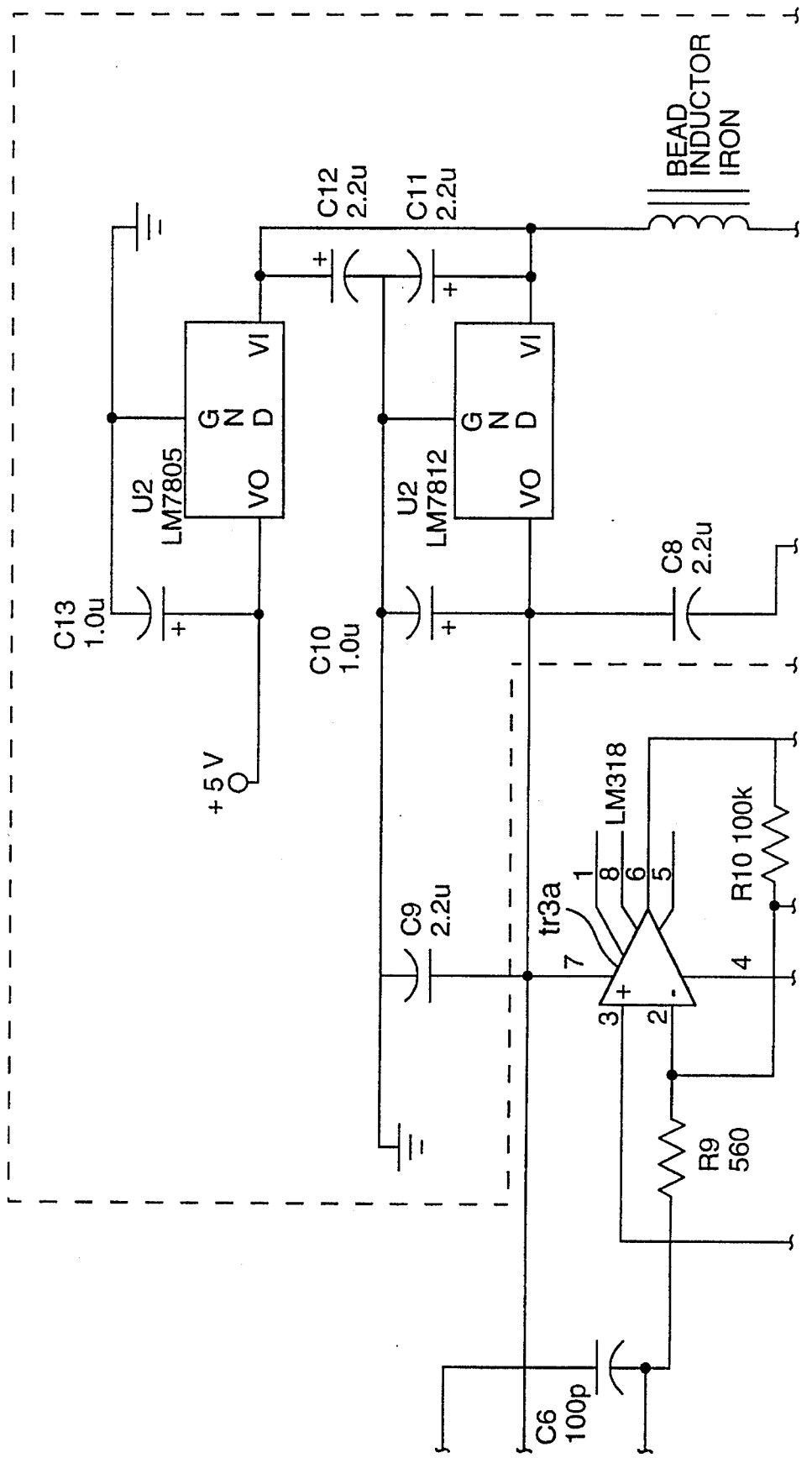
Figure 6C:
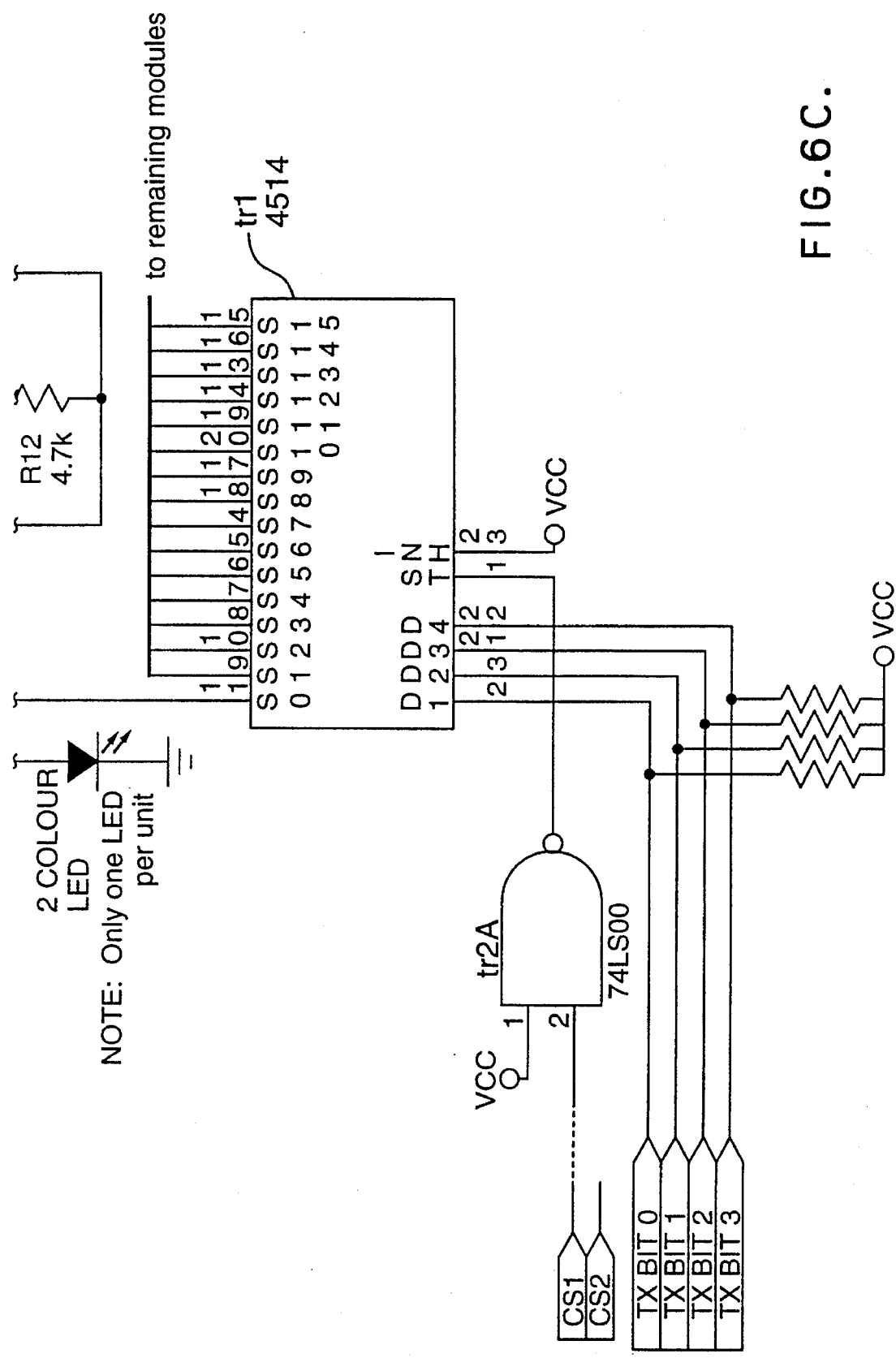
Figure 6D:
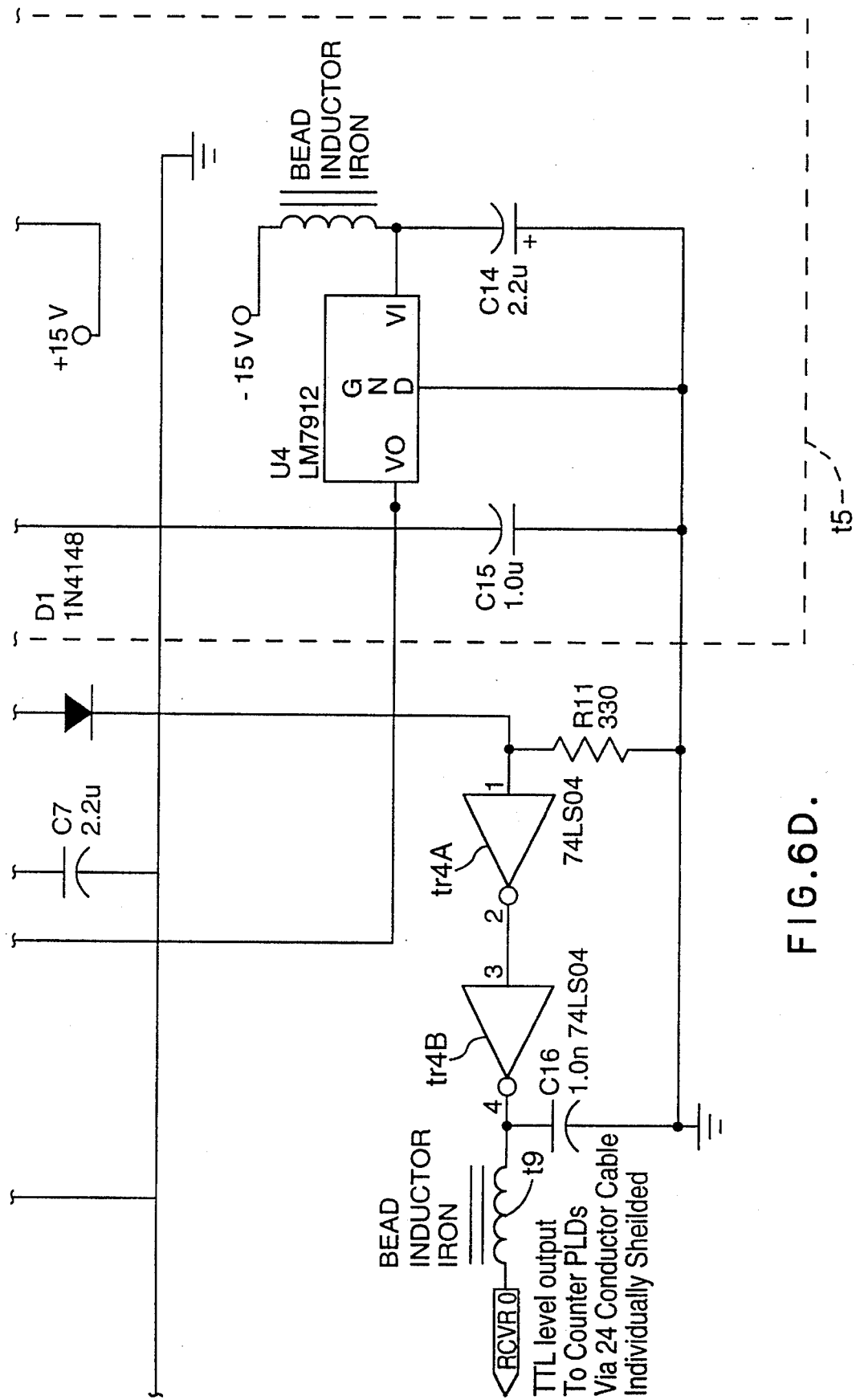

FIG. 2 is a block diagram of the computer interface and addressing scheme common to all three digital cards. It should be noted that the system is classified as an I/O mapping device as opposed to memory mapping device. Consequently, dedicated I/O registers within the controlling processor are responsible for all data throughput.

As illustrated in FIG. 2, the system computer interface architecture features a full two byte data transfer (D0–D15), as well as partial address decoding (A1–A13). Full two byte address decoding is not required. All signals sent to, or taken from the AT bus are buffered using octal buffers (d1 & d2) for both address and control lines, and transceivers (d3 & d4) for the data lines. In terms of decoding, each board features an eight position dip switch (d7) or equivalent for address selection. Address lines A6–A13 are used for this function, thus providing 256 distinct addressing locations, each with a resolution of 40 h ($2^6$). It should be noted that A0 is not used for address decoding.

An 8-bit magnitude comparator (d5) is used to equate the manually set dip switch with address lines polled by the computer mother board. When a match is found, a signal is generated which gates demultiplexer each of 1-of-8 d8 and d9. The lower three address lines (A1–A3) are used as inputs to both of these Read and Write demultiplexers. To distinguish their functionality, the buffered IOR signal is sent to opposite polarity enables on each demultiplexer. Thus if IOR is in a high state, the system computer interface is in a Write mode. To avoid Reading and Writing from the I/O address ports, A4 is also used as an opposite polarity input d8 and d9. This has the effect of offsetting the Reads from the Writes by precisely 10 h ($2^4$). The result of this is two controllable ranges of eight data bits used for gating "reads" from the digital boards, and "writes" to the digital boards. A single PLD (d6) serves to handle the glue logic between the other components of the decoder circuitry.

Due to the architecture of the x86 family of microprocessors, there are only a finite amount of I/O registers. These registers can be partitioned into either 65535 8-bit registers, or 32767 16-bit registers. Due to the nature of the data transfers to and from the boards, and by selection of an active low signal to the I/O CS16 input of the AT bus, only 16-bit data transfers are employed by the system.

The only remaining control line extending to the digital circuit card is the Address Enable (AEN). This signal is used in conjunction with the I/O Read and I/O Write signals to gate the magnitude comparator (d5). By doing so, Direct Memory Access (DMA) conflicts are avoided between the tracking system and other internal computer modules of the P.C.

The first functional module in the ultrasound tracking system of the present invention is the controller card. A functional diagram is provided in FIG. 3, which comprises FIGS. 3A, 3B, 3C and 3D. The controller card employs the identical bus decoding scheme described above with reference to FIG. 2, to govern and pace the functionality of the overall system. As with all of the digital cards, the controller is preferably a four layer Printed Circuit Board, (PCB), with the embedded layers being the power and the ground planes, respectively.

The operation of the card is as follows: A single Programmable Logic Device (PLD), c1, is programmed to cycle through a full two byte count at 32 MHz. The output registers of c1 are always active, so that the counter is constantly outputting a count value between 0–65535. These outputs are used for both comparative and timing purposes throughout the system. For this reason, a highly reliable, fast-response PLD is required. Functional blocks c2–c5 latch predetermined values from the decoding circuitry, and compare them to the output of c1. Thus, upon system start-up, specific values are written to the registers of c2–c5, and once those values are matched by the output of c1, respective signals are generated to govern such features as Pulse Length (6-bit), Cycle Length (8-bit), and Inhibit (15-bit). As illustrated, the "equating" outputs of the low data byte comparison (c2 & c5) require an edge triggering flip-flop (c11) to hold their equated state. The output of this high data byte comparator (c4) is of sufficient duration to feed directly to c10 and c12. Using a 32 MHz clock, the Pulse Length signal is variable between 0 µs and 2.00 µs at 31.25 ns increments, the Inhibit signal between 0 µs and 2.048 ms and 62.5 ns increments, and the Sub-Cycle Length signal is variable between 0 µs and 2.048 ms at 16 µs increments. Typical values are loaded into the registers of c2–c5 to best suit a given application, as discussed in greater detail below.

A second function of the c1 counter is to generate signals to a resetting 1-of-8 demultiplexer (c10) which in turn generates signals for application to c1 and c11 for resetting important system parameters. As can be seen in FIG. 3, one of these parameters is the Mode function which governs the direction of data flow in the octal transceivers located on the remaining system cards discussed in greater detail below. Four c1 outputs are also used to cycle through the RCVR lines of the system, thereby providing a default of 16 receiver modules.

A second major role of the controller card is to manage the performance of the transmitter activation bits. Using a transmitter PLD (c6) as a preloadable up counter, a value indicative of the start transmitter is latched to its input registers. Using an output of the c10 multiplexer as a clocking signal, c6 increments the six transmitter bits and outputs them both to a transparent buffer (c13), and to a 6-bit comparator (c9). Since the transmitter bits are sent to all three digital boards, as well as to the computer peripheral, the transparent buffer is required to avoid capacitive loading.

The ending transmit value is sent to the second side of the 6-bit comparator after it has been latched by c7. The octal latch (c8) is used simply to read the status of the transmitter bits by the controlling software. Once the 6-bit comparison is made and equated, a value is sent out to the local bus to clock the address incrementors on the remaining two digital cards. Although 6-bits are used for equating the transmitter increment bits, the default system allows for a 4-bit transmit value, corresponding to 16 possible transmitter channels. However, higher tier models of the ultrasonic tracking system of the present invention may employ up to 32 transmit cycles, corresponding to a 5-bit transmit value.

An 8-bit latch (c14) is also used by the system to generate and gate signals used to control address counters, interrupt controls, and trigger toggles.

Before most of the signals reach the local bus connecting the digital cards, they pass through c12, which is a simple "glue logic" PLD that ensures correct timing and signal polarity. This circuit module is also responsible for generating such parameters as the external system trigger for pacing and gating additional laboratory equipment.

Unlike the controller card which generates signals, the counter card (FIG. 4) receives signals to consolidate the ultrasonic distance information. The counter card features an external db25 connection to the transmitter/receiver/transceiver peripheral unit (FIG. 6). This twenty-four conductor, individually shielded connection between the counter card and the peripheral transmit/receive unit carries the 4-bit transmitter increment signals (TX BITS), the transmitter Pulse Length signals (CS1 and CS2) as well as the sixteen default receive lines accommodating 16 transmitter channels (upgradable to 32). Again it should be noted that not all embodiments of the ultrasonic tracking systems according to the present invention, employ the full range of sixteen receivers, Therefore, where a receive line is unused, it is grounded so as to avoid interfering with the desired signals.

A functional diagram of the counter card or module is provided in FIG. 4. The functionality of the counter module is best described in two stages, data writing and data reading. Examining the data writing stage, at precisely the moment when a valid signal is sent out by the external peripheral unit (FIG. 6) to activate a transmitting crystal, the expandable bank of receiver PLDs (s10–213) are reset to zero. These counters then count up from a zero value in accordance with respective internal 32 MHz clocks. Each PLD (s10–s13) is connected to an individual receive transducer (FIG. 6). As the 15-bit digital count in each PLD (s10–s13) is incremented past a predetermined value, an internal register within the PLD is activated which permits the reception of a receive signal. This predetermined value is used to implement the inhibit feature of the system and is designed to block out the electromagnetic interference caused by activating a transmit crystal. Once the mechanical vibration of the transmitted ultrasound is detected by a receive transducer it is converted to an electrical signal, amplified, filtered, and sent back to the appropriate counter PLD. This has the effect of stopping the digital count within the chip.

Next, a 1-of-16 multiplexer (s14) is activated for causing the output enable feature of the counters to be sequentially achieved. The captured digital value corresponding to the separation distance between the active transmitter and each connected receiver is then output in two bytes to the on-board RAM modules (s8 & s9) for temporary storage. Each time the RAM modules are activated, a default of sixteen locations are written to, according to the sixteen default receive signals. This cycle is then repeated for the next transmitter in the system. The incrementing of the RAM addresses is handled by s5, an octal buffer that outputs the 8-bit quantity representing the receiver/transmitter value at any time. Once all the transmitters in the system have been sequentially activated and recorded, the master cycle signal from the controller module triggers s1, the counter address incrementor PLD. This module then increments the RAM addresses to the next major block for the next transmit/receive master cycle.

Typically, the on-board RAM modules s8 & s9 are 8-bit by 131,072. Thus, in the default configuration of sixteen transmitters and sixteen receivers, the RAM is cycled through 512 times before reaching its capacity. Options exist for upgrading the on-board RAM to 8-bit by 524,288, so as to allow for 2048 complete transmitter/receive cycles. It should be noted that for most biological investigations, a repetition frequency of 200 Hz is demanded. Thus, even with 256 kB of storage capacity (128kX2), the on-board RAM can be completely filled in as little as 2.56 seconds. Consequently, the system of the present invention includes software functionality for downloading the stored information. This process is described in greater detail below.

To successfully realize the data reading stage, the counter card or module monitors the addresses that are automatically incremented to the RAM, and writes values to those addresses. This task is carried out by the octal transceivers (s2 & s3). Using the Mode function generated by the controller card, the addressing data shifts from a reading to a writing state in accordance with the system timing. This gives the software the ability to activate any address in the RAM by simply writing out a 16-bit value to s2 and s3. Since the incrementing of the transmitter and receiver bits is automatic, there is no need to monitor their value. Thus, s4 can simply an octal D-type flip-flop rather than an octal transceiver.

Once an address is written to the RAM for data output, the octal buffers s6 and s7 are opened to permit the PLD distance data to be passed along the low and high byte data paths into the I/O registers of the motherboard processor, then to the computer RAM, and finally to the hard disk for permanent storage. As can been seen in the system timing diagrams (FIGS. 7 & 8), the system is in a data output mode for the majority of each system cycle. Data input to the RAM occurs regularly, but only for 8 μs intervals.

A second major function of the counter module or card is to provide an analog signal output. Despite the fact that digital data acquisition is superior in many ways to conventional analog circuitry, many users are required to work with analog signals. The Digital to Analog (DAC) converter (s17) is thereby provided as an option on the standard tracking units of the preferred embodiment. The DAC of the present invention operates as follows. Successive 8-bit values are latched into one side of the one of four magnitude comparators (s15b,d,f&h). These values are selectable through the software to permit any combination of transmitter/receiver output signals to be transferred to the four analog outputs. The opposite side of comparator 15, is directly connected to the constantly cycling transmitter and receiver bits. When the value applied to both sides of the comparator are equal, the output is passed to a 4-to-2 line encoder (s16), before being passed to a DAC (s17). Under this configuration, four distinct, 12-bit analog channels can be connected to an output port from the computer.

Finally the counter card or module also employ a "glue logic" PLD (s18) to coordinate the timing of the output enable signals, as well as the handling of thirty-two versus sixteen transmit channel capability.

The final digital card or module in the ultrasound system of the present invention is a synchronized Analog to Digital (A/D) converter card or module. During typical experiments, a user may wish to acquire more than the networked distance measurements. For example, in a cardiac investigation, analog signals such as pressure, ECG, and blood flow are also important. For this reason, an expandable A/D card is integrated into the tracking system of the preferred embodiment. The basic system is perfectly provided with four A/D channels. However, up to sixteen independent, 12-bit channels may also be provided ranging from ±10 V.

As illustrated in FIG. 5, the A/D module functions in virtually the same fashion as the counter card. Analog channels are fed in via a db25 cable connection (RGB174U coax connectors) to a1–a4. During the data input mode, all analog channels are internally converted and fed into two 8-bit by 131,072 RAM modules (a6 & a7). The RAM is automatically incremented using the four gated receiver bits (a13). An incrementing address PLD (a14), which receives the same clock as the counter address incrementor, is used to provide the remaining thirteen address lines to the RAM. Thus, every time a complete transmit receive cycle is performed, both the A/D RAM and the counter RAM registers are increased. During the write, or data output mode, an address is written to the respective octal D-type flip-flop (a12) and transceivers (a10 & a11) to access the proper RAM location. The octal buffers a8 and a9 are opened allowing the converted analog information to be transmitted along the high and low byte data buses to the computer storage device. Finally, a controlling PLD (a5) is used to coordinate the timing signals on the A/D module. By congruously activating the A/D and counter information, it is possible to synchronize the digital distance information with the converted analog data.

A second function of the A/D card is to provide for direct digital inputs. Thus, up to four digital input channels may be received via latch a15 and monitored via octal buffer a8 during an experiment in the same fashion as the analog data.

The final hardware component in the ultrasonic tracking system of the present invention is the peripheral transmitter/ receiver/transceiver unit, shown in FIG. 6. Each peripheral board of the preferred embodiment possesses the capacity to support sixteen transmitters with eight receivers, or eight transceivers. These components are mounted onto a two-layer printed circuit board and connected to the host computer system by means of the twenty-four conductor, individually shield computer cable discussed above. The external peripheral unit receives its transmit voltage level and biasing voltages from an independent power supply (t5). The unit also possesses a two colour LED to indicate whether the unit is in active or standby mode.

The peripheral unit works as follows. The digital signals passed from the computer to the unit are passed through pullup resistors to a CMOS 1-of-16 decoder (tr1). The decoded signals are then transmitted to selectable transmitters or transceivers. The variable duration Pulse Length signal is sent via filtering and biasing elements to the gate of an N-Channel Enhancement Mode VMOS transistor (Q3). The gate signal bridges the transmit voltage level to ground. This signal is then passed through a step-up isolation transformer (T1) and out of the peripheral unit via a coated, 32 gauge, multistranded wire to the transducer (t2).

The transducer itself (x1) is preferably a cylindrical piezoelectric ceramic crystal, encapsulated with an electrically insulating sealant.

Using a network of similar receivers, the mechanical vibration from a transmitter crystal is detected and converted to an electrical signal. Each individual receiver circuit consists of step-up isolation transformer (T1), a two stage amplifier (A1) collectively providing a 48 dB gain, a linear operational amplifier (tr3), a half-wave rectifier (D1) and a TTL level inverter (tr4A and tr4B). The digital waveform output from the TTL inverter is further isolated using an RF choke (t9) before it is transmitted back through the shielded cable to the appropriate LLDs.

Figure 7A:
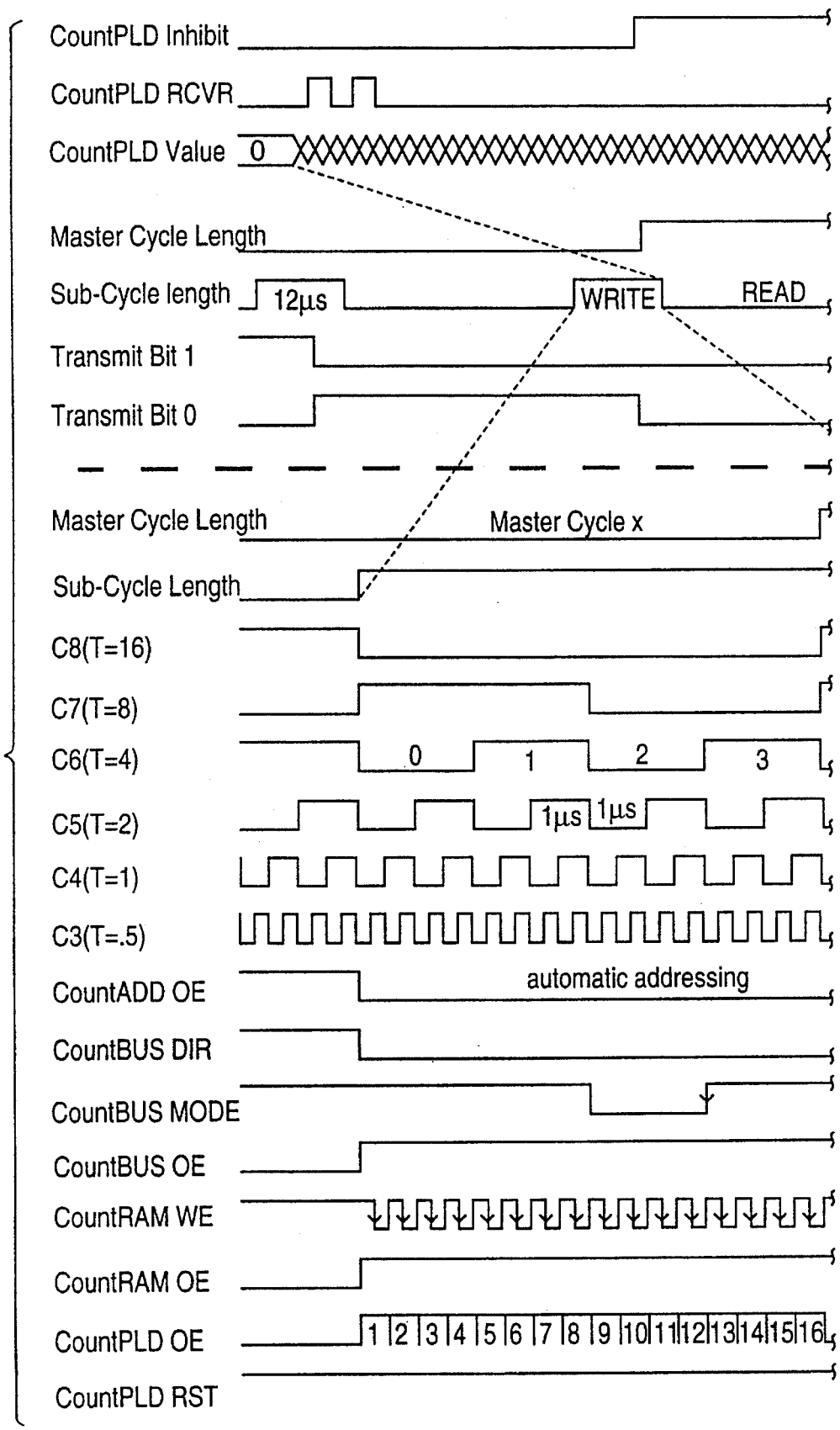
FIGS. 7A and 7B, is a timing diagram showing operation of the counter module according to the preferred embodiment.
Figure 7B:
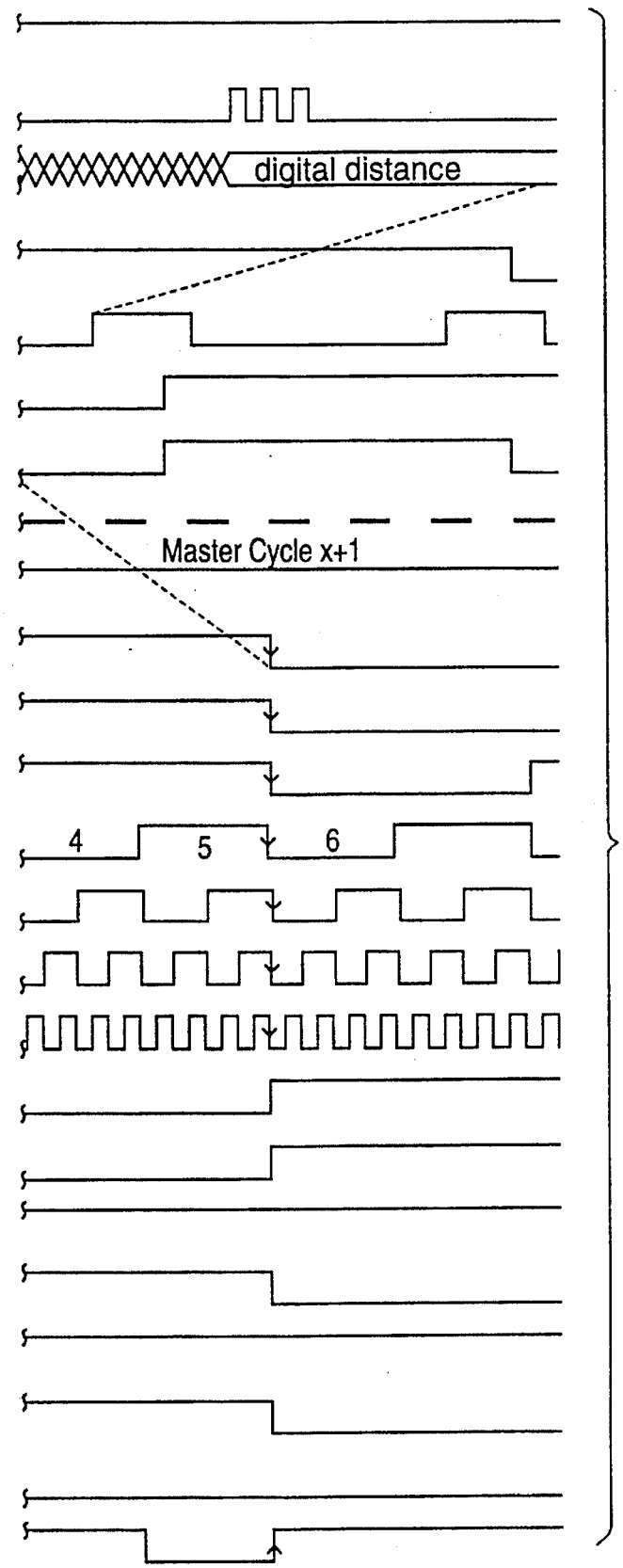
Figure 8A:
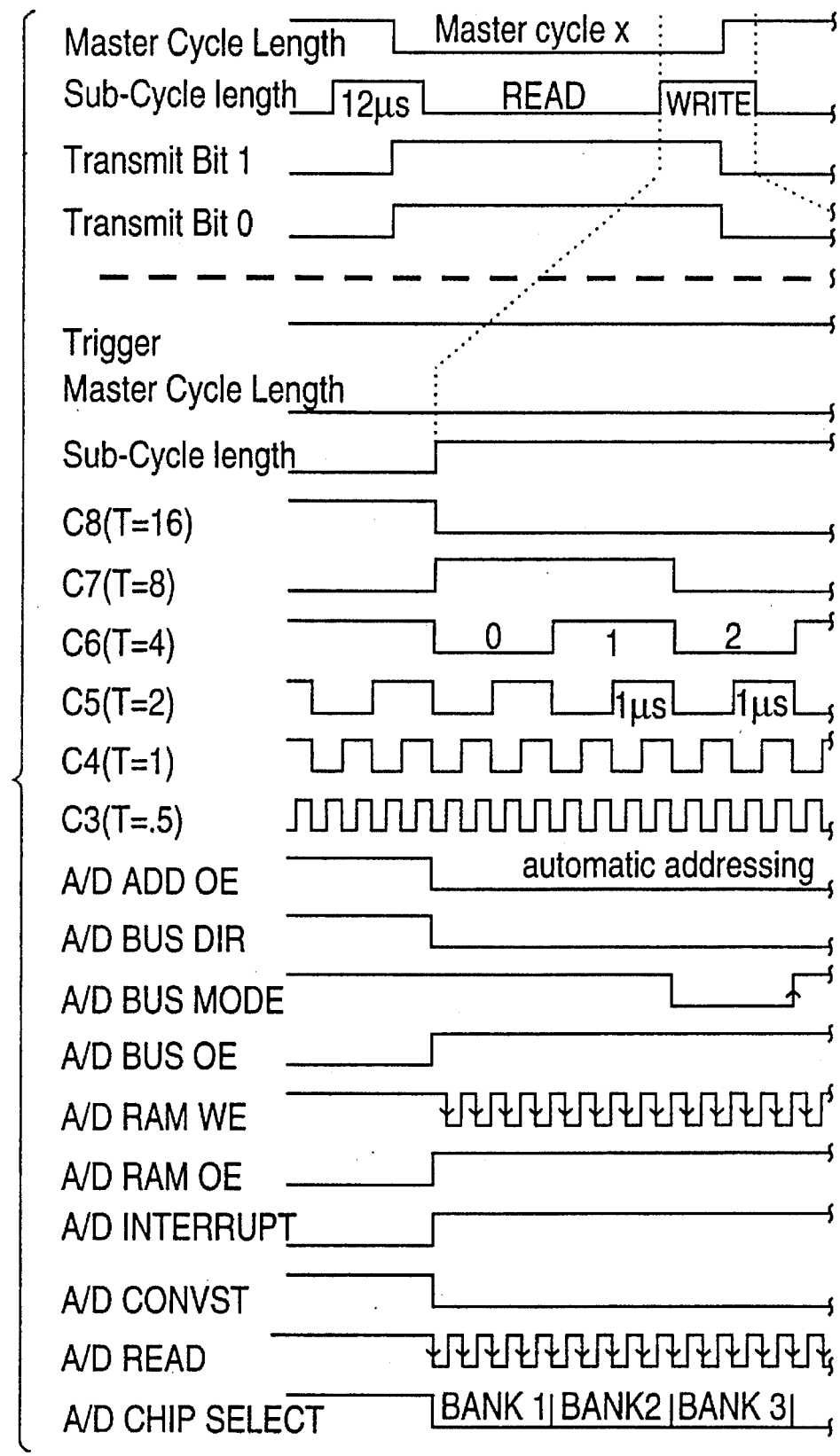
FIGS. 8A and 8B, is a timing diagram showing operation of the A/D module according to the preferred embodiment.
Figure 8B:
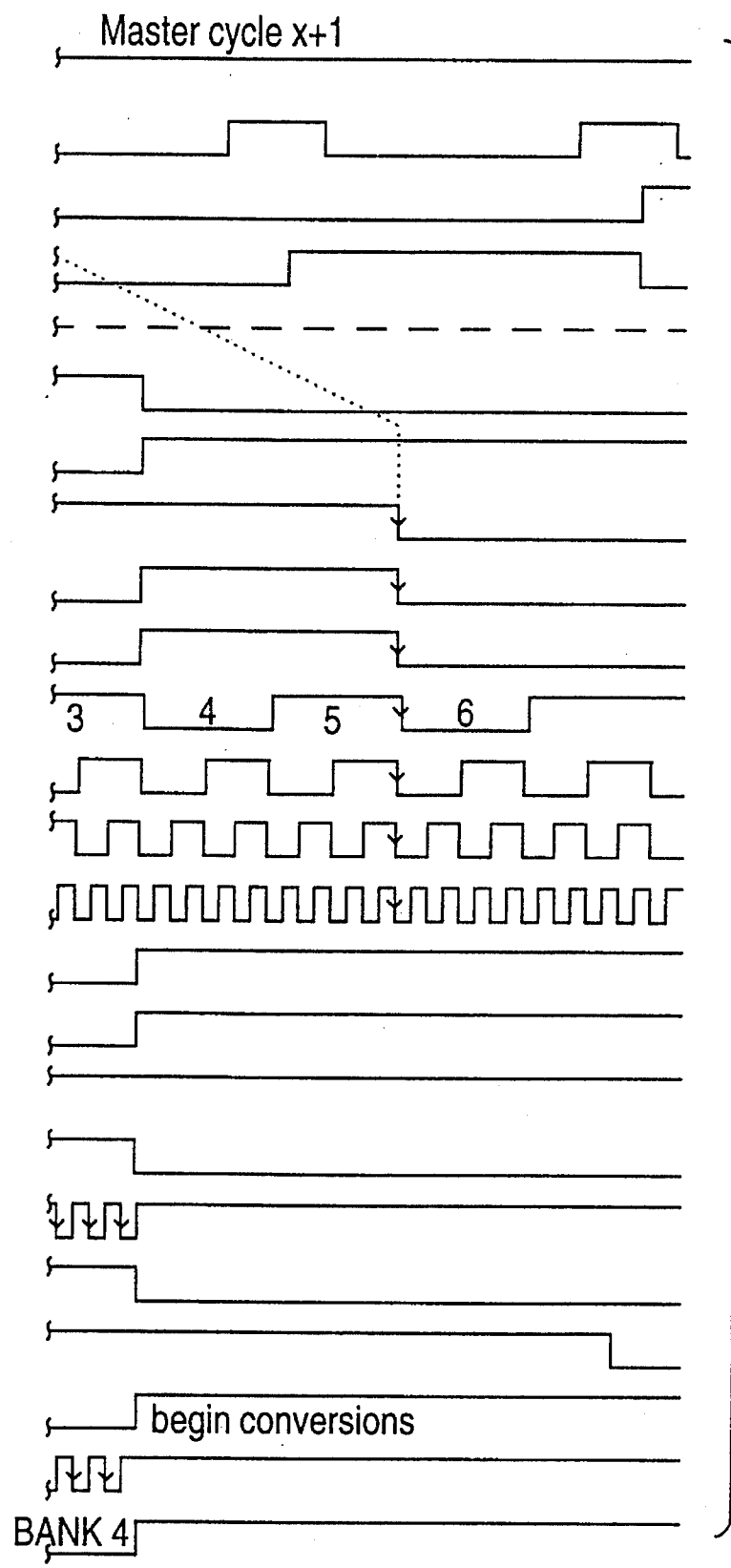

For a further understanding of the operation of the three-dimensional tracking system according to the present invention, a set of timing diagrams are provided in FIGS. 7 and 8. These figures illustrate the operation of the counter module (FIG. 4) and the A/D module (FIG. 5), respectively, during both the read and the write phases of operation. By default, the counter module actively acquires data for sixteen receivers during every Sub-Cycle Length. Conversely, the A/D data acquisition occurs only once during the same time interval, or once every Master Cycle Length. For simplicity, both timing diagrams are based on a transition from a transmitter "x" to a transmitter "x+1". Despite the apparent equal time-sharing between read and write cycles, in actual fact, the read cycle is significantly longer. More particularly, in the preferred embodiment the write cycle is limited to a 12 μs window per sub-cycle.

Referring to FIG. 7, the counter module (FIG. 4) operates as follows. At the beginning of the read cycle, an impulse signal is sent out to the VMOS transistor (t4 in FIG. 6) to activate a transmit crystal (x1). At precisely the same time, the associated counter PLD (s10a–d, s13a–d) is released from its count of zero and begins counting up at a clock speed of 32 MHz. As discussed above, assertion of the CountPLD Inhibit signal prohibits electromagnetic interference between crystal leads by remaining at a logic low level. After a user-adjustable delay, the CountPLD signal changes state, thereby permitting the reception of a valid signal on the associated CountPLD RCVR line (RCVR0–3).

Once the first valid ultrasonic signal is detected and processed, the digital counter value is held on the PLD's output registers. The period of time for this distance count to occur is also variable in duration according to the user's specification. During this time, the transceivers which govern the read/write state of the system permit the downloading of the previously acquired digital distance values from the system RAM (s8,s9) (CountADD OE in a high state). By constantly monitoring the RAM addressing values using s2–s4 (FIG. 4) the computer is able to keep track of the RAM status. As the RAM (s8, s9, FIG. 4) approaches its capacity, a downloading is carried out during this read window.

The write window of operating the counter module is delimited by the 12 μs active high Sub-cycle length signal. At the moment this signal is asserted, the following conditions occur: the CountADD OE signal changes state, indicating that the automatic addressing mode has been invoked, the CountBUS DIR signal changes states to allow the opposite flow of data through the transceivers, the CountBUS OE signal is invoked to activate the output registers of the addressing PLD (s1) the CountRAM OE signal is disabled to prepare the RAM (s8, s9) for data storage, the CountPLD OE signal enables cycling through each of the sixteen individual counters, and the CountRAM WE signal toggles to store each digital count value in RAM (s8,s9). The signals used to control these functions are generated by various Boolean combinations of the control module counter (c1). As the default 4-bit receiver values are cycled through to produce the automatic RAM addressing, the CountBUS MODE signal is toggled to sample the current addressing value generated by the addressing PLD (s1, FIG. 4). This value is stored in memory for proper downloading of data during the next write window. These functions are carried out during the first 8 μs of the 12 μs sub-cycle window.

Once all sixteen receivers (FIG. 6) have downloaded their distance data to the RAM (s8, s9), the Master Cycle length value is incremented to indicate the next major cycle. At the same moment, the CountRAM WE signal is disabled along with the polling of the receiver distance values.

Finally the remaining 4 μs expire putting the counter module back into its read mode, while resetting the receiver chips (CountPLD RST), and each of the incrementing counter bits from the controller card (FIG. 3).

Using FIG. 8 as a guide, the A/D module of the tracking system works in an identical fashion as the counter module, with one major exception. Write modes occur only during transition of the Master Cycle Length signal. When such occur, the default sixteen converted analog channels are cycled through and written to their respective RAM locations. The same A/D BUS MODE sampling occurs to ensure individual RAM chips are provided in banks of four channels, each chip is given a 2 μs window in which the A/D CHIP SELECT signal is toggled low for data throughput. At the end of 8 μs, the A/D parameters are reset to their write state while sampling of the analog channels begins once again. Once the transition has occurred to activate the next array of transmitters, the AD INTERRUPT signal drops to a logic low value to indicate that the conversions of the active channels are complete.

The machine language codes that carry proper collection and processing of data acquired by the peripheral unit (FIG. 6) are all preferably based around a x86 processor. The transfer of information through the system is both quick and seamless. Given a typical system with sixteen transmitters and sixteen receivers, or sixteen transceivers, 256 2-byte distance data saves are carried out every cycle of the Master Cycle length signal. Since the on-board RAM (s8, s9) in a typical unit is 128 kB, the RAM has the capacity to save 512 Master Cycles before overwriting occurs. Since most clinical experiments typically demand a 200 Hz data saving rate to sufficiently track biological motion, only 2.56 seconds of data saving can be correctly obtained.

Since this is clearly unsatisfactory for a typical data run, software routines have been written for the system of the present invention to periodically download the RAM modules during the read cycles of the system.

The transfer of information out of the system is as follows: each time the digital boards (FIGS. 3–5) are accessed, a total of 1024 bytes of data are secured. This 1 kB is written to a dedicated 64 kB buffer in the mother board RAM of the resident PC. Provided that the computer is not responsible for carrying out any additional tasks, the machine language code implemented thereon, also shunts this information to the display. This function can be performed 64 times before the RAM buffer of the mother board RAM is full. Once this happens, the system software performs a binary save of the data held by the 64 kB buffer. At this stage, a standard disk-cache such as DOS's smartdrv.exe is activated to accept all of the 64 kB binary files and commit them to the hard disk drive of the PC at the end of a data save command. Under this scenario, the only limit to the duration of a data save is the capacity of the disk cache. In this manner, the ultrasonic tracking system of the present invention can be tailored to meet the specific needs of customers simply by providing additional memory to the base PC computer.

In addition to data saving and display software, the units according to the present invention preferably also utilize post-processing software routines to manipulate and visualize the saved binary data files.

A detailed description follows, relating to specific clinical applications of the system according to the present invention, and preferred catheter guidance implementation.

i) TRACKING OF CATHETERS THROUGH THE HUMAN CIRCULATORY SYSTEM

Catheters are devices that are inserted into the veins or arteries of humans as part of a procedure in which qualified hospital personnel remove blockages and obstructions from the circulatory system, or correct other related problems. The three dimensional digital ultrasound tracking system of the present invention may be configured to operate as a guidance system that can be used to track all types of catheters.

The current method of tracking catheters involves frequent exposure of the patient to an x-ray source. Each successive x-ray provides information on the movement of the catheter(s) within the patient.

In addition, contrast agents are frequently injected into patients during catheter procedures. These injections can provide further information on the actual location of the catheter and help physicians to plan subsequent catheter movements.

X-ray radiation and contrast agent injections are each potentially harmful to the health of the patient. Further, these methods of tracking are also time consuming, often introducing additional stress and patient complications.

Three primary advantages result from the present invention when used to track catheters:

1) The need for using harmful x-rays and contrast agents are virtually eliminated while determining the location of catheter(s) within the patient;

2) Procedure times are substantially reduced with benefits in both safety and cost; and 3) Extremely exact positioning of the catheter is obtained as a result of the theoretical resolution of 48 μm.

The basic principle of the Catheter Guidance System (CGS) of the present invention involves the establishment of an internal reference frame and an (optional) external reference frame in three dimensions from which the catheter can be traced. Using the transceiver hardware and the triangulation algorithm discussed above, the crystal positioning data can be captured and processed to resolve the location of the catheter of interest.

To further facilitate visualization of the catheter location by the administering hospital staff, the crystal position information may be overlaid onto a recorded video loop of the region of interest. This video loop can be generated from an imaging modality such as x-ray or scanning ultrasound and is meant to illustrate the natural movement of the biological structure(s) during one or more cardiac cycles. In addition to this, the video loop can also depict the position of the opaque piezoelectric transducers (X1) used by the CGS to tract the catheters. These piezoelectric transducers serve as "landmarks" (whether they are internal or external). By identifying these "landmarks" in the video, the positions of the guiding piezoelectric crystals can be correlated with the captured video information. In this fashion, the imaging process and the ultrasound positioning process can be linked for one or more complete cardiac cycles. Once the imaging modalities are linked, the graphic video loop can be substituted for the potentially harmful imaging (and contrast agent injections) throughout the rest of the procedure.

Typically, the catheters used in these procedures are introduced into the body through the femoral vein. From the point of entry, the catheters are pushed and steered, using internal guide wires to the region of interest, usually the human heart. Physically, the catheters are constructed with a biocompatible plastic and feature such options as electrode sensors and actuators for detecting the cardiac activity in electrophysical operations to inflatable balloons for arterial expansion in angiology procedures.

A concept that is of importance in implementing the Catheter Guidance System (CGS) application of the present invention is the merging of piezoelectric transducers and the imaged catheters. Since the design of catheters used for these procedures are well established, consideration has been given to the design of the ultrasonic sensor, including the following aspects:
1. The type of ceramic material used.
2. The encapsulation procedure.
3. The shape of the transducer.
4. The operating frequency.
5. The activation procedure.

The material selected for use in both the internal and external reference frames must possess superior transmission and reception characteristics in order to properly communicate with each other. Since operating temperatures inside the human body are not a major concern, a higher dielectric material with lower Curie temperature can be employed. Essentially, this provides for an increased ultrasonic output per input volt. The preferred material for this purpose is Lead Zirconate Titanate.

Since these materials are non-biocompatible, an appropriate encapsulation material is used. The encapsulant must not only be biocompatible, but must also possess an acoustic impedance that does not hinder the ultrasonic wave propagation. This is of key importance for the internal reference frame transducers or crystals. The external reference crystals require an acoustic coupling gel similar to that used for standard B-type ultrasound scans.

Omni-directional ultrasound transmission, cylindrical crystals (X1) are used for the internal reference frame. The cylindrical transducers maintain omni-directional radiation patterns while demonstrating excellent transmission and reception characteristics. Externally, larger disk-type crystals are employed. Since the external reference frame serves as a redundant backup, it is less crucial that these transducers possess exceptional transmission capabilities.

Due to the variable software controls of the ultrasonic tracking system according to the present invention, activation frequency can be optimized for maximum performance and efficiency. In the case of the internal reference frame, smaller distances are monitored, therefore higher operating frequencies can be used. The opposite is true of the external reference frame.

Figure 9:
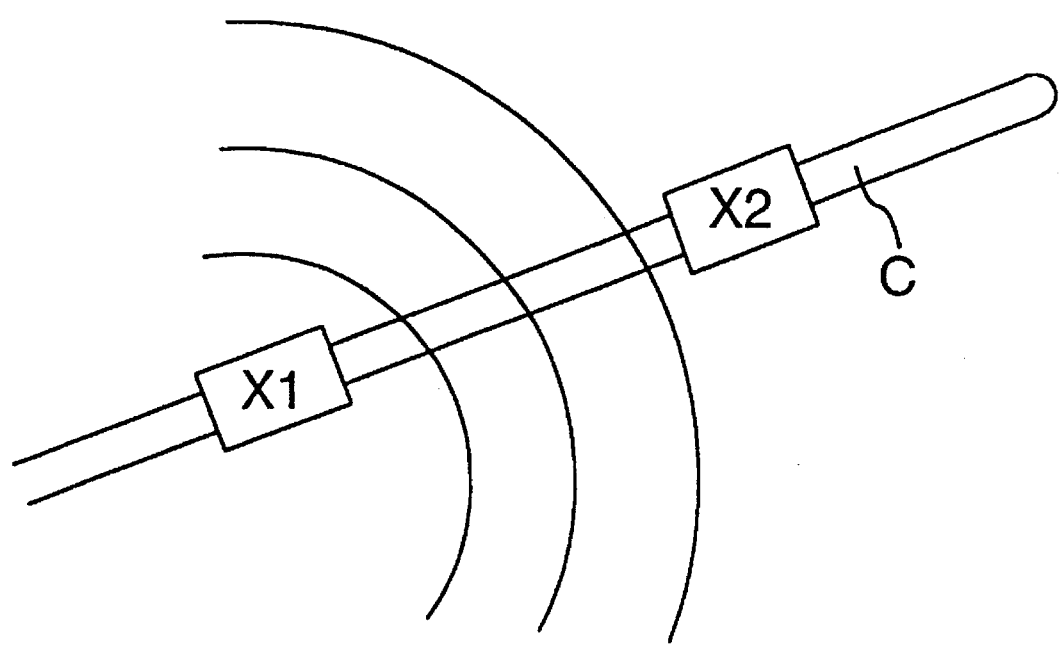
FIG. 9 is a schematic illustration of a catheter guidance system according to a specific implementation of the present invention.

For both reference frames, the method of transducer activation is identical. This process in discussed in detail above with reference to FIG. 6. An insulated conducting wire is used to carry the activation impulse from the control unit to the transducers. In the case of the catheter crystals, the signal wires are internally routed through the same sheath as the steering guide wires. Finally, placement of the crystals is contingent upon which reference frame is employed. FIG. 9 illustrates the placement of the cylindrical transducers with respect to the catheter tip, according to the proposed catheter guidance application of the present invention. As can be seen, two ultrasonic crystals (X1, X2) are used on each catheter. This permits the crystals to communicate with each other, as well as to every other internally placed crystal in the region. By using the information from two concentric crystals on a catheter, vector data can be acquired to illustrate not only the position of the tip, but also the direction.

As can be seen, the two crystals (X1, X2) are permanently positioned concentrically along the axis of the catheter (C) at a separation distance sufficient to distinguish reception signals, but close enough to indicate the directionality of the tip. The method of diffusing the piezoelectric material onto the tip is similar to the process by which the electrode sensors are placed on common electrophysiology catheters.

Figure 10:
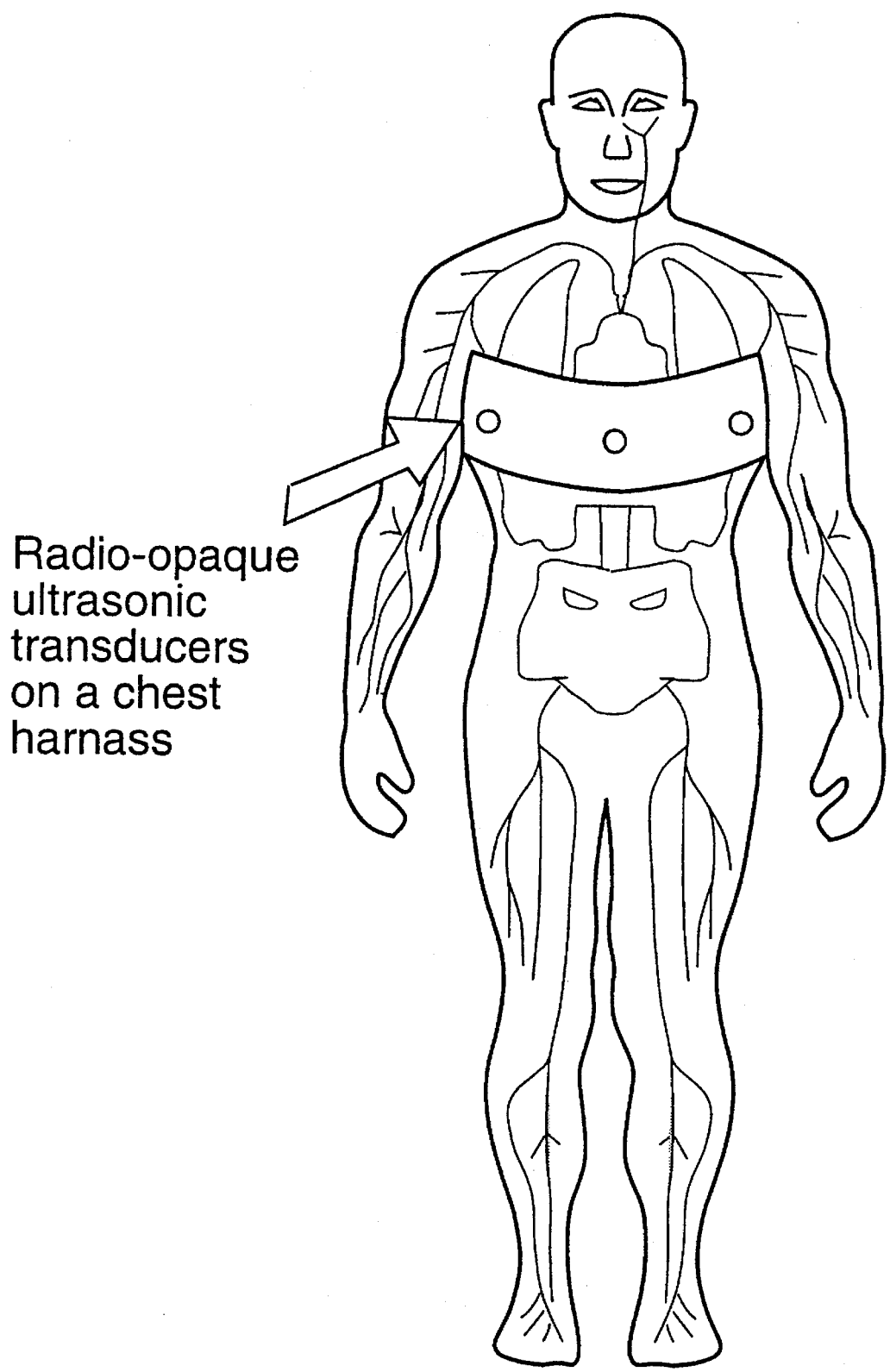
FIG. 10 is a schematic illustration of the external reference frame of the catheter guidance system according to the implementation of FIG. 9.

FIG. 10 illustrates the manner in which the external crystals are placed. The purpose of the external reference frame is to monitor the accuracy and movement of the crystals on the catheters. As can be seen, the larger disk crystals are placed in a harness-type apparatus that is worn around the chest by the patient during the procedure. A number of radio-opaque transducers are fastened to the harness in locations suitable for optimal signal reception through the chest cavity.

Under the disclosed configuration, it is possible to monitor the position and direction of the catheters that are introduced into the human circulatory system. This methodology significantly reduces both the risk and the procedural time associated with current electrophysiology and angiology operations, while providing improved positioning accuracy.

ii) TRACKING OF INTRAVASCULAR ULTRASOUND CATHETERS THROUGH CORONARY AND THROUGH PERIPHERAL VEINS

The tracking of catheters can be extended into the field of intravascular ultrasound. If a vessel has multiple stenoses, it is important to know exactly which one is being imaged with the intravascular ultrasound device. The traditional method involves the injection of contrast agent under fluoroscopy, but this method suffers from the above mentioned risks. The intravascular ultrasound catheter can be easily tracked by using a low frequency transmitter mounted near the imaging head of the catheter. By having a dual display showing the view inside the vessel with the ultrasound, and the position of the imaging area relative to the gross morphology of the vessel on the angiogram, the angiologist can better treat the lesions and reduce the procedural risks to the patient.

iii) TRACKING THE BIOPSY NEEDLES OR BIOPSY CATHETERS

The tracking of biopsy catheters is of particular interest, because occasionally the biopsy "bites" are taken from the wrong part of the heart. Sometimes a piece of the coronary artery is cut off, or the cardiac valve is damaged, with obvious complications to the patient. By following the path of the biopsy catheter, using the single angiogram and real time overlay of the tracked catheter, the biopsy procedure itself can be made more precise and safe.

Needles can also be tracked with ultrasound, such as when cannulating the carotid artery or the femoral artery. An existing unit is available for this procedure, but it relies on having the needle cast a faint shadow in the B-mode ultrasound image. This shadow is not readily visible to the untrained eye, and has obvious limitations in precision. A true 3-D tracking of the needle under real time ultrasound using the principles of the present invention greatly simplifies such procedures.

iv) GUIDING OF PROBES DURING STEREOTACTIC SURGERY

During some delicate surgeries, particularly in the brain, it is important to know the 3-D position of the probe inserted into the head very precisely. The conventional method involves rigidly fastening the patient's head to a stereotactic frame by placing screws and pins into the patient's skull. The patient, with the frame attached, is then imaged using MRI or CAT, and a 3-D reconstruction of the patient's head is created. Pathologic tissue or lesions, such as tumours, are then precisely located relative to the frame. The patient is then taken to the operating room and the required instruments, such as electrodes or ablators, are affixed to guides that allow the instruments to be moved along the specific paths into the patient's head. Once the surgical instrument is in place, the lesion can be corrected, destroyed or treated in some way.

This approach is tedious, costly and subject to measurement error in translating the 3-D coordinates from the images to the actual position of the probes within the stereotactic frame.

An alternative to this approach involves the use of a 3-D wand. This instrument consists of an articulating metallic arm that is rigidly affixed to a surgical table. Each of the joints in the arm has an angular position sensor so that the 3-D coordinates of the tip can be calculated from the joint sensors. By matching visual landmarks on the patient's head to the same landmarks on the 3-D image using the probe, the head and the image can be registered with each other. The probe is then used during surgery to hold instruments and guide them into the brain in a manner similar to the stereotactic frame. The advantage of the wand is that it has many more degrees of freedom, and can be held by the surgeon. The disadvantage is that it is very expensive, and very bulky. Also, the position of the probe tip is always only as precise as the original calibration against the patient's head. The patient's head must remain rigidly affixed to the table to which the articulating arm is fixed.

A further application of the tracking system according to the present invention involves placing reference crystals anywhere on the patient's head, and an active crystal on the tip of the probe. As the probe is inserted into the head, its movement relative to the reference crystals can be tracked in real time 3-D. The crystals affixed to the head can be imaged along with the patient, simplifying the registration process, and since they are affixed to the head, movements of the head relative to the operating table do not pose a problem with respect to tracking.

Patients with electrical disturbances of the brain, such as epilepsy, need to have the location of the epilepsy mapped properly prior to surgical intervention. This is done by placing surface electrodes subdurally over the brain. These electrodes are pushed along the brain through small access holes drilled into the skull, and their location is often difficult to know precisely. By placing transmitter or receiver crystals on the electrode pad, and complementary electrodes on the outside of the skull, according to the principles of the present invention, the motion of the electrodes can be tracked in real time, or can be verified with images of the brain taken previously. This greatly simplifies the mapping of brain wave activity anomolies.

vi) TRACKING OF AMNIOCENTESIS NEEDLES

Another application of the real time tracking system of the present invention in the tracking of biopsy needles for use in the procedure of amniocentesis. A real time ultrasound image with the motion of the needle displayed can prevent injury to the fetus.

vii) MEASUREMENT OF CERVICAL DILATION

The onset of labour can be a well controlled process. During the first set of contractions, nurses periodically track the dilation of the cervix. This is done manually by overlaying a calibrated gauge over the cervix and reading off the amount of dilation. These dilations are done at regular intervals and a time/dilation curve is plotted. This allows the obstetrician to plan the delivery, as the major contractions come once the rate of cervical dilation increases.

The plotting of such dilation curves can be automated and managed for many mothers in the delivery room by measuring the dilation of the cervix with ultrasonic crystals according to the principles of the present invention.

In this way, a maternity ward can be networked so that progress of many mothers through labour can be monitored remotely by a few nurses at a central station. the obstetrician is thus able to predict which patient is due to deliver at what time and can plan his or her activities more precisely.

viii) ASSESSMENT OF JOINT MOTION TO LOOK AT STABILITY OF THE KNEE

In some orthopaedic procedures, the stability of the knee needs to be evaluated quantitatively during walking. Knee stability can be assessed through manual manipulation, but only a complex imaging technique can map the motion of the knee during walking. By implanting the sonomicrometer crystals of the present invention in the knee, the relative motion of the joints can be measured quantitatively during normal gain, and any surgery to augment ligaments can be better planned.

ix) ASSESSMENT OF MYOCARDIAL CONTRACTILITY FOLLOWING SURGERY

Following open heart surgery to repair the myocardium or the coronary arteries, the patient has to be monitored to adjust the levels of drugs that are administered. This is referred to "titration" of drugs. The myocardial contractility is measured with a Swan-Ganz catheter and the drug level adjusted to obtain optimal cardiac function. Unfortunately, the Swan-Ganz catheter is an indirect measure of contractility and can produce inadequate data.

A pair of sonomicrometer crystals, however, provide a direct measure of myocardial contractility if attached to the beating ventricle. These transducers can be attached to the myocardium during open chest surgery and can measure the contractility of the heart directly while the chest is open. The leads can then be strung out through the chest wall, and monitoring of myocardial contractility can continue for a few hours or days post operatively. This approach replaces the less precise Swan-Ganz catheter, and can be used to titrate the drugs given to the patient. If the crystals are properly positioned, the can be removed post operatively by pulling on them, in much the same way that pacing electrodes are removed.

Alternative embodiments and variations are possible within the sphere and scope of the invention as defined by the claims appended hereto.

I claim:

1. A digital ultrasound tracking system, comprising:
    a) a plurality of spaced apart ultrasound transceivers;
    b) a controller module connected to said plurality of spaced apart ultrasound transceivers for selectively enabling individual ones of said transceivers to operate as one of either a transmitter or a receiver, and for energizing each respective transmitter such that each said transmitter generates an output oscillation signal which is detected by at least one associated receiver; and c) a counter module connected to said plurality of spaced apart ultrasound transceivers and said controller module, said counter module including a high speed counter associated with each said associated receiver for generating a digital count value corresponding to an elapsed time between said energizing of the transmitter and detection of said output oscillation signal by said at least one associated receiver.

2. The digital ultrasound tracking system of claim 1, wherein said controller module further includes circuitry for adjusting repetition rate of said energizing of each transmitter.

3. The digital ultrasound tracking system of claim 1, wherein said controller module further includes circuitry for adjusting duration of said energizing of each transmitter.

4. The digital ultrasound tracking system of claim 1, wherein said controller module further includes circuitry for inhibiting each said high speed counter for a variable period after energizing of each said transmitter, thereby avoiding count errors due to electromagnetic interference resulting from energizing of each said transmitter.

5. The digital ultrasound tracking system of claim 1, wherein each of said transceivers further comprises:

d) a transmitter input for receiving a digital input signal from said controller module;

e) a step-up isolation transformer for translating said digital input signal into a crystal energizing signal;

f) a piezoelectric crystal for receiving said energizing signal in transmit mode and in response generating said output oscillation signal, and for detecting said output oscillation signal in receiver mode and in response generating and applying an input oscillation signal to said step-up transformer;

g) circuitry connected to said step-up transformer for amplifying and converting said input oscillation signal to a digital output signal; and h) a receiver output for transmitting said digital output signal to said counter module for halting the high speed counter associated therewith at said digital count value.

6. A three dimensional ultrasound tracking system for attachment to an object whose position is to be monitored, comprising:

a) three ultrasound transceivers mounted to said object so as to form a first two-dimensional plane;

b) a fourth ultrasound transceiver mounted to said object on one side of said two-dimensional plane;

c) a plurality of ultrasound transmitters arranged in three-dimensional space around said ultrasound transceivers; and d) circuitry for (i) sequentially enabling respective ones of said transmitters to generate ultrasound signals for reception by said ultrasound transceivers, (ii) sequentially measuring elapsed time between generation of said ultrasound signals and reception thereof by respective ones of said transducers, and (iii) calculating via triangulation from said elapsed time position and orientation of said object relative to said plurality of ultrasound transmitters.

7. A catheter guidance system, comprising:

a) at least two piezoelectric crystals mounted adjacent a tip of a catheter for insertion into a patient, whereby said at least two piezoelectric crystals form an internal reference frame;

b) a plurality of additional piezoelectric crystals located externally of the patient so as to form an external reference frame;

c) circuitry for (i) sequentially enabling respective ones of said piezoelectric crystals to generate ultrasound signals for reception respective other ones of said piezoelectric crystals, (ii) sequentially measuring elapsed time between generation of said ultrasound signals and reception thereof by said respective other ones of said piezoelectric crystals, and (iii) calculating via triangulation from said elapsed time, position and orientation of said catheter relative to said plurality of additional piezoelectric crystals.

8. The catheter guidance system of claim 7, wherein each of said two piezoelectric crystals are fabricated from a high dielectric material having low Curie temperature.

9. The catheter guidance system of claim 8, wherein said material is lead zirconate titanate.

10. The catheter guidance system of claim 7, wherein each of said piezoelectric crystals is coated with a layer of radio-opaque material for contrast with said catheter during x-ray imaging of said patient.

11. The catheter guidance system of claim 10, wherein each of said piezoelectric crystals coated with a layer of radio-opaque material is further encapsulated in biocompatible material having an acoustic impedance which does not interfere with propagation of said ultrasound signals.

12. The catheter guidance system of claim 7, wherein each of said two piezoelectric crystals are cylindrical for generating omnidirectional ultrasound radiation patterns.

13. The catheter guidance system of claim 7, wherein each of said additional piezoelectric crystals are disk-shaped and of larger size than said two piezoelectric crystals.

14. The catheter guidance system of claim 7, further comprising a coated stainless steel wire connecting said two piezoelectric crystals to said circuitry, said wire being disposed in an internal sheath within said catheter which also houses steering guide wires of said catheter.

15. The catheter guidance system of claim 7, wherein said two piezoelectric crystals are positioned concentrically along an axis of said catheter and spaced sufficiently apart to prevent signal interference therebetween but sufficiently close to indicate directionality of said tip of said catheter.

16. The catheter guidance system of claim 7, wherein said additional piezoelectric crystals are mounted to a harness adapted to be worn by said patient.

* * * * *